(12) United States Patent
Koussa et al.

(10) Patent No.: US 10,823,699 B2
(45) Date of Patent: Nov. 3, 2020

(54) GEL ELECTROPHORESIS DIAGNOSTIC KIT AND METHODS OF USING THE SAME

(71) Applicant: Vital Biosciences, Inc., Kitchener (CA)

(72) Inventors: Mounir A. Koussa, Dorchester, MA (US); Calvin Domenico, Herndon, VA (US); Ronald L. Green, Bethel, CT (US); Joshua John Forman, Winchester, MA (US); Andrew Ward, Everett, MA (US); Lisa Caldwell, Westford, MA (US)

(73) Assignee: Vital Biosciences, Inc., Kitchener, ON (CA)

( * ) Notice: Subject to any disclaimer, the term of this patent is extended or adjusted under 35 U.S.C. 154(b) by 25 days.

(21) Appl. No.: 16/321,723

(22) PCT Filed: Jul. 28, 2017

(86) PCT No.: PCT/US2017/044544
§ 371 (c)(1),
(2) Date: Jan. 29, 2019

(87) PCT Pub. No.: WO2018/023088
PCT Pub. Date: Feb. 1, 2018

(65) Prior Publication Data
US 2019/0317046 A1  Oct. 17, 2019

Related U.S. Application Data

(60) Provisional application No. 62/452,429, filed on Jan. 31, 2017, provisional application No. 62/368,635, filed on Jul. 29, 2016.

(51) Int. Cl.
*G01N 27/453* (2006.01)
*G01N 33/561* (2006.01)
*G01N 27/447* (2006.01)

(52) U.S. Cl.
CPC ..... *G01N 27/453* (2013.01); *G01N 27/44743* (2013.01); *G01N 33/561* (2013.01)

(58) Field of Classification Search
CPC ........... G01N 27/453; G01N 27/44791; G01N 27/44743
See application file for complete search history.

(56) References Cited

U.S. PATENT DOCUMENTS 3,586,380 A * 6/1971 Alibeckoff .............. A61F 13/38
300/21
2008/0124752 A1 5/2008 Ryals et al.
(Continued)

FOREIGN PATENT DOCUMENTS

CA 2355875 7/2001
WO WO 2013/067489 A1 5/2013
(Continued)

OTHER PUBLICATIONS

Yang et al., "An integratable microfluidic cartridge for forensic swab samples lysis," Forensic Science International: Genetics 8 (2014) 147-158 (Year: 2014) plus Supplementary Material, one page.*

(Continued)

*Primary Examiner* — Alexander S Noguerola
(74) *Attorney, Agent, or Firm* — Morgan, Lewis & Bockius LLP

(57) ABSTRACT

An electrophoretic device for detecting biomarkers in collected bodily fluid and methods of using the same.

60 Claims, 61 Drawing Sheets

(56) References Cited

U.S. PATENT DOCUMENTS

| | | |
|---|---|---|
| 2008/0160630 A1 | 7/2008 | Liu et al. |
| 2008/0260581 A1 | 10/2008 | Rosman et al. |
| 2009/0061450 A1* | 3/2009 | Hunter .............. B01L 3/502715 |
| | | 435/6.11 |
| 2010/0275282 A1 | 10/2010 | Round et al. |
| 2011/0011742 A1* | 1/2011 | Mathers ................... C07K 1/26 |
| | | 204/462 |
| 2014/0255939 A1 | 9/2014 | Wong et al. |
| 2016/0279257 A1 | 9/2016 | Koussa et al. |

FOREIGN PATENT DOCUMENTS

| | | | | |
|---|---|---|---|---|
| WO | WO 2014/025500 | * | 2/2014 | .............. C12Q 1/68 |
| WO | WO 2015/006626 A1 | | 1/2015 | |
| WO | WO 2016040059 | | 3/2016 | |
| WO | WO 2016/089588 A1 | | 6/2016 | |
| WO | WO 2017/003950 A2 | | 1/2017 | |
| WO | WO 2017/139409 A1 | | 8/2017 | |
| WO | WO 2017/165585 A1 | | 9/2017 | |
| WO | WO 2018/119437 A2 | | 6/2018 | |

OTHER PUBLICATIONS

Hopwood et al., "Integrated Microfluidic System for Rapid Forensic DNA Analysis: Sample Collection to DNA Profile," Anal. Chem. 2010, 82, 6991-6999 (Year: 2010).*

Fiore et al., "Ultrafast capillary electrophoresis isolation of DNA aptamer for the PCR amplification-based small analyte sensing," frontiers in Chemistry, published Aug. 12, 2015 (Year: 2015).*

Hansen, et al., "Nanoswitch-linked immunosorbent assay (NLISA) for fast, sensitive, and specific protein detection," PNAS Early Edition, 2017, pp. 1-6.

Koussa, et al., "DNA nanoswitches a quantative platform for gel-based biomolecular interaction analysis," Nature Methods, 2014, 30 pages.

Koussa, et al., "Protocol for sortase-mediated construction of DNA-protein hybrids and functional nanostructures," NIH, 67(2), 2014, 20 pages.

* cited by examiner

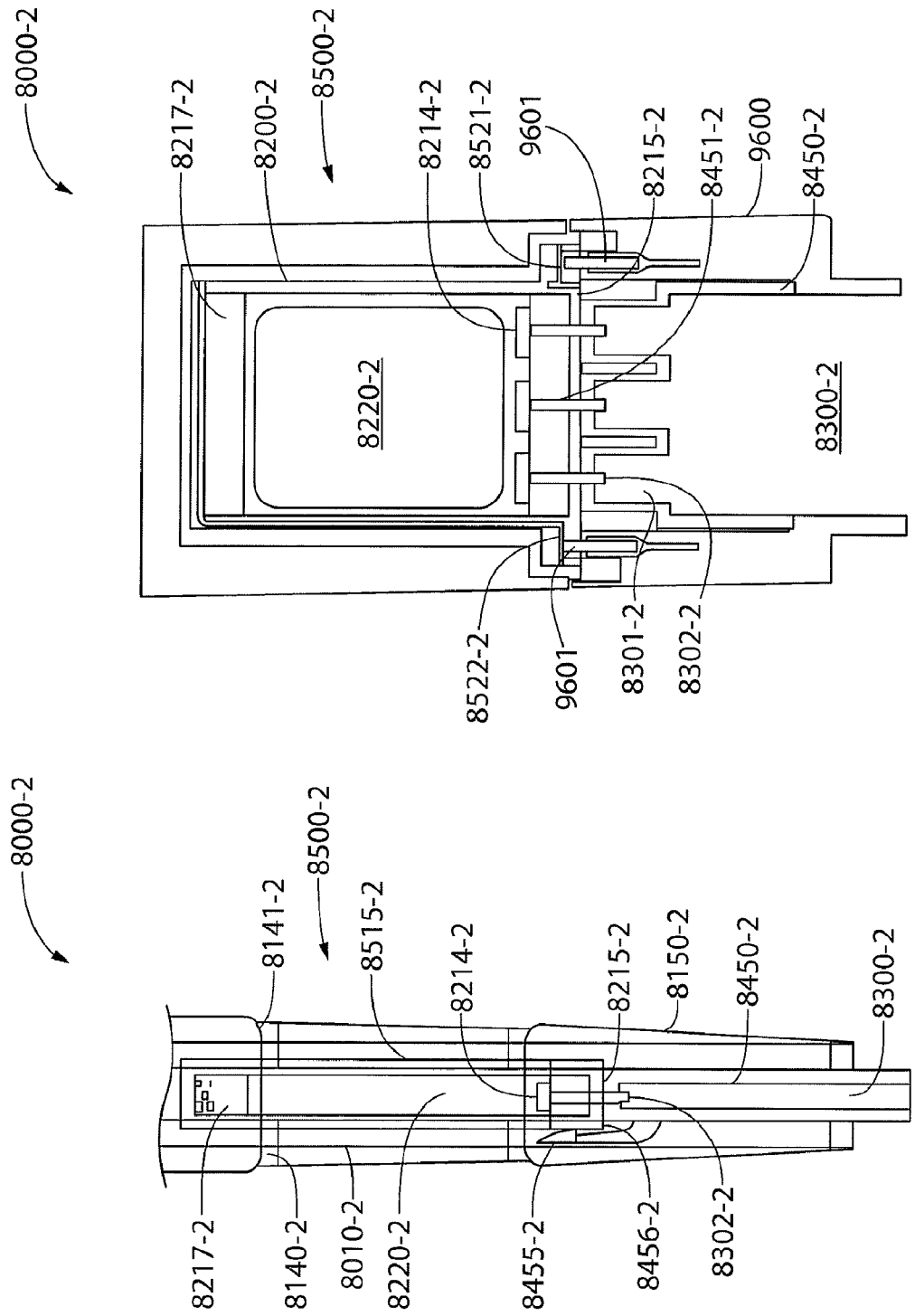

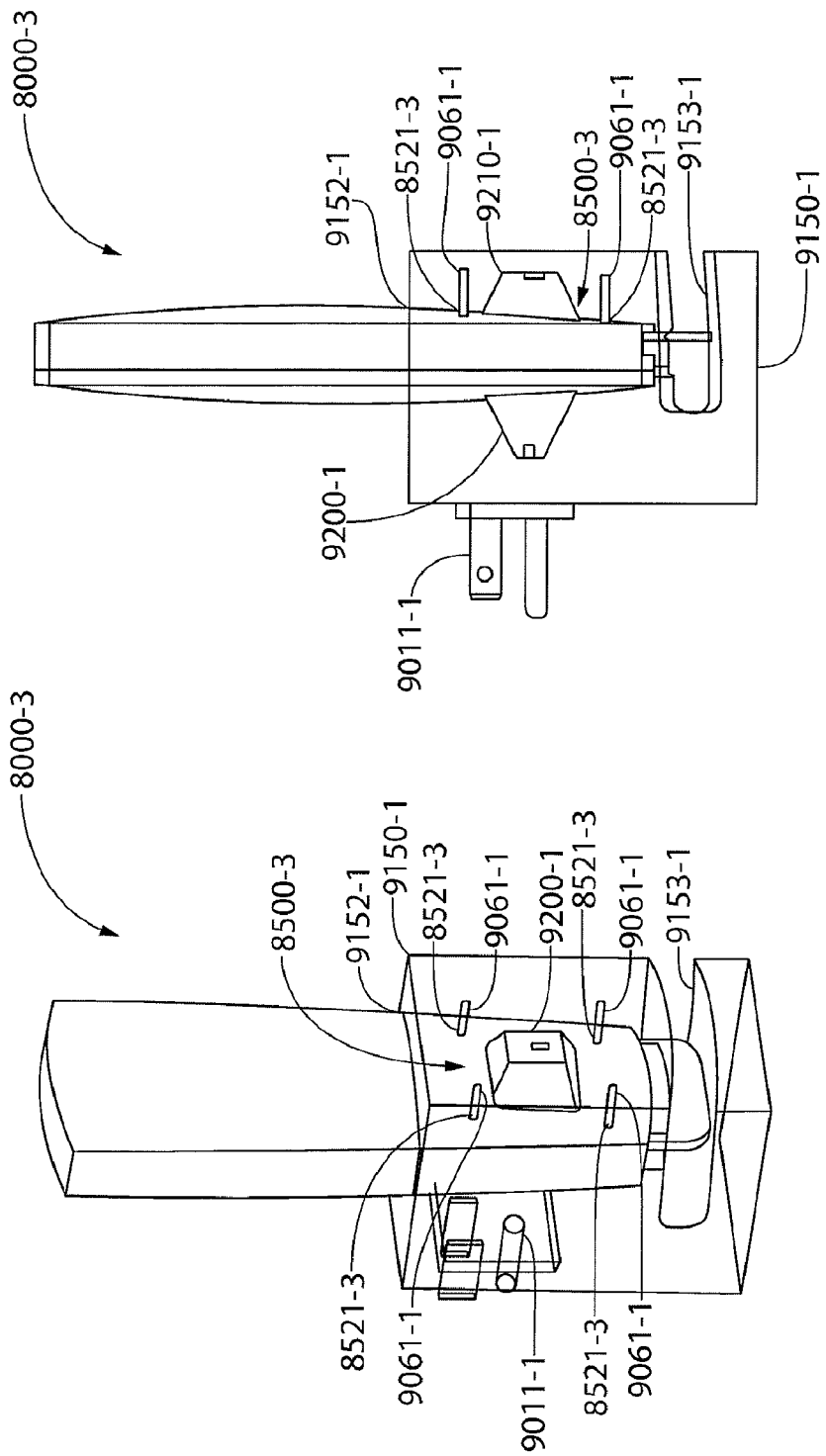

GEL ELECTROPHORESIS DIAGNOSTIC KIT AND METHODS OF USING THE SAME

CROSS-REFERENCE TO RELATED APPLICATIONS

This international application claims the benefit of priority of U.S. Provisional Application No. 62/368,635, filed Jul. 29, 2016, and U.S. Provisional Application No. 62/452,429, filed Jan. 31, 2017, the entirety of which are incorporated herein by reference.

FIELD OF THE INVENTION

The invention relates generally to an electrophoresis device and more particularly, in some embodiments, to an electrophoresis device that includes a biomarker detector cartridge.

BACKGROUND OF THE INVENTION

People tend not to seek diagnosis until they are very sick or hospitalized. This is largely due to the inaccessibility, high complexity, and high cost of clinical-grade diagnostics.

The devices and methods disclosed herein meet a need in the field by providing easy-to-use diagnostic tools that may be used in the home.

BRIEF SUMMARY OF THE INVENTION

Disclosed herein are devices and methods for analyzing a sample of bodily fluids by electrophoresis and thereby detecting the presence of a marker, such as a biomarker, for a biological event that may be present in such bodily fluids.

In an embodiment, a biomarker detector cartridge is provided which may include a cartridge body. The biomarker detector cartridge may include a fluid collector that may be coupled to the cartridge body and may be configured for collecting a fluid that may include a biomarker. The biomarker detector cartridge may include an electrophoretic cell that may be coupled to the cartridge body and may include a separation medium. The biomarker detector cartridge may also include a nanoswitch source that may be disposed in the cartridge body and may be configured to contact the fluid. In some embodiments, the fluid collector may be separable from the biomarker detector cartridge such that a sample may be collected by the fluid collector (e.g., a foam collector) and then may be coupled to or otherwise inserted into the biomarker detector cartridge to provide fluidic communication between the electrophoretic cell and the fluid collector.

In another embodiment, a base is provided for processing a biomarker detector cartridge. The base may include a biomarker detector cartridge receiver. The base may include electrical contacts that may be proximate to the cartridge receiver and may be configured to communicate with an electrophoretic cell in the cartridge. The base may also include an electrophoresis cell reader that may be proximate to the cartridge receiver and may include, for example, one or more of a photodetector, a light source, and a light filter. In some embodiments, an electrophoresis cell reader may be coupled to the biomarker detector cartridge and/or the electrophoretic cell and may include one or more of a photodetector, a light source, and a light filter.

In another embodiment, a method is provided for detecting a biomarker in a fluid. The method may include the step of collecting a fluid that may include a biomarker with a fluid collector of a biomarker detector cartridge. The method may include the step of contacting the fluid with a nanoswitch source. In some embodiments, the method may include the preliminary step of coupling the electrophoretic cell to the biomarker detector cartridge and providing fluid communication between the electrophoretic cell and the fluid collector. The method may include the step of transferring the fluid to an electrophoretic cell of the biomarker detector cartridge. The method may include the step of connecting the biomarker detector cartridge to a base for processing such cartridges. The method may include the step of processing a separation medium at the electrophoretic cell and performing electrophoretic analysis at the separation medium. The method may include reading the processed separation medium with an electrophoresis cell reader at the base or, in some embodiments, on the biomarker detector cartridge, where such cartridge includes an electrophoresis cell reader coupled thereto.

For example, the biomarker detector cartridges may include a gel film in an electrophoretic cell with two electrical leads for running an electrophoretic separation. The biomarker detector cartridge may include a tube or channel running through the midline of the cartridge, which may connect to an absorbent sponge that may be disposed at one end of the cartridge. The biomarker detector cartridge may include a cap (e.g., a plastic cap) that may cover the gel film, which may be exposed at the other end of the cartridge, opposite the absorbent sponge. A user may, grasping the cap, hold the exposed, absorbent end in their urine stream much like a conventional home pregnancy test that would be known to a person having ordinary skill in the art. Without touching the absorbent end, the user may remove the cap from the gel film end of the biomarker detector cartridge and cap the absorbent sponge end of the cartridge. Placing the cap over the absorbent sponge may push the urine through the tube or channel inside the biomarker detector cartridge. In some embodiments, the cap may be substantially longer than the fluid collector and may be a sleeve that may be used to substantially increase the length of the biomarker detector cartridge, which may allow a user to grasp the sleeve during collection of a bodily fluid and reduce the risk of a patient's contact with the bodily fluid. This tube or channel may include a source of nanoswitches so that as the urine passes over the source of nanoswitches, it picks up the nanoswitches, which then intermix with the urine. The tube or channel may end at an opening in the gel film where the urine mixed with nanoswitches will collect before being electrophoretically pulled through the gel film inside the electrophoretic cell. The user may then place the biomarker detector cartridge in a base as described herein to apply a voltage across the electrophoretic cell and perform an electrophoretic separation at the gel film, which may be processed with a reader disposed at the base.

In another embodiment, a kit is provided that includes one or more biomarker detector cartridges and a base as disclosed herein.

BRIEF DESCRIPTION OF THE SEVERAL VIEWS OF THE DRAWINGS

The foregoing summary, as well as the following detailed description of embodiments of the gel electrophoresis diagnostic devices, kits, and methods disclosed herein, will be better understood when read in conjunction with the appended drawings of exemplary embodiments. It should be understood, however, that the invention is not limited to the precise arrangements and instrumentalities shown.

In the drawings:

FIG. 34 illustrates internal components of the exemplary biomarker detector cartridge of FIG. 31;

FIG. 35 illustrates internal components of the exemplary biomarker detector cartridge of FIG. 31;

FIG. 36 illustrates an exemplary biomarker detector cartridge as inserted in an exemplary base;

FIG. 37 illustrates internal components of the exemplary base of FIG. 36 with the exemplary biomarker detector cartridge of FIG. 36;

DETAILED DESCRIPTION OF THE INVENTION

Figure 1:
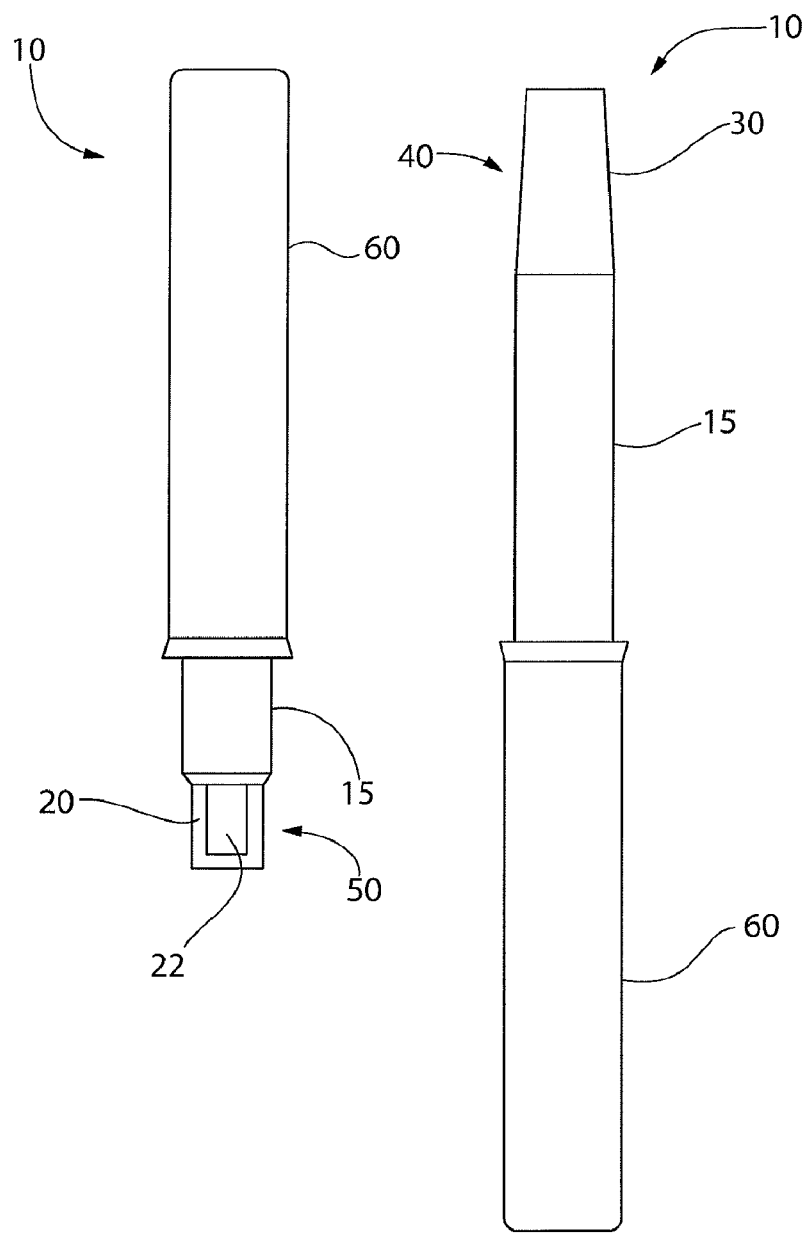
FIG. 1 illustrates two arrangements of a capped biomarker detector cartridge.

Referring to the drawings, wherein like reference numerals indicate like elements throughout, a general biomarker detector cartridge is shown in FIG. 1.

The devices described herein allow for in-home testing of disease or conception associated biomarkers with disposable biomarker detector cartridges. In some aspects, the devices described herein enable a user to test a sample of bodily fluid with a biomarker detector cartridge using electrophoresis in conjunction with a base that can process the cartridge. To do this, the devices, and methods of using the same, require rudimentary sample preparation, which minimizes the user's contact with their own bodily fluids, while eliminating the need for expensive and complicated laboratory equipment. Equipped with the devices described herein, a user may collect a sample with the sample portion of a biomarker detector cartridge by urinating on the sample portion or otherwise contacting the sample portion with the bodily fluid. The user may then deposit the biomarker detector cartridge at a base that is designed to receive the biomarker detector cartridge. The base may then communicate with an electrophoretic cell inside the biomarker detector cartridge that can be loaded with a combination of the sample and nanoswitches from a nanoswitch source inside the biomarker detector cartridge. Inside the biomarker detector cartridge an electrophoresis experiment is performed with the aid of the nanoswitches in order to separate and elucidate specific biomarkers for disease or conception. With the aid of the devices described herein, a user may be provided with access to clinical tests that might ordinarily take days or weeks to process at a hospital or clinic.

The biomarker detector cartridge 10 may include a cartridge body 15 having a sample portion 40 and an assay portion 50. The sample portion 40 may include a fluid collector 30 that may be used to collect a bodily fluid. The assay portion 50 may include an electrophoretic cell 20, which may include a separation medium 22. In some embodiments, the assay portion 50 may include an optical filter, as described herein, which may be placed over and/or under the electrophoretic cell 20. The sample portion 40 may be fluidly coupled or may provide for fluid communication to the assay portion 50, through the cartridge body 15, such that bodily fluid collected at the fluid collector 30 may be transferred or otherwise directed to the assay portion 50 and, more particularly, may be transferred to the electrophoretic cell 20 for analysis.

In some embodiments, the fluid collector 30 includes a sponge, foam, or membrane, such as a polyurethane sponge or foam, or another adsorbent and/or absorbent material. In some embodiments, the fluid collector 30 may include a cellulose, nitro-cellulose, and/or polyvinyl difluoride (PVDF) membrane, sponge, or foam. In some embodiments, the fluid collector 30 is a Porex adsorbent, which may be PE/PET based. In some embodiments, the Porex absorbent may include Porex conjugate release layer that may be sintered PE based. In some embodiments, the fluid collector 30 may include a matrix, such as a hydroxyapetite matrix, which may be disposed in or about the absorbent and/or adsorbent material. Such a matrix may help to remove any endogenous DNA from bodily fluid collected therein (e.g., urine). In some embodiments, a hydroxyapatite matrix may be positioned between the fluid collector 30 and a fluid channel that may be provided to fluidly couple (or otherwise provide fluid communication) the fluid collector 30 and the electrophoretic cell 20 in the assay portion 50. The fluid collector 30 may have a fixed width or may be tapered to allow the cap 60 to be more easily placed over the sample portion 40. In some embodiments, the fluid collector 30 may include one or more release layers, where such release layers may be glass-fiber and/or sintered polyethylene based. The release layer may be used to provide a dry reagent on or at the fluid collector 30. In some embodiments, the release layer may be a conjugate release layer that may have a low affinity for a reagent disposed on the fluid collector 30 so that the release layer may be released upon wetting. In some embodiments, detergents and/or blocking agents may be included in a release layer that may be released upon wetting.

In some embodiments, the fluid collector 30 may include a distal portion that has a tapered shape, a rectangular shape, an ovular shape, a circular shape, a fan shape, a triangular shape, a trapezoidal shape, and/or a spoon shape. In some embodiments, the fluid collector 30 may be fluted or non-fluted. In some embodiments, the biomarker detector cartridge 10 may include a slide or cover that may allow the fluid collector 30 to be extended and/or retracted as needed. For example, a slide may be used to cover the fluid collector 30, wherein the fluid collector includes a fluted fan shape, and then the fluid collector 30 may be extended from within the slide and the fluted fan shaped fluid collector may transition from a contracted or closed state (within the slide) to an expanded or open state (slide removed or withdrawn) and the fluid collector 30 may then be used to collect a bodily fluid as described herein.

The fluid collector 30 may include a coating that allows for better adsorption or absorption of bodily fluids or may allow for the adsorption of fluids without the retention of protein biomarkers that may be distributed therein. In some embodiments, the coating may be a coating for non-protein binding or a coating that prevents protein binding. In some embodiments, the coating may be applied to the fluid collector 30 by freeze drying (e.g., freeze drying a coating for non-protein binding onto a surface of the fluid collector 30).

The biomarker detector cartridge 10 may include a reagent source, such as a source of nanoswitches (as shown, for example, in FIGS. 2, 3, 6, 8, 10, and 14), which may be used to bind a biomarker that may be present in bodily fluid collected at the fluid collector 30. The source of nanoswitches may be disposed at the sample portion 40, a fluid channel or pathway within the cartridge body 15 that may connect the sample portion 40 and the assay portion 50, and/or the electrophoretic cell 20. For example, where the source of nanoswitches is disposed at the sample portion 40, the source may be on a surface of the sample portion 40 (e.g., a surface of the fluid collector 30) or within the sample portion 40 (e.g., within the fluid collector 30). Accordingly, when a bodily fluid is collected at the fluid collector 30, the source of nanoswitches may be positioned in the biomarker detector cartridge 10 such that bodily fluid collected will contact the source of nanoswitches. The source of nanoswitches may then release nanoswitches, which may include one or more types of nanoswitches, into the bodily fluid and may be free to bind one or more biomarkers disposed within the bodily fluid, which may be indicative of one or more biological events. For example, the source of nanoswitches may release two or more specific nanoswitches, or pluralities of nanoswitches, that may bind two or more biomarkers for different biological events.

The biomarker detector cartridge 10 may include a colorimetric strip disposed in biomarker detector cartridge 10, which may be fluidly coupled or otherwise in fluid communication with the fluid collector 30 that may be used to indicate the concentration of bodily fluid (e.g., the concentration of urine to determine the hydration level of a patient and/or allow for the normalization of biomarker counts so that assay results may be quantified).

As used herein, the term "bodily fluid" may refer to any fluid that can be isolated from the body of an individual and includes, but is not limited to whole blood, plasma, serum, bile, saliva, urine, tears, perspiration, cerebrospinal fluid (CSF), semen, swabbed samples, mucus, sputum, menstrual blood, menstrual fluid, vaginal mucus, and the like. In some embodiments, bodily fluid may more particularly refer to whole blood, serum, urine, saliva, swabbed samples, mucus, or semen. In certain embodiments, bodily fluid may more particularly refer to whole blood, serum, urine, or saliva. In some embodiments, the bodily fluid may include a target molecule (e.g., a biomarker).

In some embodiments, the reagent source or nanoswitch source may be a portion of the biomarker detector cartridge 10 that includes a quantity of nanoswitches. In some embodiments, the nanoswitch source may include a sticker, a capsule, a pellet, or a residue. In some embodiments, the nanoswitch source may include a quantity of nanoswitches deposited as a residue at the fluid collector. In some embodiments, the nanoswitches may be provided, or maintained, in the biomarker detector cartridge 10 as dry nanoswitches. Therefore, in some embodiments, the nanoswitches described herein may be separated from wet materials that may be disposed within the biomarker detector cartridge 10 (e.g., the separation medium 22 may be kept wet or saturated with a fluid). For example, the nanoswitches described herein may be kept dry by covering the nanoswitches with a barrier, such as an impermeable and/or pierceable barrier that may prevent premature wetting of the nanoswitches, but may be broken, pierced, torn, or removed to allow liquid to flow over or otherwise contact the nanoswitches as described herein. The barrier may be a foil barrier.

As used herein, the term "nanoswitches" refers to oligonucleotides that are functionalized with interacting molecules such that the nanoswitches may report molecular associations and dissociations between a target molecule and the interacting molecules through topicological changes in the oligonucleotides where reporting may be observed through electrophoretic analysis. In some embodiments, the nanoswitches include compositions having a switchable single-molecule linker comprised of two members of a binding pair, such as a receptor and a ligand, integrated onto a nucleic acid (e.g., DNA backbone). In some embodiments, the nanoswitches are DNA nanoswitches where DNA oligonucleotides are functionalized with two or more interacting molecules and hybridized to certain locations on an ssDNA scaffold. Association and dissociation of a target molecule with the nanoswitches may result in two distinct topological states that may be observed through electrophoretic analysis such that the bound nanoswitch may be readily distinguished from the unbound nanoswitch. In some embodiments, the nanoswitches may be about 7,249 bp in length (e.g., about 2.4 µm). Moreover, antibodies that may be configured to bind a biomarker as disclosed herein may be placed on the DNA backbone at about 200 nm apart. The binding partners of two such antibodies may be placed as far as about 2.4 µm away from each other and as close as about 20 nm away from each other. In some embodiments, nanoswitches may be characterized by any method understood by persons having ordinary skill in the art for determining oligonucleotide identity and may include, for example, a gel shift assay in a polyacrylamide gel to test the functionality of the oligonucleotides after conjugation. In some embodiments, the nanoswitches may characterized by hybridizing them onto a scaffold and determining if any loops in the structure are formed.

In certain embodiments, binding of a target molecule induces a loop within a long filament (about 7 kb) of double-stranded DNA, changing its electrophoretic mobility. While gel electrophoresis may not be generally considered a sensitive and precise analysis platform, the addition of nanoswitches (e.g., DNA nanoswitches) effectively converts standard electrophoresis into a sensitive and precise analytical method. This is accomplished by: (1) creating unambiguous "digital" on and off signals dictated solely by the properties of the nanoswitch rather than the target molecule; and (2) imparting a linearly amplified signal where each captured target molecule results in the movement of thousands of dye molecules. In practice, these properties mean that a binary nanoswitch (e.g., a DNA nanoswitch) may only provide two bands in an separation medium in predictable locations and that the brightness of the "on" band can be quantitatively related to the number of molecules detected with a sensitivity of at least about 1000 fold greater than a Forster Resonance Energy Transfer (FRET) pair or molecular beacon, for example.

In some embodiments, the interacting molecules may include molecules that bind to a target molecule through disulfide bond formation, receptor-ligand interaction, antigen-antibody interaction, oligonucleotide formation, peptide bond formation, and/or restriction enzyme interaction. In some embodiments, the interacting molecules may be biomarkers.

In some embodiments, the reagent source may include a negative control to provide a negative control lane in the separation medium to allow a user to compare background signal or a signal provided by the nanoswitches themselves without being bound to a biomarker or analyte. The negative control may be negative nanoswitches, which are nanoswitches that may not form a loop by, for example, where the nanoswitch only has one antibody, or has no antibodies, or has antibodies that do not bind to the analytes or biomarkers present in a urine sample). Alternatively, the negative control may include negative urine. In this alternative, the negative control may be provided to allow for the use of a person's urine, but without the analyte or biomarker of interest. For example, a negative control as a negative urine lane for an hCG test would require urine to pass through an excess of anti-hCG antibodies that would bind all, or substantially all, of the hCG in the urine sample that may be disposed at an applicator of the sample portion. This result may also be achieved by flooding the urine sample at the respective applicator with free-floating anti-hCG antibodies. With a negative urine control, all, or substantially all, of the hCG in the sample may be extracted (or in the flooding case, all the epitopes are blocked), at the respective applicator, so that there is no free hCG to bind nanoswitches and close the loop. This allows for analysis of any background and/or false signals that may be associated with the nanoswitches in the same urine sample tested in the various test lanes of the separation medium.

In some embodiments, the nanoswitches disclosed herein may include and/or may be prepared according to the disclosure in U.S. Published Patent Application No. 2014/

0255939, the entirety of which is incorporated herein by reference. In some embodiments, the nanoswitches disclosed herein may include and/or may be prepared according to the disclosure in U.S. Published Patent Application No. 2016/0279257 and International Patent Application Publication No. WO 2015/006626, the entireties of which are incorporated herein by reference.

In some embodiments, the biomarker described herein may be a biomarker for a biological event. In some embodiments, the biological events may include a disease event (i.e., disease biomarker), an inflammation event (i.e., an inflammation biomarker), a reproduction event (i.e., a reproduction biomarker), and/or an aging event (i.e., an aging biomarker).

Disease biomarkers may include one or more disease biomarkers related to or associated with the onset of disease, the offset of disease, and/or the presence of a disease state in a patient. Disease biomarkers may include one or more of a viral biomarker, a bacterial biomarker, a cancer biomarker, or a symptom biomarker. Viral biomarkers may include, but are not limited to biomarkers for common cold (e.g. rhinovirus), influenza, herpes, Zika, and/or HIV. In some embodiments, viral biomarkers may include one or more rhinovirus proteins, one or more influenza A/B/C proteins, one or more HSF-1/2 proteins, and/or one or more HIV virus proteins. Bacterial biomarkers may include, but are not limited to, biomarkers for strep throat, biomarkers for *chlamydia*, and/or biomarkers for gonorrhea. In some embodiments, bacterial biomarkers may include, but are not limited to, one or more *streptococcus* proteins, one or more *Chlamydia trachomatis* proteins, and/or one or more *Neisseria gonorrhoeae* proteins. Symptom biomarkers may include, but are not limited to, biomarkers for coughing, wheezing, runny nose, nausea, cramps, tightness of the chest, light-headedness, sore throat, and/or chest pain. Disease biomarkers may also include, but are not limited to, biomarkers for cardiac distress and/or diabetes. In some embodiments, disease biomarkers may include troponin, CRP, and/or ha1c.

Cancer biomarkers may include biomarkers for breast cancer, colorectal cancer, gastric cancer, GIST, leukemia/lymphoma, lung cancer, melanoma, and or pancreatic cancer. In some embodiments, breast cancer biomarkers may include one or more of ER/PR and HER-2/neu. In some embodiments, colorectal cancer biomarkers may include one or more of EGFR, KRAS, and UGT1A1. In some embodiments, gastric cancer biomarkers may include HER-2/neu. In some embodiments GIST biomarkers may include c-KIT. In some embodiments, leukemia/lymphoma biomarkers may include one or more of CD20 antigen, CD30, FIP1L1-PDGRFalpha, PDGFR, PML/RAR alpha, TPMT, and UGT1A1. In some embodiments, lung cancer biomarkers may include one or more of ALK, EGFR, and KRAS. In some embodiments melanoma biomarkers may include BRAF.

Inflammatory biomarkers, which may include anti-inflammatory biomarkers, may include one or more inflammatory biomarkers described in U.S. Patent Application Publication No. 2010/0275282, the entirety of which is incorporated herein by reference.

Reproduction biomarkers may include biomarkers for ovulation, fertilization, implantation, and/or embryo development. In some embodiments, ovulation biomarkers may include luteinizing hormone (LH). In some embodiments, fertilization biomarkers may include early pregnancy factor (EPF) and/or pre implantation factor. In some embodiments, implantation biomarkers may include β-human Chorionic Gonadotropin (β-hCG) and/or hyperglycosylated hCG. In some embodiments, embryo development biomarkers may include β-hCG.

Aging biomarkers or age-related biomarkers include one or more biomarkers described in U.S. Patent Application Publication No. 2008/0124752, the entirety of which is incorporated herein by reference.

In some embodiments, an electrophoretic cell (e.g., electrophoretic cell 20) refers to a container or platform that includes a separation medium (e.g., separation medium 22) in which electrophoretic separation may be contained. In some embodiments, the electrophoretic cells described herein may include electrical contacts or, for example, two or more electrical contacts. In some embodiments, a first electrical contact may be placed at one end of the electrophoretic cell in electrical communication with a separation medium deposited therein and a second electrical contact may be placed at another end of the electrophoretic cell in electrical communication with the separation medium. In some embodiments, a power source may be coupled to the electrical contacts (e.g., first and second electrical contacts) to thereby apply an electrical potential across the electrophoretic cell 20 and the separation medium 22. In some embodiments, the electrical communication may only be provided when a bodily fluid has been received at the electrophoretic cell 20, which may allow for any electrodes disposed at the electrophoretic cell 20 to be kept dry and eliminate corrosion of the electrodes. In some embodiments, a power source may be provided within the biomarker detector cartridge and/or within the base, as described herein.

As used herein, the term "separation medium" or "separation media" may refer to a gel or liquid medium through which polynucleotides or oligonucleotides may be electrophoresed and which may allow for the electrophoretic separation of two or more polynucleotides and/or oligonucleotides. For example, the separation of biomarker-bound nanoswitches (e.g., a "looped" nanoswitch state) and unbound nanoswitches (e.g., an "unlooped" nanoswitch state). In some embodiments, separation media may include a viscous fluid (e.g., a viscous solution) or a gel. In some embodiments, the gel may include an agarose gel, a polyacrylamide gel, a starch gel, or a combination thereof. In some embodiments, the viscous fluid may include sucrose, polyethylene glycol (PEG), glycerol, and/or ficoll. In some embodiments, the separation medium 22 may be provided, or maintained, in a moist or wet state within the biomarker detector cartridge 10.

In some embodiments, the separation medium (e.g., separation medium 22) may include a stain (or dye) that may be used to visualize one or more reagents, such as nanoswitches, that may be separated in the separation medium. In some embodiments, the stain (or dye) may bind one or more of a target molecule (e.g., the biomarker), a target molecule bound to a nanoswitch, a nanoswitch bound to a target molecule, and an unbound nanoswitch. In some embodiments, the stain may include any nucleic acid or nucleotide dye known in the art. In some embodiments, the stain may include any intercalating dye, non-intercalating dye, and/or other suitable nucleic acid dyes such as dsDNA-selective or RNA-selective dyes. In some embodiments, the stain may include one or more of ethidium bromide, actinomycin D, psoralen, 4'-aminomethyl-4,5',8-trimethylpsoralen (AMT), Hoechst 33258, EvaGreen dye, GelRed, GelGreen, SYBR Green I, SYBR Green II, OliGreen, RiboGreen SYBR GreenEr, SYBR Gold, SYBR Safe, gel red, LC Green, LC Green Plus, BOXTO, BEBO, SYBR DX, SYTO9, SYTOX Blue, SYTOX Green, SYTOX Orange, SYTO dyes, POPO-1, POPO-3, BOBO-1, BOBO-3, YOYO-1, YOYO-3, TOTO-1, TOTO-3, PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5, Ethidium Homodimer-1, Ethidium Homodimer-2, Ethidium Homodimer-3, propidium iodide, various Hoechst dyes, DAPI, ResoLight, Chromofy, and acridine homodimer.

In some embodiments, the nanoswitches used in the invention may include a nanoparticle tracer that may be used to visualize the nanoswitches during separation in the separation medium. In some embodiments, the nanoparticle tracer may be a quantum dot, which may be bound to the nanoswitches described herein. Accordingly, stains or dyes may not be required in the separation medium where nanoswitches are functionalized with quantum dots. As used herein, "quantum dot" may refer to a semiconductor whose excitations are confined in three spatial dimensions. As a result, they have properties that are between those of bulk semiconductors and those of discrete molecules. Examples of quantum dots include small regions of one material buried in another with a larger band gap, such as core-shell structures, e.g., with CdSe in the core and ZnS in the shell or from special forms of silica called ormosil, further examples include cadmium sulphide quantum dots, (CdTe quantum dots), quantum dot (QD) nanocrystals (ZnS, CdS, and PbS), cadmium sulfide quantum dots (CdS QDs), and the like. A quantum dot may emit fluorescent light. A quantum dot may be capable of providing an electrochemical signal.

In some embodiments, the biomarker detector cartridge (e.g., biomarker detector cartridge 10) may include a cap 60 that may be placed over the sample portion 40 and/or the assay portion 50 to convert the cartridge from an initial configuration to an in-use configuration. In some embodiments, the cap 60 may be placed over the assay portion 50 to protect the electrophoretic cell 20 and provide a user with handle during collection of bodily fluids at the fluid collector 30. In some embodiments, the cap 60 may be placed over the sample portion 40 to, for example, provide a clean surface to hold the biomarker detector cartridge 10 after bodily fluids have been collected at the fluid collector 30. Moreover, where the cap 60 is placed over the fluid collector 30, the force of applying the cap 60 over the fluid collector 30 may provide a force that compresses the fluid collector 30 and forces any bodily fluids from fluid collector 30 to the electrophoretic cell 20. In some embodiments, the cap 60 may be connected to the biomarker detector cartridge 10 to first cover the sample portion 40. The cap 60 may then be removed from the sample portion 40 to cover the assay portion 50 (or, alternatively, an end of the biomarker detector cartridge 10 that is opposite from the sample portion of the cartridge) and thereby act as an extension, which may be grasped by a user as provided herein. In some embodiments, the cap 60 may include a flared opening so as to be more easily placed over an end or portion of the biomarker detector cartridge 10. As shown in FIG. 1, the cap 60 may be a sleeve that may have a length of about ⁵⁄₉ths the length of the entire biomarker detector cartridge. This may allow for the cap 60 to provide a near doubling in length of the biomarker detector cartridge 10 when affixed to the end opposite the sample portion. In some embodiments, the biomarker detector cartridge is about 5 to 7 inches long and the cap 60 may be about 4 to 6 inches long. In some embodiments, the cap 60 may include a seal about its opening that may abut a surface of the biomarker detector cartridge 10 and thereby seal an end of the biomarker detector cartridge 10. For example, the cap 60 may be placed over the sample portion 40 after collection to prevent urine from dripping down the side of the biomarker detector cartridge 10. In some embodiments, the cap 60 may include a translucent material and may provide a light pipe so that when the biomarker detector cartridge 10 is inserted at the base, as described herein, a light source at the base may transfer light through the cap 60 where such light may be pulsed or may be solid to indicate a status of the base (e.g., running or completion of a test). In some embodiments, the cap 60 may be used to pump (i.e., move fluid about the interior of the biomarker detector cartridge 10) and thereby facilitate mixing of the collected bodily fluids within the biomarker detector cartridge 10. In some embodiments, the cap 60 may be coupled to the biomarker detector cartridge 10 to protect the assay portion 50 and, thereby, the electrophoretic cell 20.

In some embodiments, the cap 60 may serve as a sample collector into which a bodily fluid may be deposited. The fluid collector 30 may then be placed into the cap 60 to collect bodily fluid as described herein.

In some embodiments, the cap 60 and/or the biomarker detector cartridge 10 may include a handle.

Figure 2:
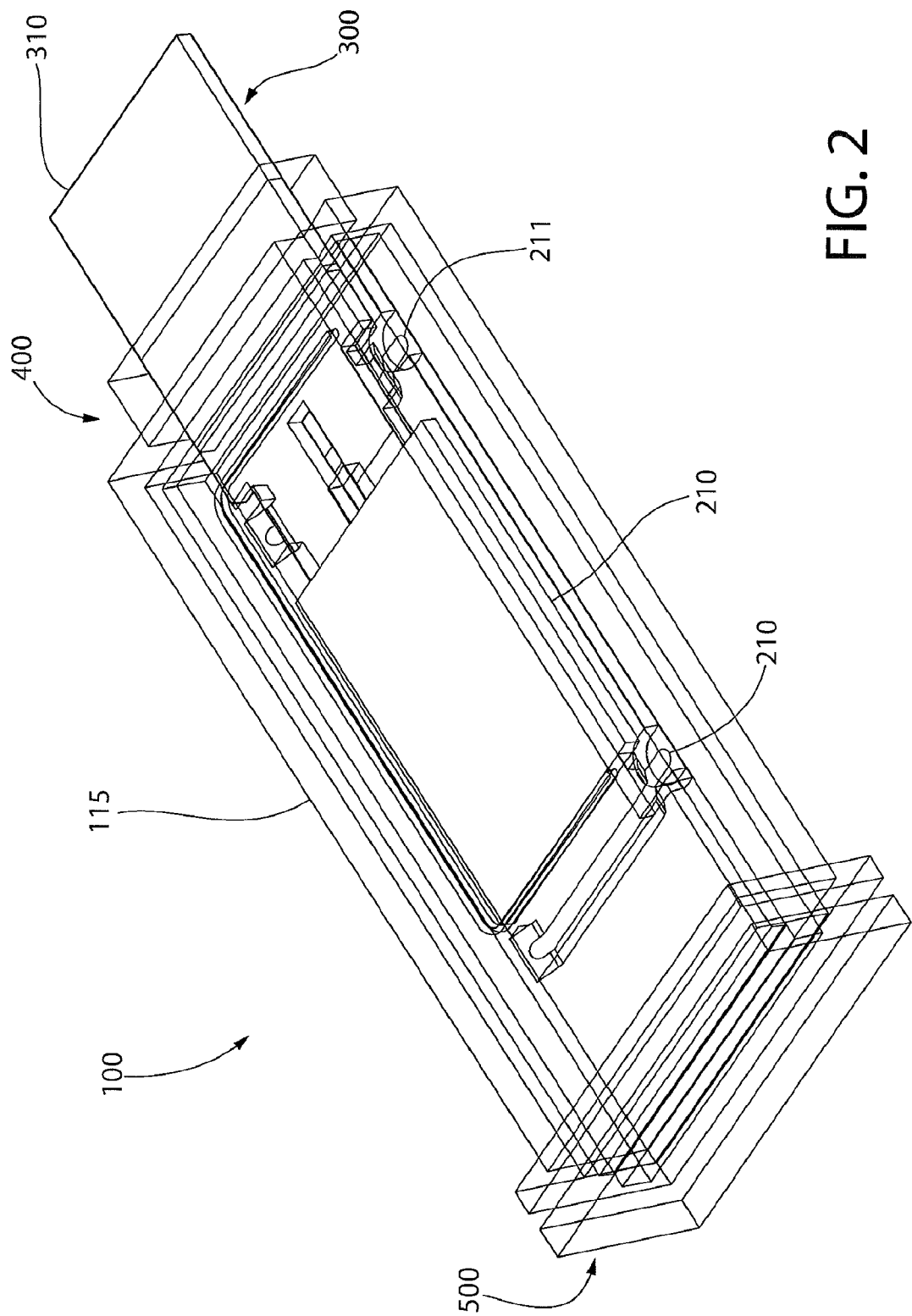
FIG. 2 is a perspective partially transparent view of a biomarker detector cartridge.

FIGS. 2 to 8 include a biomarker detector cartridge 100 that includes a sample portion 400 and an assay portion 500. As shown in FIG. 2, the assay portion 500 may be coupled to the sample portion 400. In some embodiments, the assay portion 500 may be connected to the sample portion 400 and received within at least a portion of the sample portion 400 as a cap that may cover and/or enclose the assay portion 500. In some embodiments, the assay portion 500 may be releasably coupled or otherwise releasably connected to the sample portion 400. In an embodiment, the sample portion 400 may include a cartridge body 115 that may cover and/or enclose the assay portion 500. In some embodiments, the assay portion 500 may be releasably coupled or otherwise releasably connected to the sample portion 400 by way of, for example, a snap fit engagement, press fit engagement, a friction fit engagement, or another releasable engagement method known to persons having ordinary skill in the art.

Figure 3:
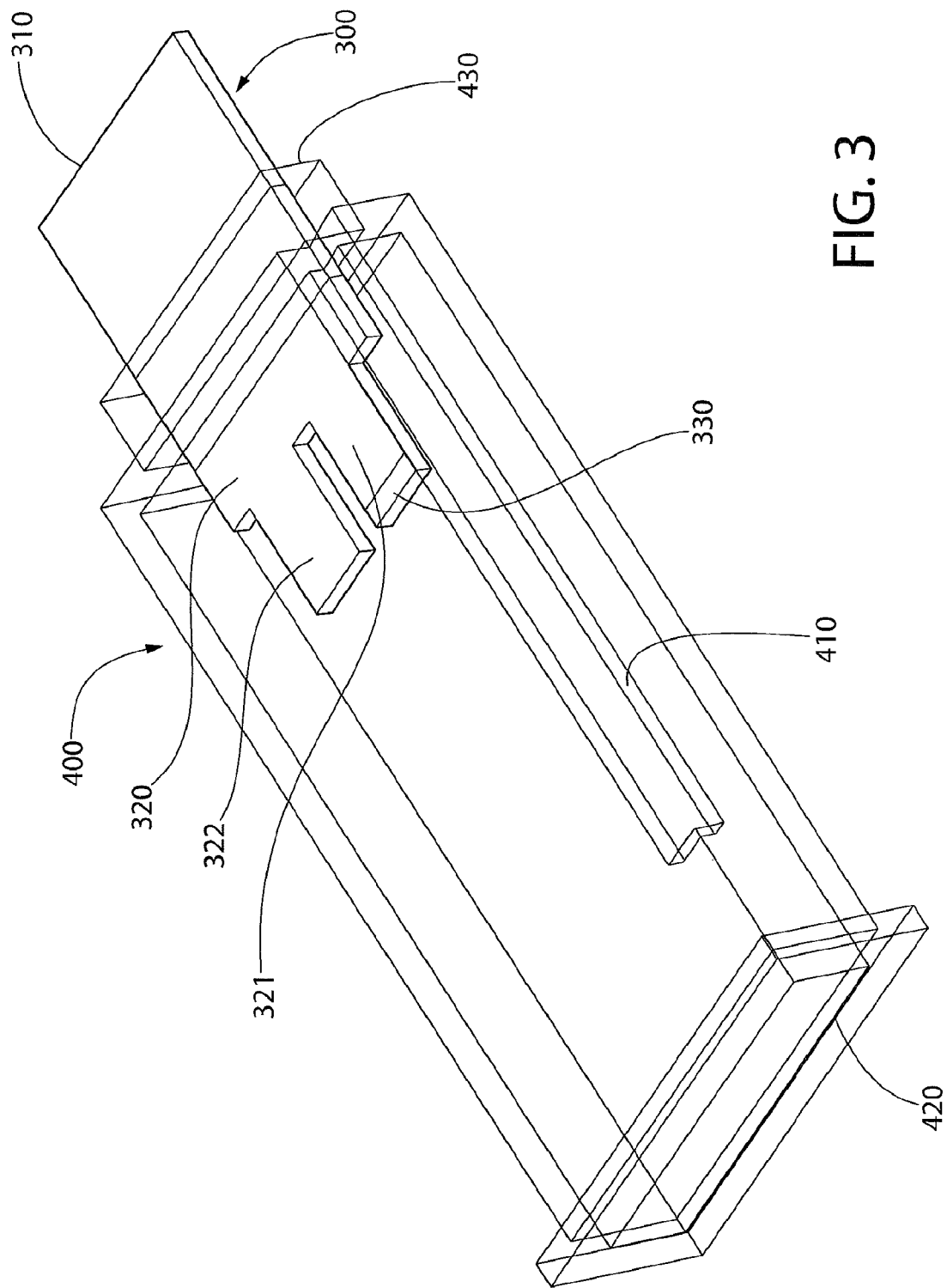
FIG. 3 is a perspective partially transparent view of the sample stick portion of the biomarker detector cartridge.

As shown in FIGS. 2 and 3, sample portion 400 may include a fluid collection portion 300 that may be disposed at one end of the sample portion 400. In some embodiments, the fluid collection portion 300 may include a fluid collector 310, such as a sponge, foam, or other adsorbent and/or absorbent materials, as described herein. In some embodiments, the sample portion 400 may be held and used to collect or soak up a bodily fluid that may be subject to collection. In some embodiments, a first part of the fluid collector 310 may be disposed exterior to the cartridge body 115 and a second part of the fluid collector 310 may be disposed interior to the cartridge body 115. For example, as shown in FIGS. 2 and 3, fluid collector 310 may extend from the interior of the cartridge body 115 to the exterior of the cartridge body 115 through an aperture 430. In some embodiments, a bodily fluid collected at the fluid collector 310 may pass from the first part of the fluid collector 310 to the second part of the fluid collector 310.

In some embodiments, the fluid collector 310 may include a transfer portion 320, which may or may not, be monolithic with the fluid collector 310. In some embodiments, the transfer portion 320 may include one or more applicators (e.g., applicators 321 and 322). In some embodiments, the applicators described herein may be projections of the fluid collector and may be monolithic with the fluid collector or may be separate material in fluid communication with the fluid collector. For example, the transfer portion 320 may include at least 1 applicator, or at least 2 applicators, or at least 3 applicators, or at least 4 applicators, or at least 5 applicators, or at least 6 applicators, or at least 7 applicators, or at least 8 applicators, or at least 9 applicators, or at least 10 applicators. As deployed herein, the transfer portion 320 may be in fluid communication with electrophoretic cell 200 and separation medium 220. In some embodiments, the transfer portion 320 may directly contact a surface of the separation medium 220. However, in some embodiments, either the sample portion 400 or assay portion 500 may include a channel or other fluid pathway to allow for fluid communication between the transfer portion 320 and the electrophoretic cell 200 and separation medium 220.

In some embodiments, the transfer portion 320 may not be monolithic to the fluid collector 310 and may thus be a separate structure disposed within the cartridge body 115 that may be coupled to a portion of the fluid collector 310 and in fluid communication with the fluid collector 310.

In some embodiments, each applicator (321, 322) disposed on the transfer portion 320 may represent a testing lane on the separation medium 220 at the electrophoretic cell 200. For example, applicator 321 and 322 may provide a bodily fluid portion to the separation medium 220 for electrophoretic separation at the separation medium 220. As shown in FIGS. 2 and 3, the transfer portion 320 may include a nanoswitch source 330. In some embodiments, the nanoswitch source 330 may be disposed at one of the applicators of the transfer portion 320 (e.g., applicator 321). In some embodiments, after a bodily fluid is collected at the fluid collector 310 the bodily fluid may travel to the transfer portion 320, and applicators thereon, for application to the separation medium 220. Where the transfer portion 320 includes a nanoswitch source 330, the bodily fluid collected at the fluid collector 310 may intermix with one or more nanoswitches of the nanoswitch source 330 and allow for such nanoswitches to contact and bind a biomarker in the bodily fluid.

With respect to FIGS. 2 and 3, an applicator 321, having a nanoswitch source 330 deposited thereat, may provide a mixture of the nanoswitches and the bodily fluid (having a biomarker) to the electrophoretic cell 200 and separation medium 220 to provide a first lane for analysis. In addition, an applicator 322, that does not include a nanoswitch source 330, may provide the bodily fluid alone to the electrophoretic cell 200 and separation medium 220 to provide a second lane for analysis and, for example, may function as a blank or control lane. In some embodiments, an applicator may be provided that applies unmixed nanoswitches to a separate lane at the separation medium 220 to provide a control of unbound nanoswitches (i.e., will not form loops upon mixing with a selected biomarker) and may provide a lane for background subtraction. In some embodiments, where the transfer portion 310 includes multiple applicators, it is understood that a variety of nanoswitch sources may be used with functionalized nanoswitches (which may be different or identical types of nanoswitches) at multiple applicators to either provide multiple runs of the same assay or provide a variety of different assays using one collection of bodily fluid at the fluid collector 310.

In some embodiments, the cartridge body 115 may include an aperture 420 that may be sized to receive the assay portion 500. In some embodiments, the cartridge body 115 may include one or more apertures 410 that may be sized to allow electrical contacts 210 and 211 of the electrophoretic cell, at the assay portion 500, to be accessed.

Figure 4:
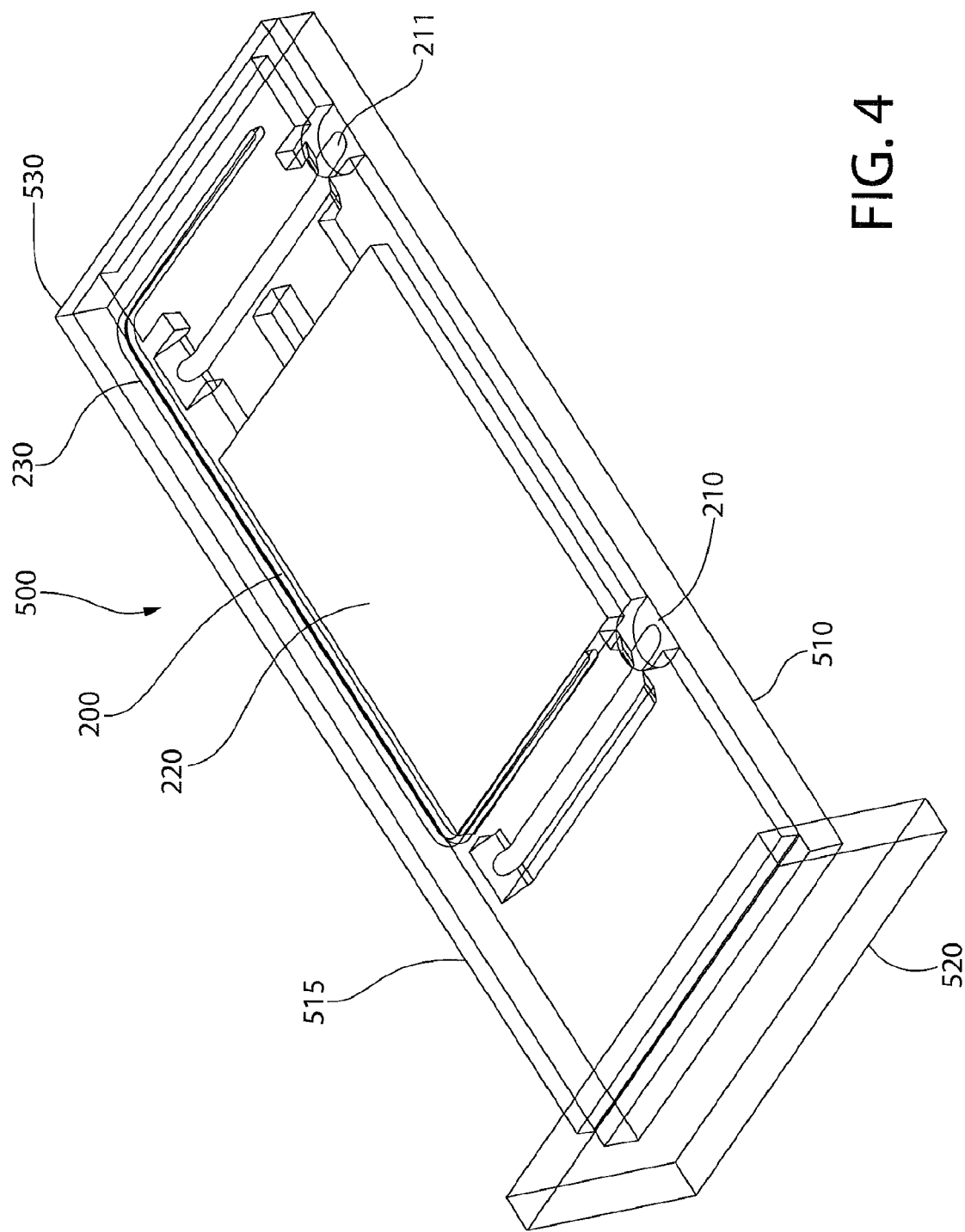
FIG. 4 is a perspective view of the assay portion of the biomarker detector cartridge.

As shown in FIGS. 2 and 4, an assay portion 500 includes a handle 520 and an insertion end 530. In some embodiments, the handle 520 may be used to hold the assay portion 500 and also may be used to insert the insertion end 530 of assay portion 500 into sample portion 400 at aperture 420. Assay portion 500 may include a platform holder 510 that may be coupled the handle 520. In some embodiments, the assay portion 500 may include an assay platform 515 that may be coupled to the platform holder 510. In some embodiments, one or more of the platform holder 510 and assay platform 515 may include a transparent polymeric material or glass. In some embodiments, the cartridge body 115 may include a transparent polymeric material or glass.

In some embodiments, the assay portion 500 may include an electrophoretic cell 200 that may be coupled to the assay platform 515. In some embodiments, the electrophoretic cell 200 may include a separation medium 220. In some embodiments, the electrophoretic cell 200 may include electrical contacts 210 and 211, which may be disposed at separate ends of the electrophoretic cell 200. In some embodiments, a first electrical contact 210 may contact a first portion of the separation medium 220, such that the first electrical contact 210 may be in electrical communication with the separation medium 220. In some embodiments, the second electrical contact 211 may contact a second portion of the separation medium 220, such that the second electrical contact 211 may be in electrical communication with the separation medium 220. In some embodiments, the second electrical contact 211 may contact the transfer portion 320 and/or one or more of the applicators disposed at the transfer portion 320 (e.g., applicators 321 and/or 322). In some embodiments, the first and/or second electrical contacts may be disposed in electrical communication with the separation medium 220 via one or more intermediate electrical conductors or hydratable materials (e.g., sponges or foams) that may become electrical conductors after being hydrated with a bodily fluid. For example, the transfer portion 320 may become an intermediate electrical conductor after receiving a bodily fluid. In some embodiments, the electrical contacts 210 and/or 211 may include printed electrodes, wires, or a combination thereof.

In some embodiments, additional electrical contacts may be provided to provide an orthogonal electrical field with respect to a first set of electrical contacts (e.g., electrical contacts 210 and 211). For example, the additional set of electrical contacts may provide an orthogonal electric field that may push the nanoswitches from one side of the separation medium 220 to the other, rather than merely along its length, to provide additional modes of separation.

In some embodiments, the assay portion 500 may include a capillary or channel 230 that may transfer a quantity of the bodily fluid collected at the fluid collection portion 300 to another portion of the electrophoretic cell 200. For example, capillary or channel 230 may transfer a quantity of the bodily fluid from the transfer portion 320 to a hydratable material that may be proximate to the separation medium 220. In another embodiment, capillary or channel 230 may transfer a quantity of the bodily fluid from the transfer portion 320 to a portion of the separation medium 220.

Figure 5:
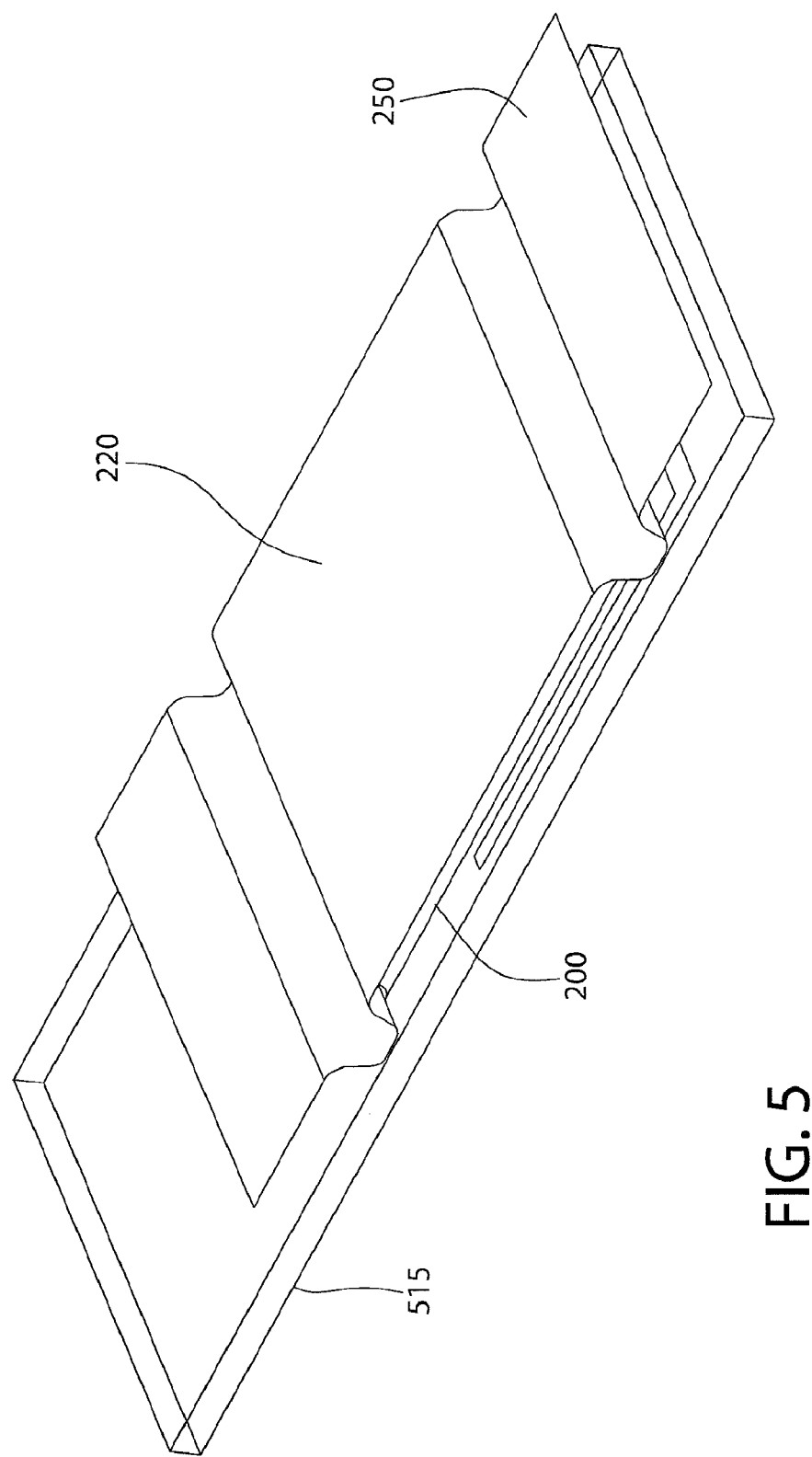
FIG. 5 is a perspective view of another embodiment of the assay portion of the biomarker detector cartridge that includes a removable barrier.

In an embodiment, the assay portion 500 may be separate from the sample portion 400 and may be separately sealed with a removable barrier 250 prior to use as shown in FIG. 5. In some embodiments, the removable barrier 250 is a heat sealed foil. A removable barrier 250 may be sealed about or to the electrophoretic cell 200 at the assay platform 515 to encapsulate and protect the separation medium 220. In some embodiments, the removable barriers described herein may include aluminum, tin, a polymeric material, and combinations thereof (e.g., a foil laminate material).

Figure 6:
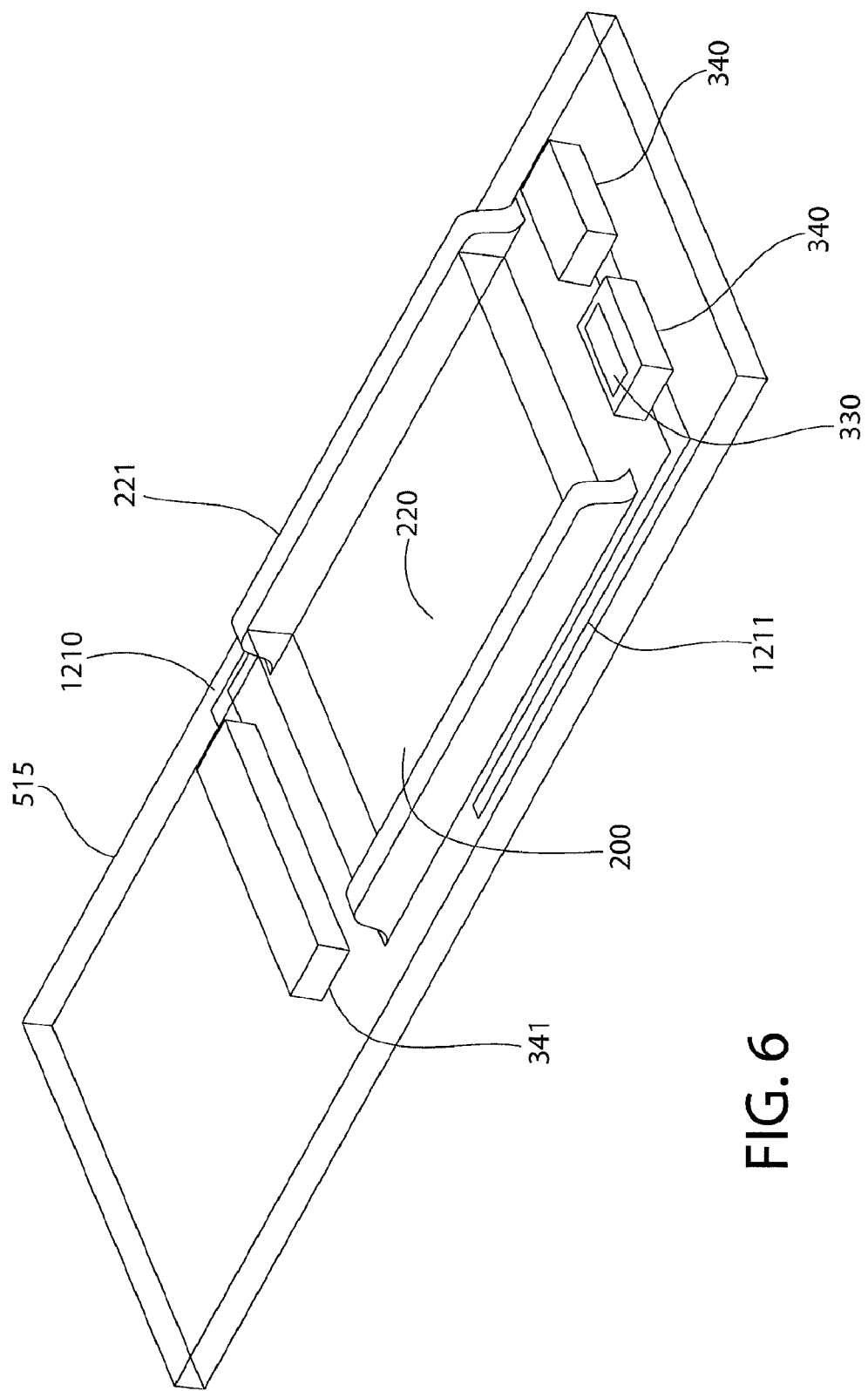
FIG. 6 is a perspective view of an assay portion, which may be used in conjunction with a biomarker detector cartridge shown in FIG. 2.
Figure 8:
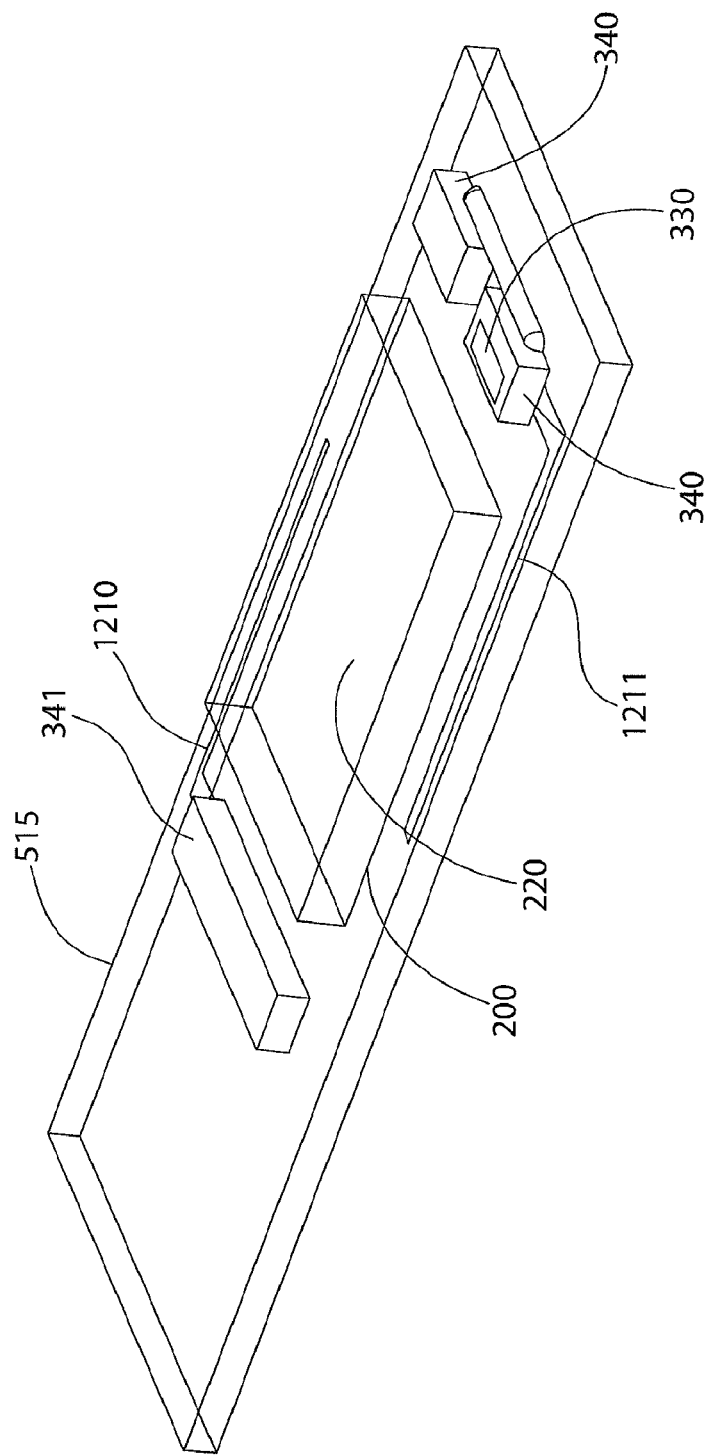
FIG. 8 is a perspective view of an assay portion that may be used in conjunction with a biomarker detector cartridge.

In another embodiment, as shown in FIG. 6, the electrophoretic cell 200 includes a separation medium holder 221 that may contain the separation medium 220 and may include one or more walls for seat sealing the separation medium 220. In some embodiments, the electrophoretic cell 200 may include one or more absorbent materials (e.g., hydratable materials) that may contact the transfer portion 320 and, in some embodiments, the applicators (e.g., applicators 321 and/or 322) included thereat. For example, the electrophoretic cell 200 may include adsorbent materials 340. In some embodiments, one or more of the adsorbent materials 340 may include a nanoswitch source 330. In some embodiments, an electrical conductor may be connected to adsorbent materials 340 such that the electrical conductor may be in electrical communication with the adsorbent materials 340. In some embodiments, the electrical contact 1211 may be coupled to one or more of adsorbent materials 340. In some embodiments, the electrophoretic cell 200 may include an adsorbent material 341 that may be coupled to an electrical contact 1210 and may be proximate to, and in electrical communication with, the separation medium 220. FIG. 8 illustrates the assay portion 400 in the absence of the separation medium holder 221, which may be an optional feature.

Figure 7:
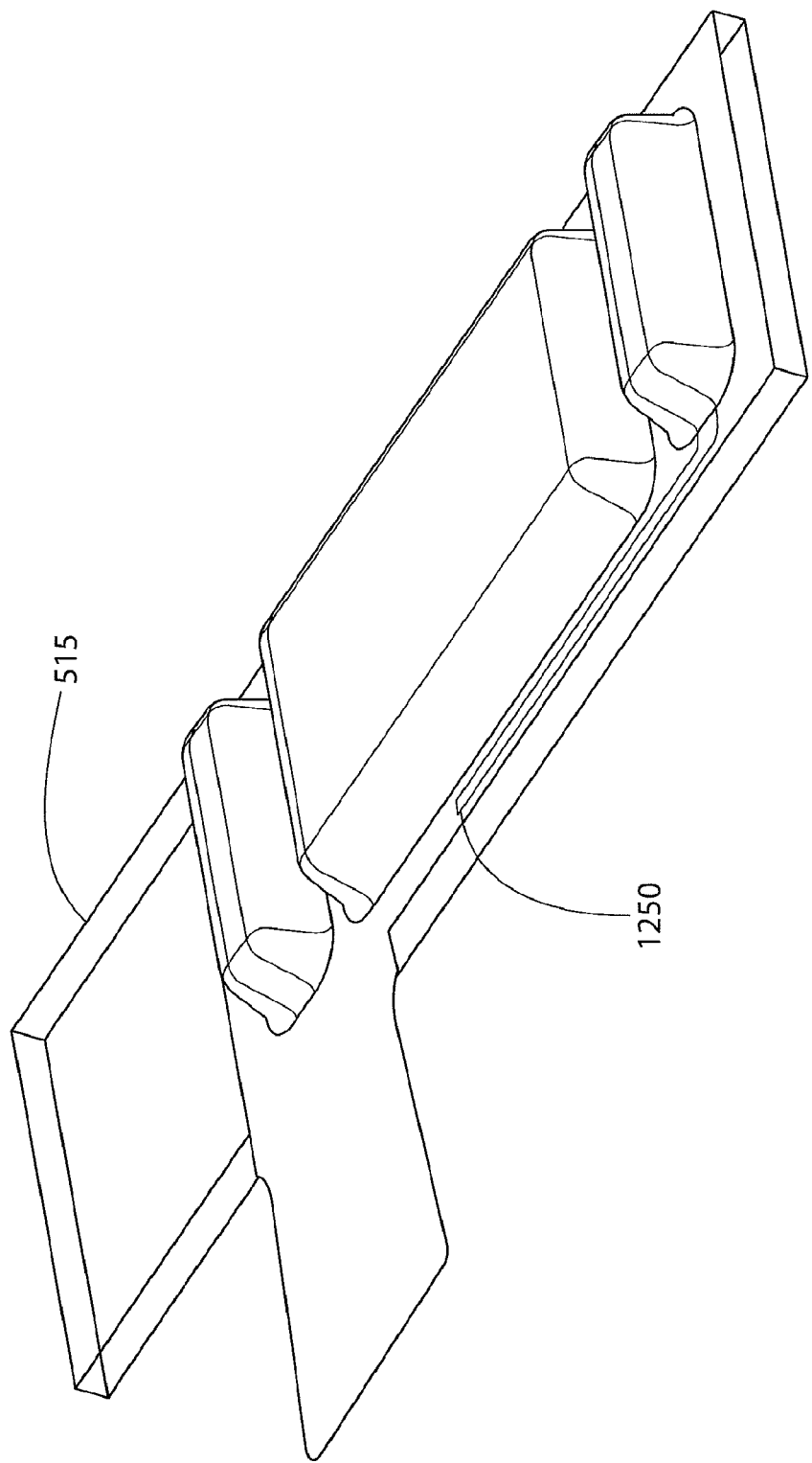
FIG. 7 is a perspective view of an assay portion that includes a removable cover.

In an embodiment, the assay portion 500 may be separate from the sample portion 400 and may be separately sealed with a removable cover such as a dome 1250 prior to use as shown in FIG. 7. A removable dome 1250 may be sealed about or to the electrophoretic cell 200 at the assay platform 515 to encapsulate and protect the separation medium 220.

FIGS. 9 to 16 include a biomarker detector cartridge 2000 that may include a sample portion 2400 and an assay portion 2500. In some embodiments, the sample portion 2400 and assay portion 2500 may be separate and may be combined prior to analysis after, for example, a bodily fluid sample has been collected at the sample portion 2400. In some embodiments, the assay portion 2500 may be releasably coupled or otherwise releasably connected to the sample portion 2400 by way of, for example, a snap fit engagement, press fit engagement, or a friction fit engagement. Accordingly, in some embodiments, the assay portion 2500 may be releasably coupled or otherwise releasably connected to the sample portion 2400. In some embodiments, the sample portion 2400 and the assay portion 2500 may be of unitary construction such that the sample portion and the assay portion are inseparable.

Figure 9:
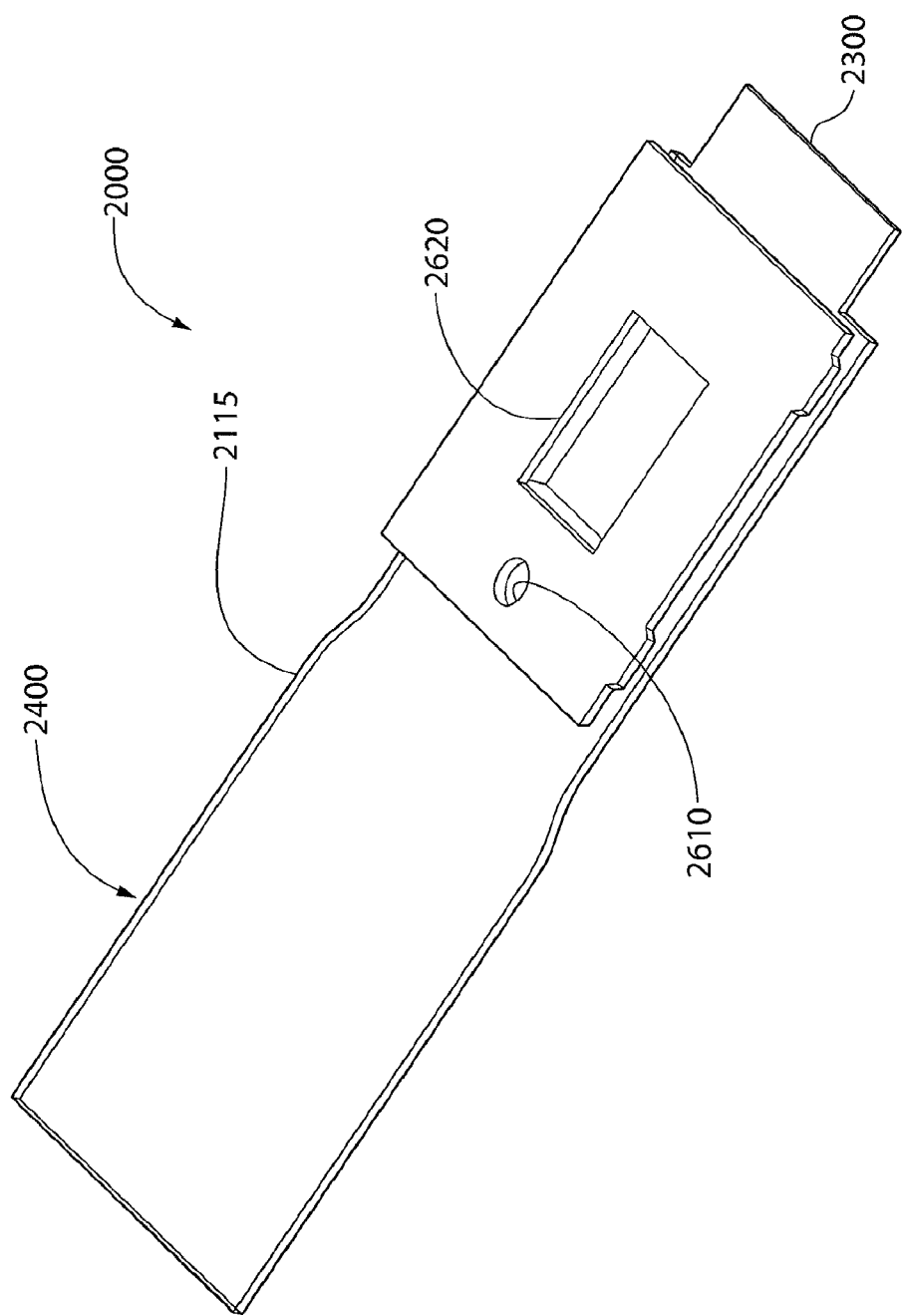
FIG. 9 is a perspective view of a biomarker detector cartridge.

As shown in FIG. 9, the biomarker detector cartridge 2000 may include a cover 2600 that may be disposed at the sample portion 2400 to cover the fluid collection portion 2300 and the assay portion 2500. In some embodiments, the cover 2600 may include an indicator window 2610 that allows for the view of a fluid collection indicator 2350 that may be disposed at or on a fluid collection portion 2300 that, when hydrated with a bodily fluid, will indicate that a selected amount of bodily fluid has been collected at the fluid collection portion 2300. In some embodiments, the indicator window 2610 may include a transparent polymeric material or glass. The selected amount of bodily fluid may be, for example, that amount of bodily fluid that is required to hydrate (or saturate with bodily fluid) the volume of the fluid collection portion 2300. In some embodiments, the cover 2600 may include an assay window 2620 that includes a transparent polymeric material or glass.

Figure 10:
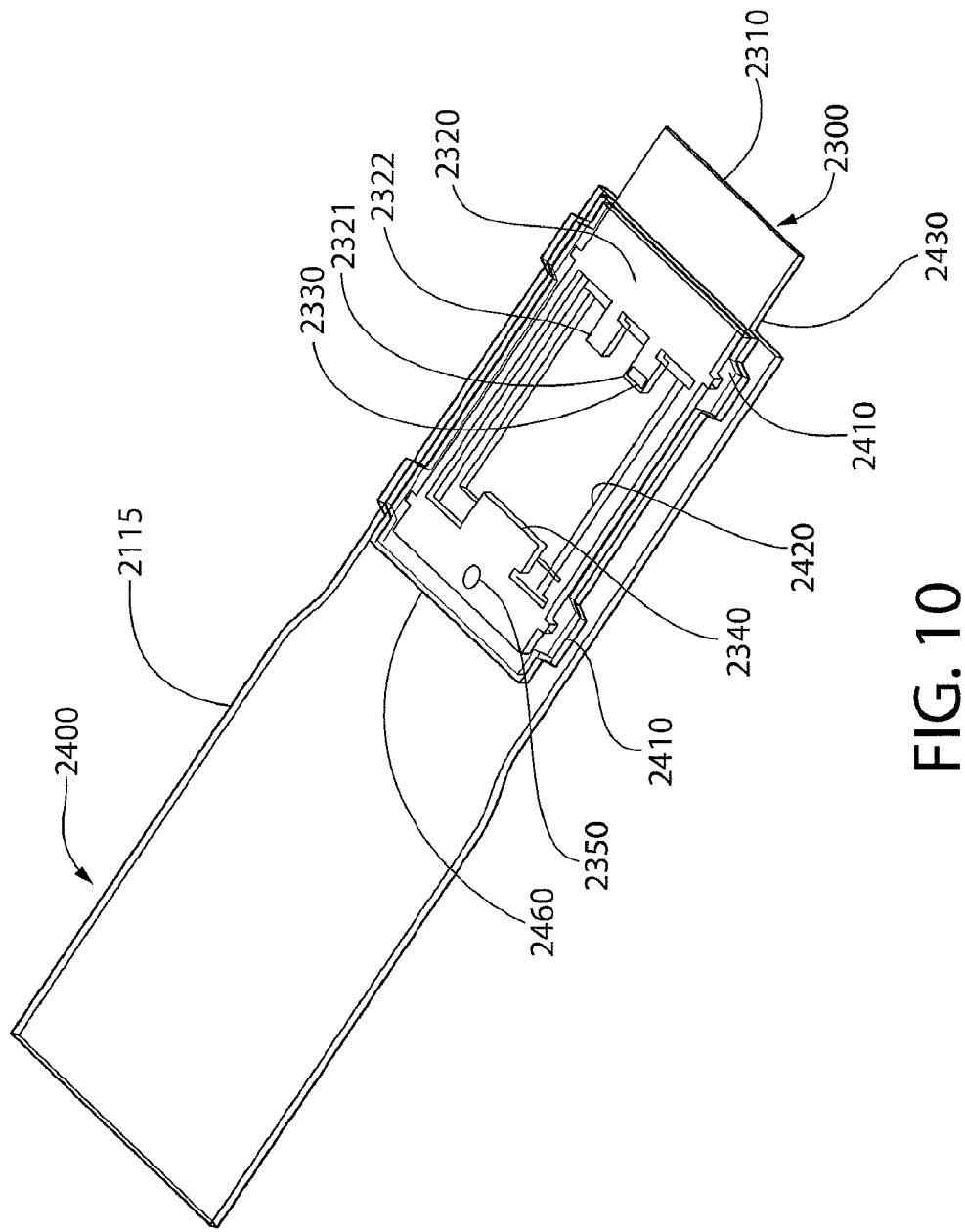
FIG. 10 is a perspective view of a sample portion of the biomarker detector cartridge.
Figure 12:
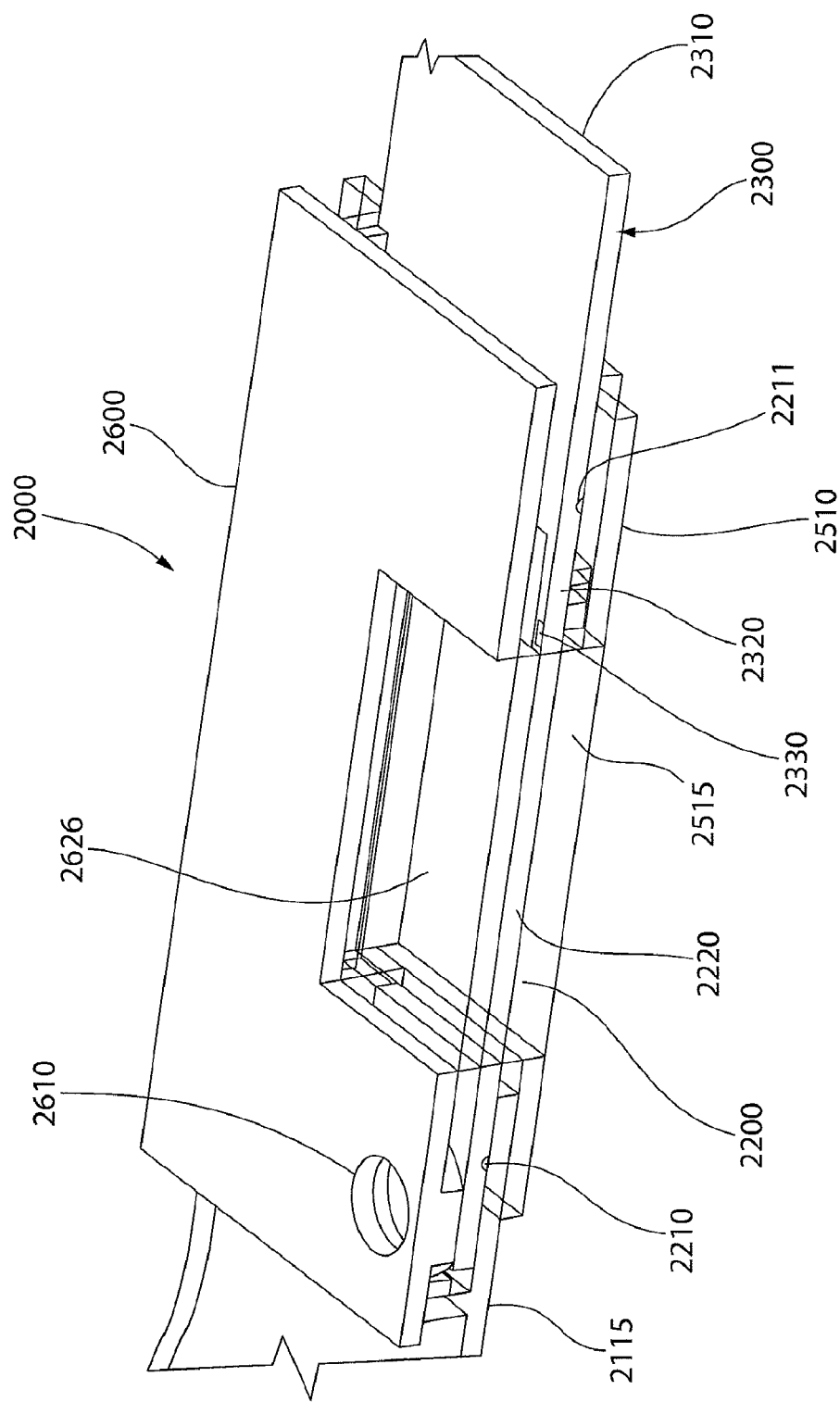
FIG. 12 is a cross section view of second embodiment of biomarker detector cartridge.

As shown in FIGS. 9 and 10, a sample portion 2400 may be provided that may include a cartridge body 2115. In some embodiments, the cartridge body 2115 may include a cover bracket 2460 that may connect to the cover 2600 and may provide a mount for the fluid collection portion 2300. In some embodiments, the sample portion 2400 may include a fluid collection portion 2300 that may be disposed at one end of the sample portion 2400. In some embodiments, the fluid collection portion 2300 may include a fluid collector 2310, such as a sponge or foam, as described herein. In some embodiments, the sample portion 2400 may be held and used to collect or soak up a bodily fluid that may be subject to collection. In some embodiments, a first part of the fluid collector 2310 may be disposed exterior to the cartridge body 2115 and a second part of the fluid collector 2310 may be disposed interior to the cartridge body 2115 and under the cover 2600. For example, as shown in FIGS. 10 and 12, may extend from the interior of the cartridge body 2115 to the exterior of the cartridge body 2115 through an aperture 2430. In some embodiments, a bodily fluid collected at the fluid collector 2310 may pass from the first part of the fluid collector 2310 to the second part of the fluid collector 2310.

In some embodiments, the fluid collection portion 2300 may include a contact portion 2340 that may contact a portion of the electrolytic cell 2200 and separation medium 2220.

Figure 11:
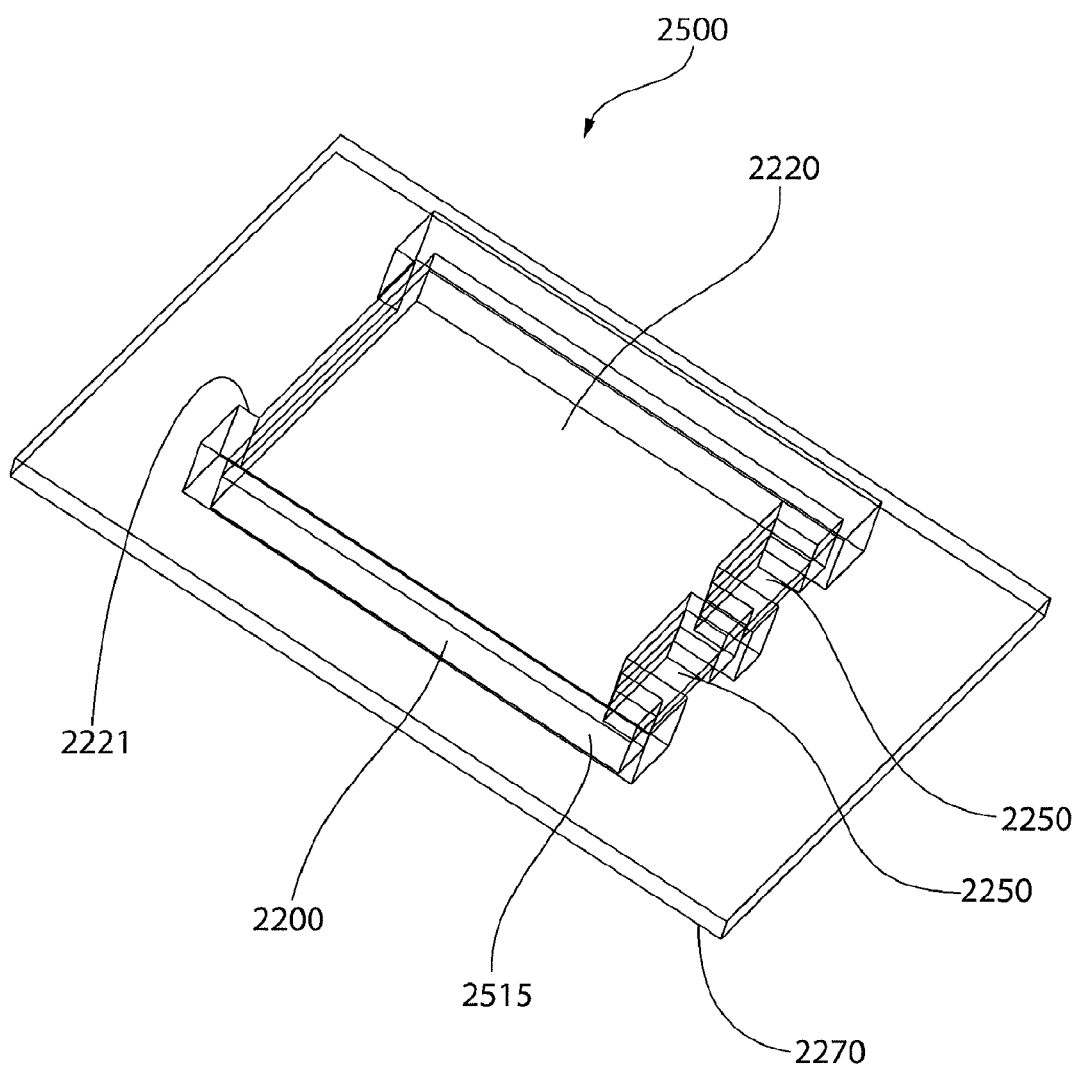
FIG. 11 is a perspective view of an assay portion of the biomarker detector cartridge.

In some embodiments, the fluid collector 2310 may include a transfer portion 2320, which may or may not, be monolithic with the fluid collector 2310. In some embodiments, the transfer portion 2320 may include one or more applicators (e.g., applicators 2321 and 2322). For example, the transfer portion 2320 may include at least 1 applicator, or at least 2 applicators, or at least 3 applicators, or at least 4 applicators, or at least 5 applicators, or at least 6 applicators, or at least 7 applicators, or at least 8 applicators, or at least 9 applicators, or at least 10 applicators. As deployed herein, the transfer portion may be in fluid communication with electrophoretic cell 2200 and separation medium 2220. In some embodiments, the transfer portion 2320 may directly contact a surface of the separation medium 2220. However, in some embodiments, either the sample portion 2400 or assay portion 2500 may include a channel or other fluid pathway to allow for fluid communication between the transfer portion 2320 and the electrophoretic cell 2200 and separation medium 2220. In some embodiments, one or more applicators (e.g., applicators 2321 and/or 2322) contact the electrophoretic cell 2200 and separation medium 2220 at transfer portion recesses 2250 that may be disposed at the electrophoretic cell 2200 and separation medium 2220, as shown in FIG. 11.

In some embodiments, the transfer portion 2320 may not be monolithic to the fluid collector 2310 and may thus be a separate structure disposed within the cartridge body 2115, under the cover 2600, that may be coupled to a portion of the fluid collector 2310 and in fluid communication with the fluid collector 2310.

In some embodiments, each applicator disposed on the transfer portion 2320 may represent a testing lane on the separation medium 2220 at the electrophoretic cell 2200. For example, applicator 2321 and 2322 may provide a bodily fluid portion to the separation medium 2220 for electrophoretic separation at the separation medium 2220. As shown in FIGS. 10 and 12, the transfer portion 2320 may include a nanoswitch source 330. In some embodiments, the nanoswitch source 330 may be disposed at one of the applicators of the transfer portion 320 (e.g., applicator 321). In some embodiments, after a bodily fluid is collected at the fluid collector 310 the bodily fluid may travel to the transfer portion 2320, and applicators thereon, for application to the separation medium 2220. Where the transfer portion 2320 includes a nanoswitch source 2330, the bodily fluid collected at the fluid collector 2310 may intermix with one or more nanoswitches of the nanoswitch source 2330 and allow for such nanoswitches to contact and bind a biomarker in the bodily fluid.

With respect to FIG. 10, an applicator 2321, having a nanoswitch source 2330 deposited thereat, may provide a mixture of the nanoswitches and the bodily fluid (having a biomarker or the absence thereof (i.e., a negative result)) to the electrophoretic cell 2200 and separation medium 2220 to provide a first lane for analysis. In addition, an applicator 2322, that does not include a nanoswitch source 2330, may provide the bodily fluid alone to the electrophoretic cell 2200 and separation medium 2220 to provide a second lane for analysis and, for example, may function as a blank or control lane. In some embodiments, where the transfer portion 2310 includes multiple applicators, it is understood that a variety of nanoswitch sources may be used with functionalized nanoswitches (which may be different or identical types of nanoswitches) or non-functionalized nanoswitches at multiple applicators to either provide multiple runs of the same assay or provide a variety of different assays using one collection of bodily fluid at the fluid collector 2310. In some embodiments, non-functionalized nanoswitches may be used to serve as a control and which may indicate that a bodily fluid is mixing with the nanoswitches and/or provide background subtraction data. Non-functionalized nanoswitches may, for example, be unable to form "loops" in their structure because they are not functionalized to bind a selected biomarker.

In some embodiments, the cartridge body 2115 may include an aperture 2420 that may be sized to receive the assay portion 2500. In some embodiments, the cartridge body 2115 may include one or more apertures 2410 that may be sized to allow electrical contacts 2210 and 2211, that may be disposed at the fluid collection source 2300, to be accessed.

As shown in FIG. 11, assay portion 2500 may include a platform holder 2510 that may be coupled to an assay platform 2515. In some embodiments, one or more of the platform holder 2510 and assay platform 2515 may include a transparent polymeric material or glass. In some embodiments, the cartridge body 115 may include a transparent polymeric material or glass.

In some embodiments, the assay portion 2500 may include an electrophoretic cell 2200 that may be coupled to the assay platform 2515. In some embodiments, the electrophoretic cell 2200 may include a separation medium 2220. In some embodiments, the electrophoretic cell 2200 and separation medium 2220 may include transfer portion receivers 2250 that may receive one or more applicators of the transfer portion 2320.

Figure 15:
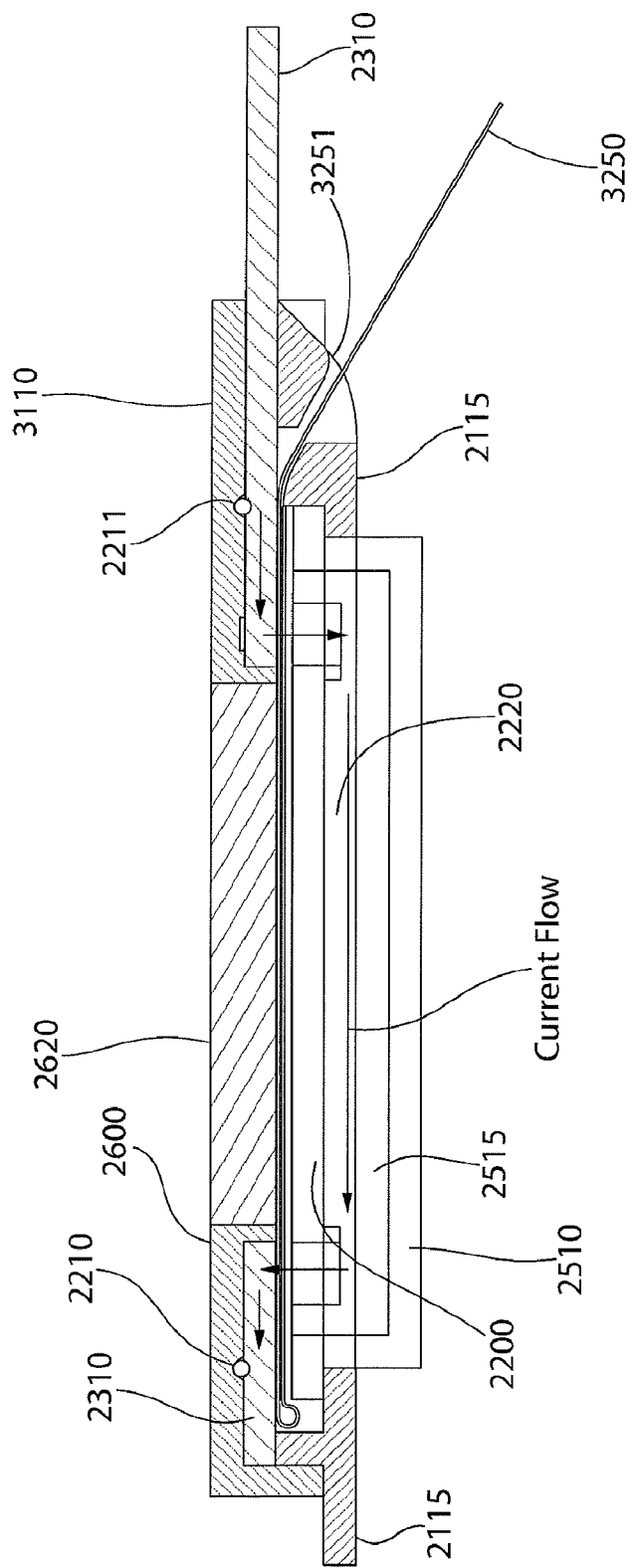
FIG. 15 is a cross section view of a variation on the biomarker detector cartridge shown in FIG. 9.

As shown in FIG. 12, in some embodiments, sample portion 2400 may include electrical contacts 2210 and 2211, which may be disposed at separate locations proximate to the fluid collection portion 2300. In some embodiments, a first electrical contact 2210 may contact a first portion of the fluid collector 2310, such that the first electrical contact 2210 may be in electrical communication with the separation medium 2220 through the contact portion 2340. In some embodiments, the second electrical contact 2211 may contact a second portion of the fluid collector 2310, such that the second electrical contact 2211 may be in electrical communication with the separation medium 2220 through the transfer portion 2320. In some embodiments, the first and/or second electrical contacts may be disposed in electrical communication with the separation medium 2220 via one or more intermediate electrical conductors or hydratable materials (e.g., sponges or foams) that may become electrical conductors after being hydrated with a bodily fluid. In some embodiments, the electrical contacts 2210 and/or 2211 may include printed electrodes, wires, or a combination thereof. As shown in FIG. 15, which includes an alternative embodiment of the biomarker detector cartridge 2000, the electrical connectors 2210 and 2211 may be connected to a DC power source (not shown) and a potential may be provided across the separation medium 2220 through the fluid collection portion 2300 during electrophoresis.

In some embodiments, the assay portion 2500 may include a capillary or channel that may transfer a quantity of the bodily fluid collected at the fluid collection portion 2300 to another portion of the electrophoretic cell 2200. For example, capillary or channel may transfer a quantity of the bodily fluid from the transfer portion 2320 to a hydratable material that may be proximate to the separation medium 2220. In some embodiments, the capillary or channel may be sized to contain about 1 to about 4 mL of fluid.

In an embodiment, the assay portion 2500 may be separate from the sample portion 2400 and may be separately sealed with a removable barrier prior to use. A removable barrier may be sealed about or to the electrophoretic cell 2200 at the assay platform 2515 or platform holder 2510 to encapsulate and protect the separation medium 2220. In some embodiments, the removable barriers described herein may also serve to maintain any moisture or solvent levels at the separation medium while keeping a source of nanoswitches dry and out of contact with any bodily fluid until after a sample has been collected. In some embodiments, a removable barrier disclosed herein may extend from the assay portion and may include a tab that may be grasped by a user to disconnect or otherwise remove the removable barrier from the assay portion. However, in some embodiments, the assay portion 2500 and sample portion 2400 may comprise a unitary structure such that they are not releasably separable (See FIG. 15).

Figure 13:
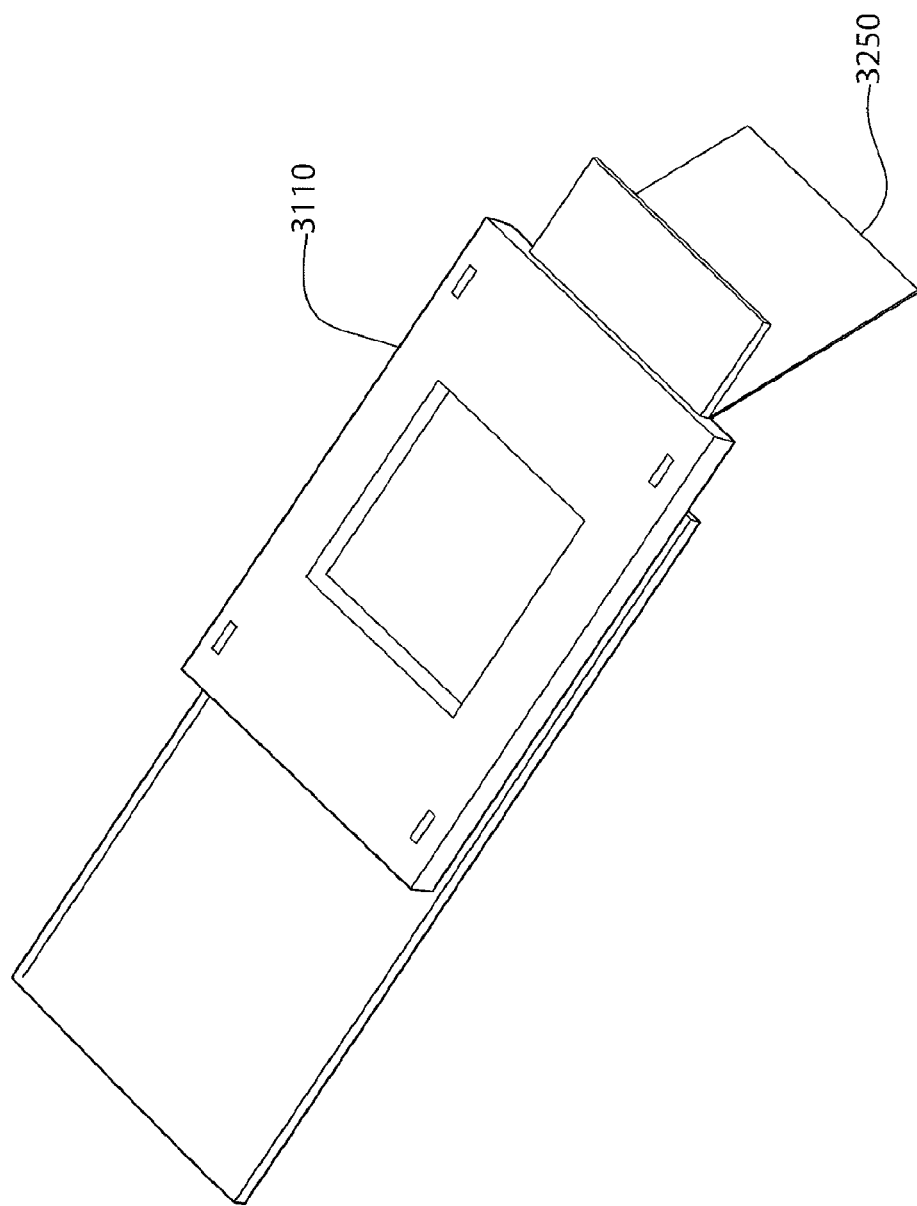
FIG. 13 is a perspective view of a variation on the biomarker detector cartridge that includes a removable barrier.
Figure 14:
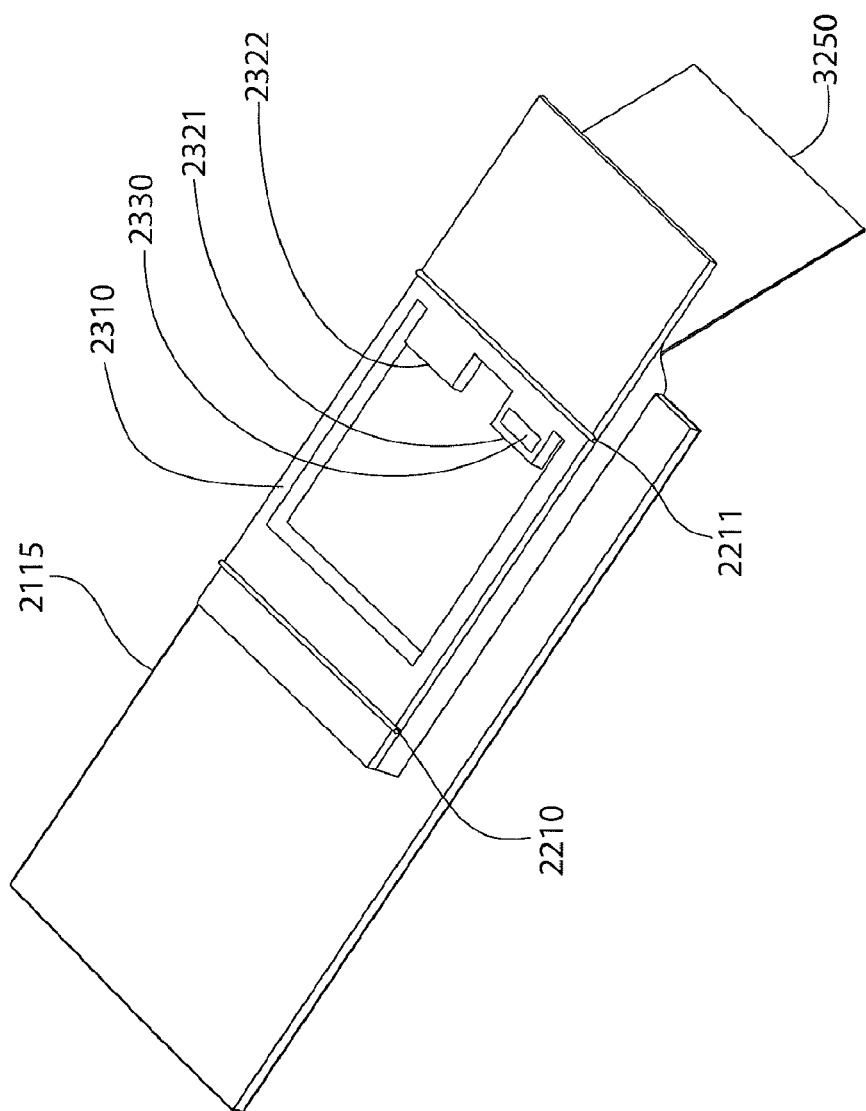
FIG. 14 is a perspective view of a variation on the biomarker detector cartridge of FIG. 13 with the cover removed.
Figure 16:
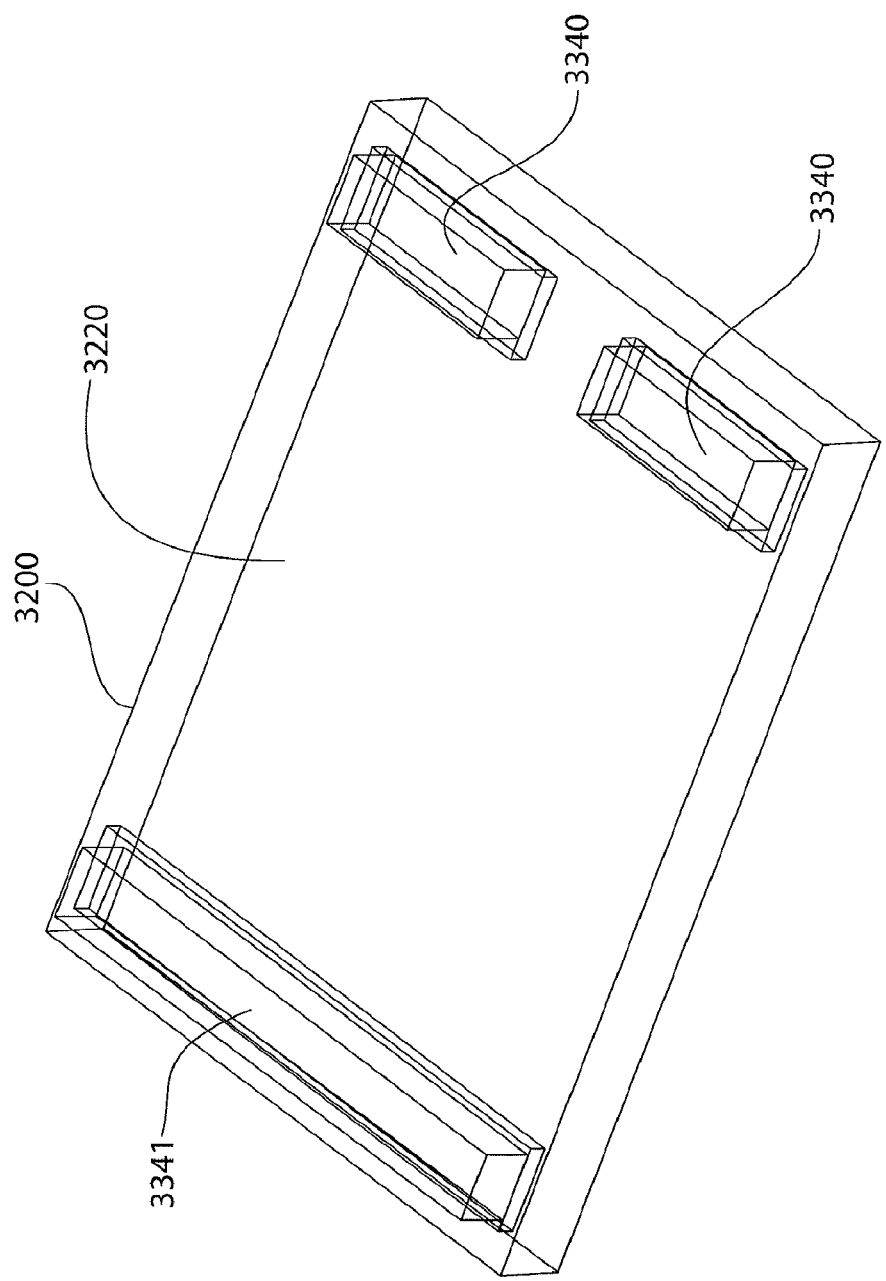
FIG. 16 is a perspective view of the separation medium in a variation on the biomarker detector cartridge.

In another embodiment, as shown in FIGS. 13 and 14, the biomarker detector cartridge 2000 may include an alternate cover 3110 and a removable barrier 3250 that may be sealed about or over the electrophoretic cell 2200 at the assay platform 2515 to encapsulate and protect the separation medium 2220 prior the performance of an assay (see also FIG. 15). In some embodiments, the removable barrier 3250 is a heat sealed foil. In some embodiments, the biomarker detector cartridge 2000 may include an aperture 3251 on the cartridge body 2115 through which the removable barrier 3250 may pass to cover the separation medium 2220. In some embodiments, an alternative electrophoretic cell, such as the one provided for the cartridge in FIGS. 13 and 14, may include a separation medium 3220 as shown in FIG. 16. As provided in FIG. 15, the separation medium 3220 may include transfer contact portions 3340 and 3341 that may contact the transfer portion 2320. In some embodiments, separation medium 3220 may include a contact 3341 for contacting fluid collection portion 2300. For example, the separation medium 3220 may receive both bodily fluids to be analyzed, with nanoswitches intermixed therewith, and an electrical potential through transfer contact portions 3340 and 3341 in conjunction with contact 3341.

Figure 17:
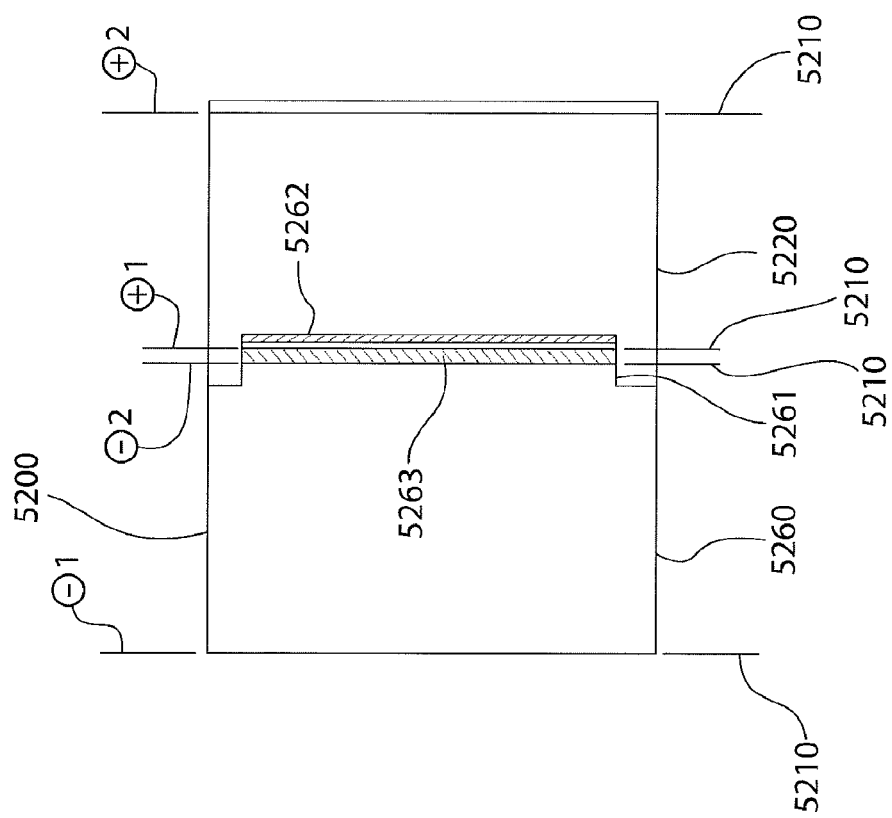
FIG. 17 illustrates an electrophoretic cell that includes a mixing chamber and separation medium that may be incorporated with any of the electrophoretic cells described herein.

In an embodiment, the electrophoretic cells described herein may include a mixing chamber in combination with a separation medium as depicted in FIG. 17. As shown in FIG. 17, an electrophoretic cell 5200 may include a mixing chamber 5260 that may be coupled to a separation medium 5220. In some embodiments, mixing chamber 5260 may include a volume of bodily fluid (e.g., about 0.01 mL to about 5 mL) that may include a biomarker to be analyzed and a quantity of nanoswitches. This volume of bodily fluid may be dilute and may require concentration prior to analysis at the separation medium. In the mixing chamber 5260, the nanoswitches may associate with the biomarkers to provide biomarker-bound nanoswitches. In some embodiments, the electrolytic cell may 5200 may include electrical contacts 5210, which may be divided as electrical contact pair 1 and electrical contact pair 2. Electrical contact pair 1 may be activated to concentrate the nanoswitches about the positive electrode of electrical contact pair 1 at location 5263, which may be at separation medium loading area 5261. After concentration, the electrical contact pair 1 may be deactivated and the electrical contact pair 2 may be activated to allow for separation of the bound and unbound nanoswitches on the separation medium 5220 when the nanoswitches cross the mixing point 5262 and transition from the mixing chamber 5260 to the separation medium 5220.

Figure 18:
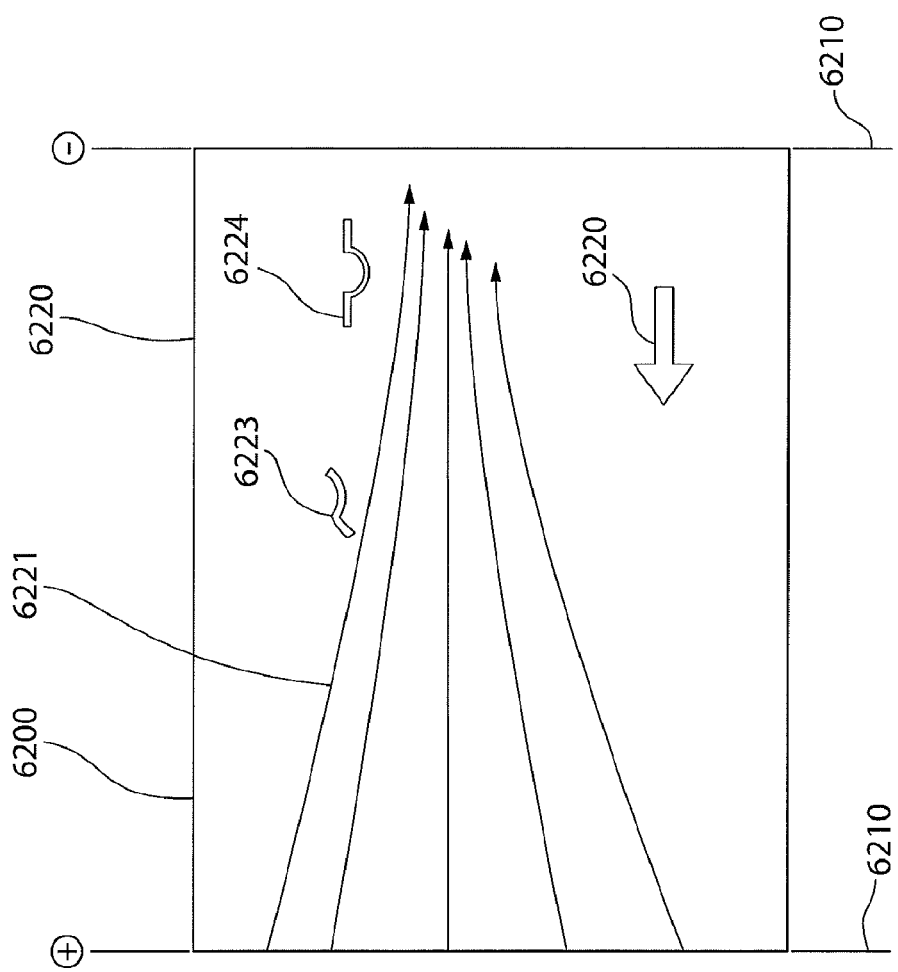
FIG. 18 illustrates an electrophoretic cell that includes a separation medium that includes a viscous fluid that may be used to separate biomarker bound nanoswitches from unbound nanoswitches.

In an embodiment, the electrophoretic cells described herein may include a viscous fluid separation medium as shown in FIG. 18. As shown in FIG. 18, an electrophoretic cell 6200 may be provided that includes a separation medium 6220 that includes a viscous fluid. In some embodiments, the viscous fluid in the separation medium 6220 may be provided with a flow from the left portion of the separation medium 6220 to the right portion of the separation medium 6220. Moreover, the electrophoretic cell 6200 may include electrical contacts 6210. Upon activation of electrical contacts 6210 a potential may be placed across the separation medium 6220. In FIG. 17, a flow of viscous fluid provides a force 6221 while the potential across the separation medium 6220 provides an electromotive force 6222. The electromotive force 6222 may be the same on biomarker bound nanoswitches 6224 and unbound nanoswitches 6223. However, the fluid drag on the biomarker bound nanoswitches 6224 may be greater than that on the unbound nanoswitches 6223, which allows for separation in the separation medium 6220.

Figure 19:
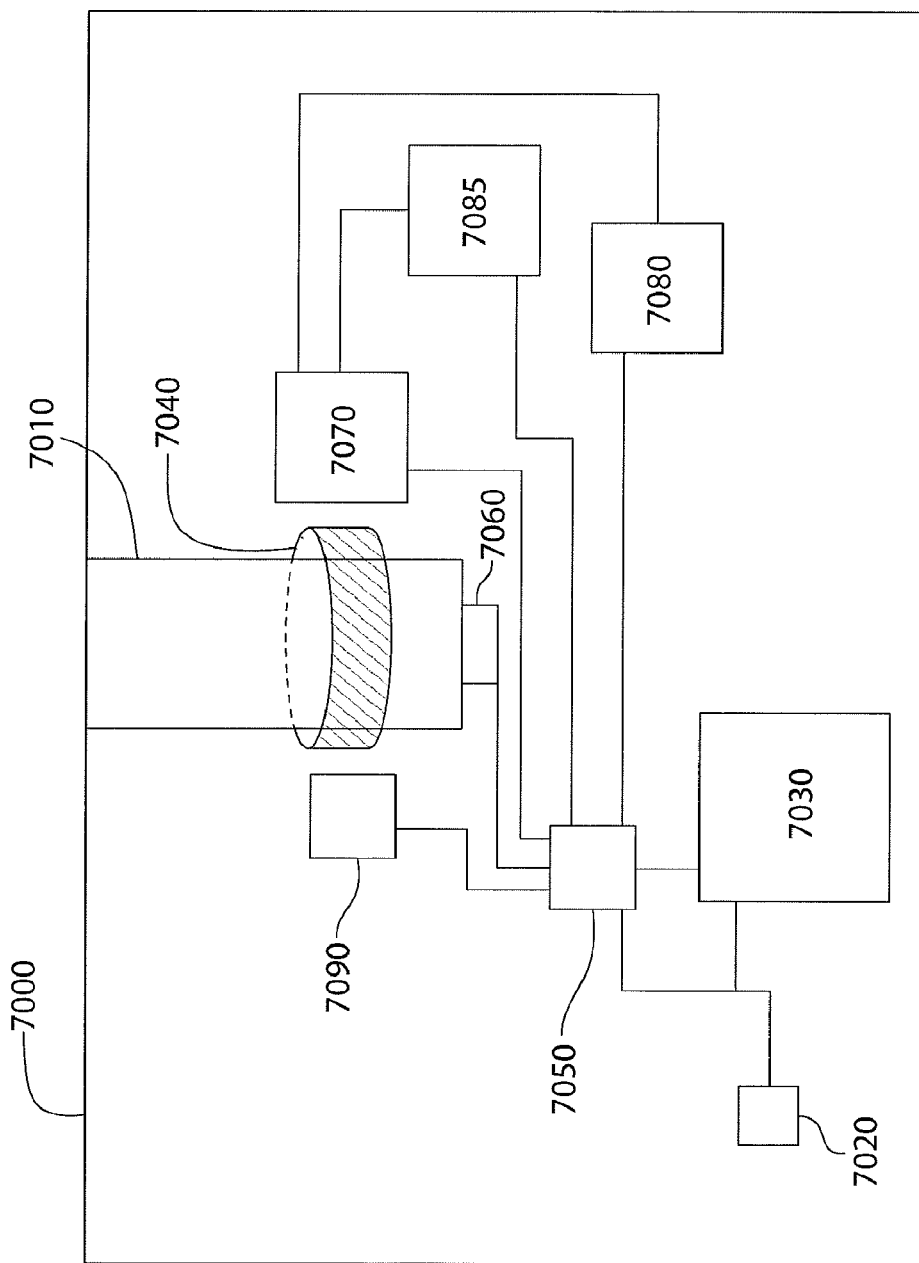
FIG. 19 is a schematic view of a base for processing biomarker detector cartridges disclosed herein.

In an embodiment, as shown in FIG. 19, a base 7000 is provided for processing the biomarker detector cartridges described herein. In some embodiments, the base 7000 includes a biomarker detector cartridge receiver 7010 that may receive at least a portion of the biomarker detector cartridge. In some embodiments, the biomarker detector cartridge receiver 7010 may receive at least the portion of the biomarker detector cartridge that includes the assay portion. In some embodiments, the base 7000 may include electrical contacts 7060 that may be proximate to the biomarker detector cartridge receiver 7010 and may be positioned such that, upon reception of a cartridge at the cartridge receiver 7010, the electrical contacts 7060 may align and releasably contact, and provide electrical communication to, the electrical contacts present on the cartridge. In some embodiments, the electrical contacts may include 2 contacts, or 4 contacts, or 6 contacts, which may be separately activated or energized. In some embodiments, the electrical contacts described herein may be disposed at the electrophoretic cell to provide orthogonal electric fields.

In some embodiments, the base may include a controller 7050 that may be in communication with a power source 7030, an on/off switch 7020, and the electrical contacts 7060. In some embodiments, an on/off switch 7020 may be omitted where the base 7000 is activated upon reception of a cartridge at the cartridge receiver 7010. In some embodiments, the controller 7050 includes a microprocessor that may cause an event to occur based on a received signal from one or more of the power source 7030, on/off switch 7020, a transmitter 7080, indicators 7085, electrical contacts 7060, light source 7090, and photodetector 7070. Generally, a "controller," as used herein includes, but is not limited to, any circuit or device that coordinates and controls the operation of one or more input or output devices (e.g., power source 7030, on/off switch 7020, a transmitter 7080, indicators 7085, electrical contacts 7060, light source 7090, and/or photodetector 7070). For example, a controller can include a device having one or more processors, microprocessors, or central processing units (CPUs) capable of being programmed to perform input or output functions. A controller may also include a state machine or a control unit. A controller may utilize analog or digital technology and may convert signals from analog to digital and vice versa.

In certain embodiments, the power source 7030 may include a source of alternating current (AC) that is converted to DC, as is known in the art. In some embodiments, the power source 7030 is a battery. As used herein, the term "battery" refers to an electro-chemical device comprising one or more electro-chemical cells and/or fuel cells, and so a battery may include a single cell or plural cells, whether as individual units or as a packaged unit.

In some embodiments, the base 7000 may include an electrophoresis cell reader, which may be understood to include a light source 7090, a light filter 7040, and a photodetector 7070, each of which may be in communication with the controller 7050. In some embodiments, each of the light source 7090, light filter 7040, and photodetector 7070 may be disposed proximate to the cartridge receiver 7010. In some embodiments, the light filter 7040 may be interposed between the light source 7090 and the photodetector 7070.

In alternative embodiments, the base may be coupled to, and/or embodied on, the biomarker detector cartridge where the electrical contacts on the biomarker detector cartridge are coupled and, optionally, unreleasably or directly connected to the electrical contacts provided at the base. For example, the components described herein at the base may be provided on a biomarker detector cartridge to provide a standalone device.

In some embodiments, during operation of the base 7000, a cartridge may be placed in the cartridge receiver 7010 and electrical contacts 7060 may electrically communicate with the electrophoretic cell such that electrophoresis may occur at the separation medium in the cartridge. After completion of the electrophoretic assay, the light source 7090 may be activated to elucidate stained or dyed separation medium, which may allow for the elucidation of biomarker-bound nanoswitches and unbound nanoswitches. In some embodiments, the light passing through the electrophoretic cell at the cartridge receiver 7010 may be filtered through the light filter 7040 and captured at photodetector 7070. In some embodiments, the light filter 7040 may be disposed in a number of configurations about the cartridge receiver 7010. The light filter 7040 may be provided as a ring, a sheath, a plate, a lens, or a film. In some embodiments, the light filter 7040 may include two or more light filters.

In some embodiments, a photodetector may include one or more photomultiplier tube detectors and photodiode detectors. As used herein, the term "photomultiplier" or "photomultiplier tube" refers to optical detection components that convert incident photons into electrons via the photoelectric effect and secondary electron emission. The term photomultiplier tube is meant to include devices that contain separate dynodes for current multiplication as well as those devices that contain one or more channel electron multipliers. As used herein, the term "optical detector" or "photodetector" refers to a device that generates an output signal when irradiated with optical energy. Thus, in its broadest sense the term optical detector system is taken to mean a device for converting energy from one form to another for the purpose of measurement of a physical quantity or for information transfer. Optical detectors include but are not limited to photomultipliers and photodiodes. As used herein, the term "photodiode" refers to a solid-state light detector type including, but not limited to PN, PIN, APD, CMOS, and CCD. In some embodiments, the electrophoretic cell reader may include one or more of a PN based detector, a PIN based detector, an APD based detector, a CMOS based detector, and a CCD based detect In some embodiments, the base 7000 includes a transmitter 7080 and one or more indicators 7085, each of which may be connected to the controller 7050. In some embodiments, the transmitter 7080 may include a wireless or wired transmitter and may include, for example, a Bluetooth transmitter, a Wi-Fi transmitter, or an infrared transmitter that may be used in conjunction with the electrophoresis cell reader to transmit results of the electrophoretic analysis to a computer or handheld device having a comparable receiver. In some embodiments, the one or more indicators 7085 may include one or more lights (e.g., LED lights) on the base that may indicate when an electrophoretic analysis is being performed, a selected status, or another indication as selected by the user.

In an embodiment, the invention includes a biomarker detector cartridge 8000, as shown in FIGS. 20 to 23, where the sample portion and assay portion are separated by a seal that may be pierced by one or more cannulas on the sample portion when the assay portion is read at a base.

Figure 20A:
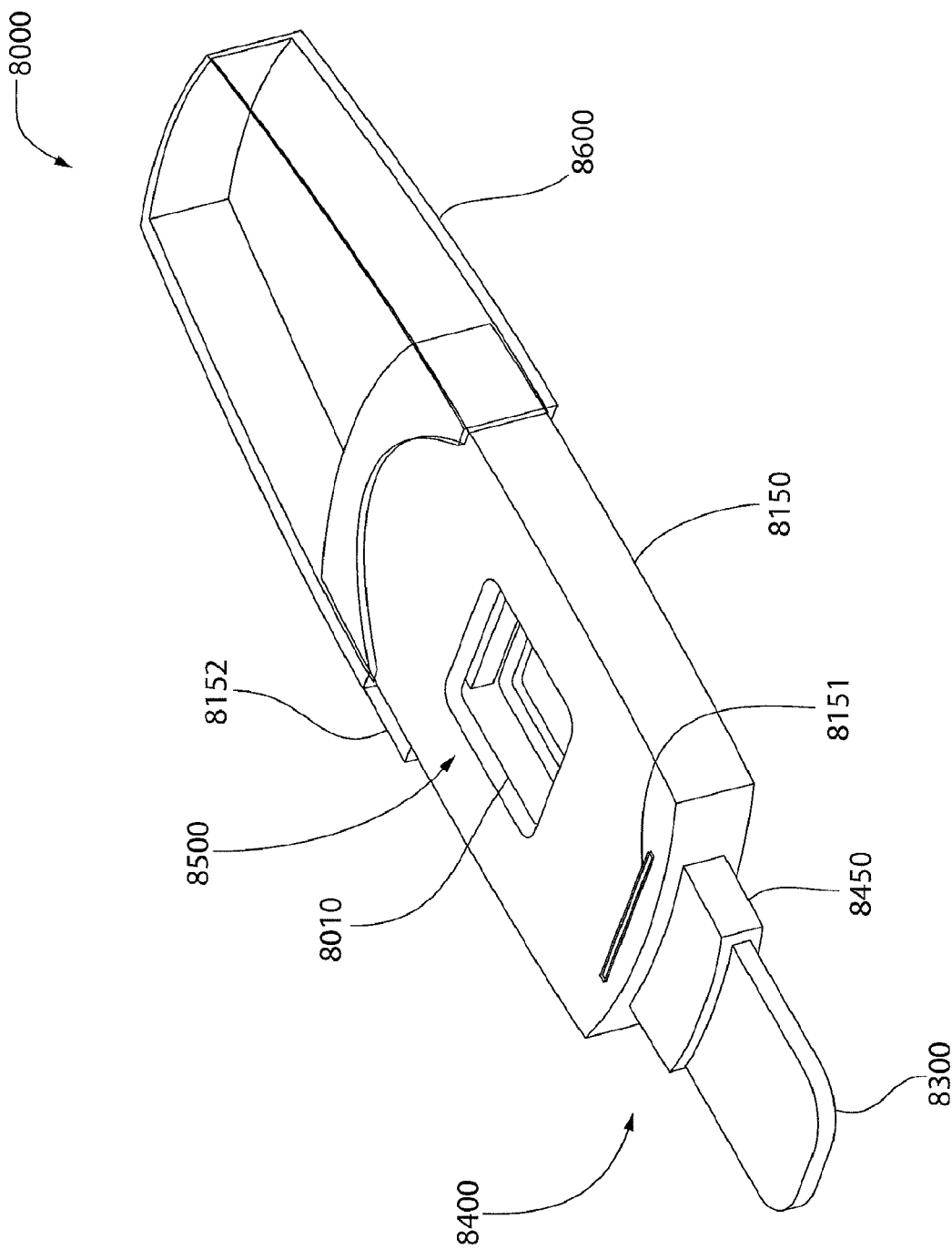
FIGS. 20A to 20D illustrate exterior views of an exemplary biomarker detector cartridge, including a perspective view of an uncapped biomarker detector cartridge (FIG. 20A), a top view of an uncapped biomarker detector cartridge (FIG. 20B), a top view of a capped biomarker detector cartridge (FIG. 20C), and a top view of a capped biomarker detector cartridge under electrophoretic analysis (FIG. 20D)
Figure 20B:
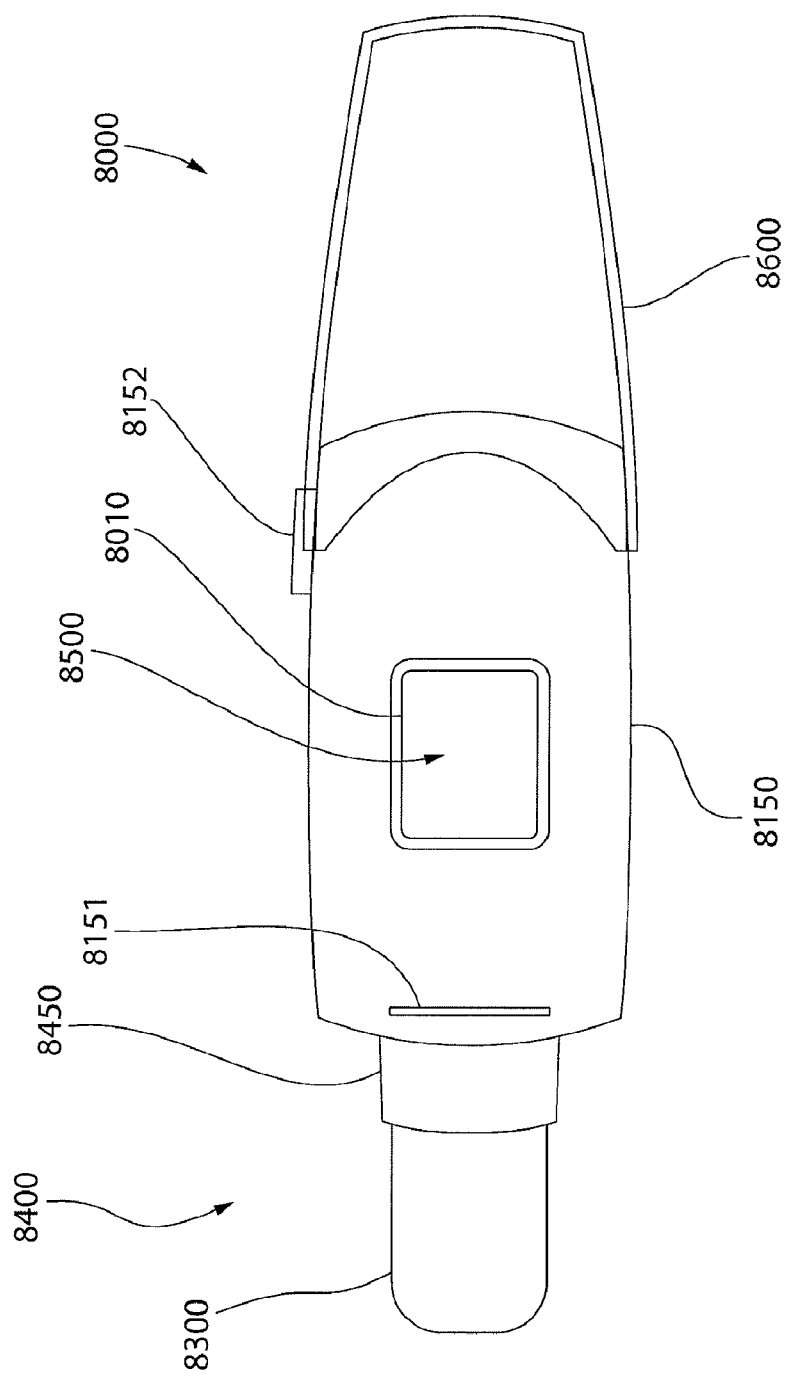
Figure 20C:
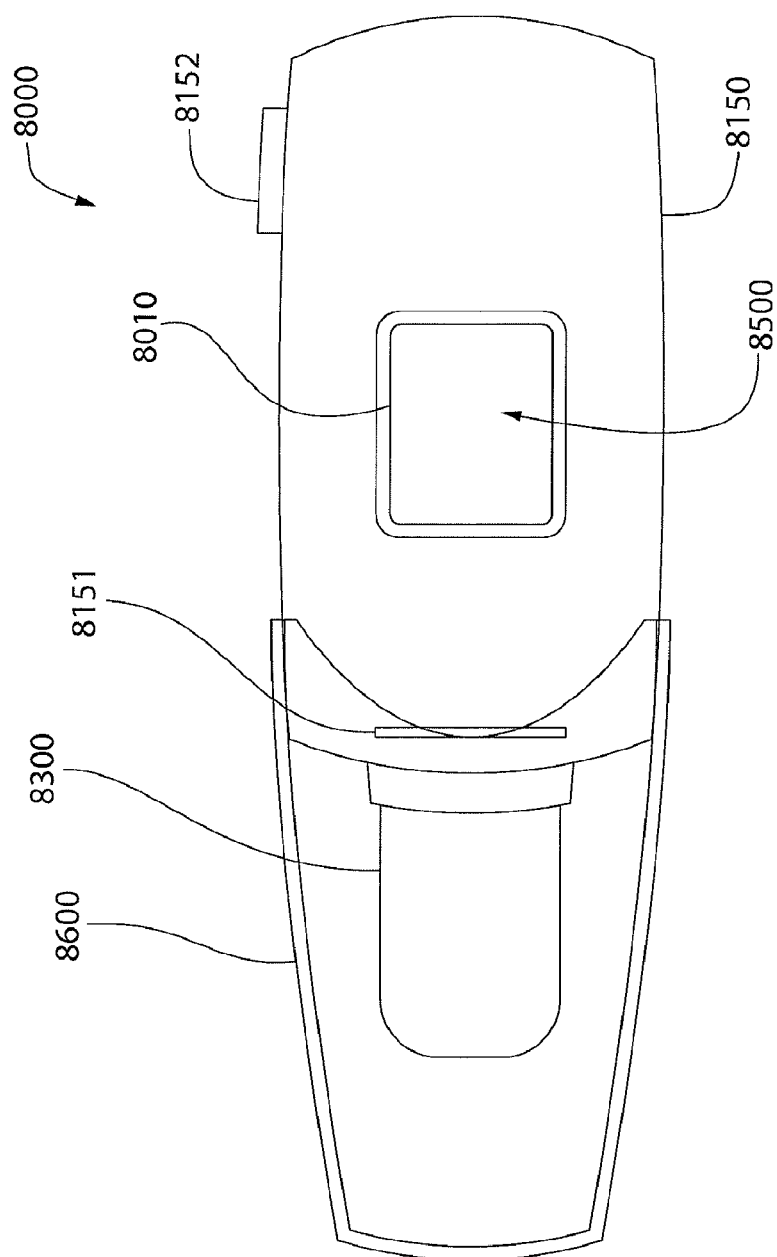
Figure 20D:
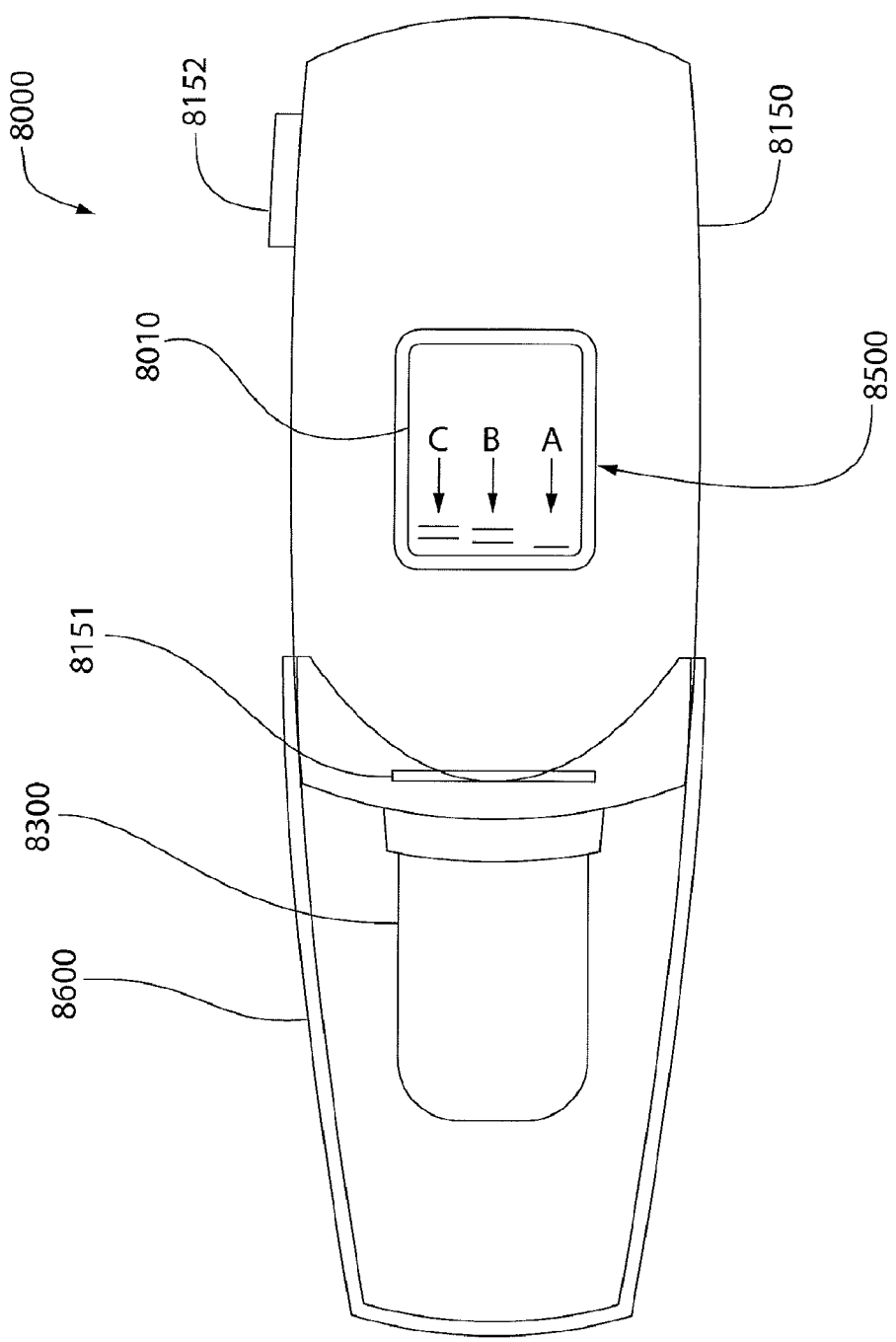

As shown in FIGS. 20A and 20B, the biomarker detector cartridge 8000 may have a cartridge body 8150 having a sample portion 8400 and an assay portion 8500. The biomarker detector cartridge 8000 may include a cap 8600, which may be used to cover the sample portion 8400. As described herein, the cap 8600 may be releasably affixed to an end of the cartridge body 8150 and thereby extend the length of the cartridge body to allow a user to have more surface area to grasp the cartridge when collecting a sample at the fluid collector 8300. In addition, as shown in FIGS. 20C and 20D, the cap 8600 may be used to cover the sample portion 8400 and may be releasably fixed to the cartridge body 8150 at sample portion 8400 by connecting to ridge 8151.

Figure 22:
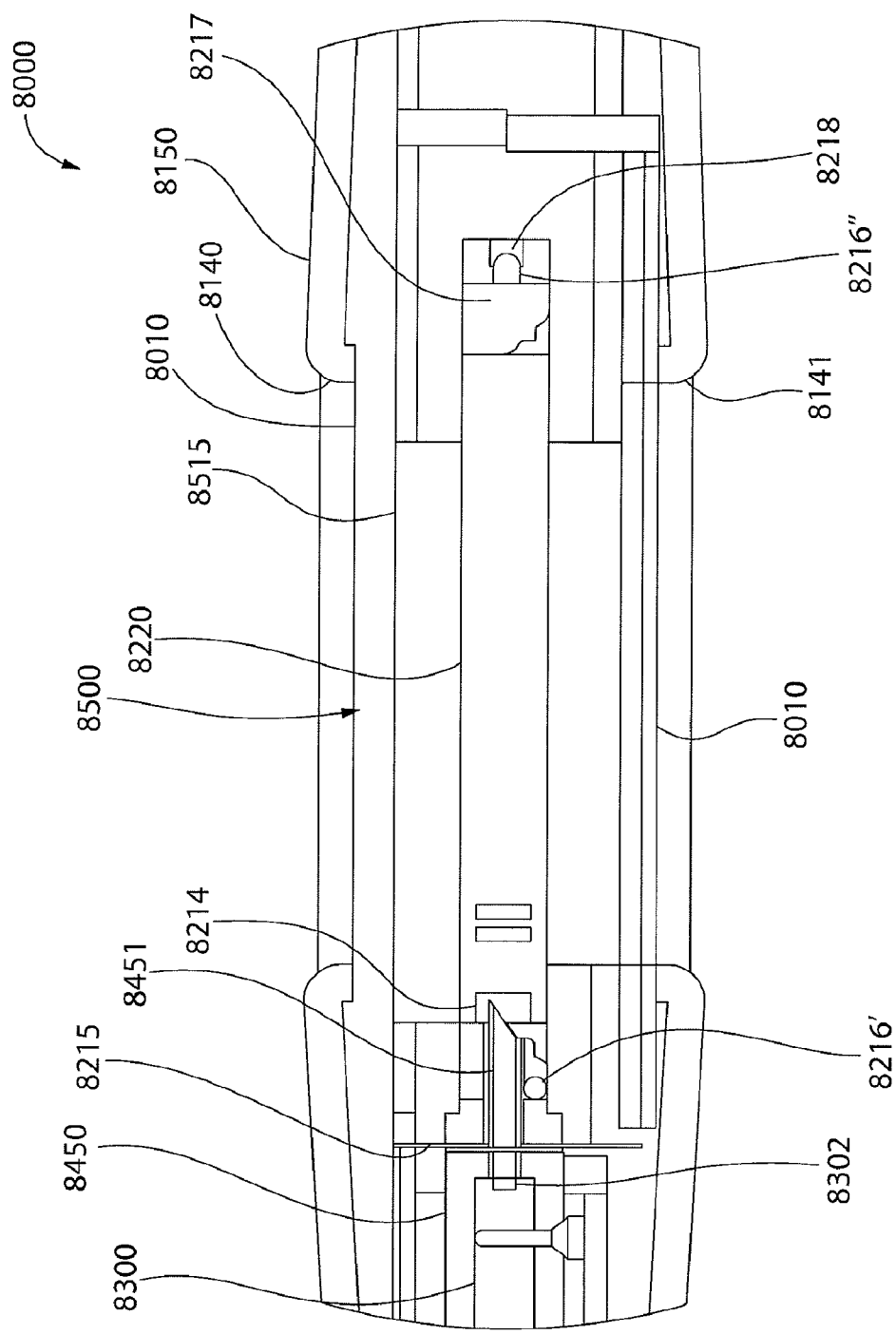
FIG. 22 illustrates internal components of the exemplary biomarker detector cartridge of FIGS. 20A to 20D.
Figure 23:
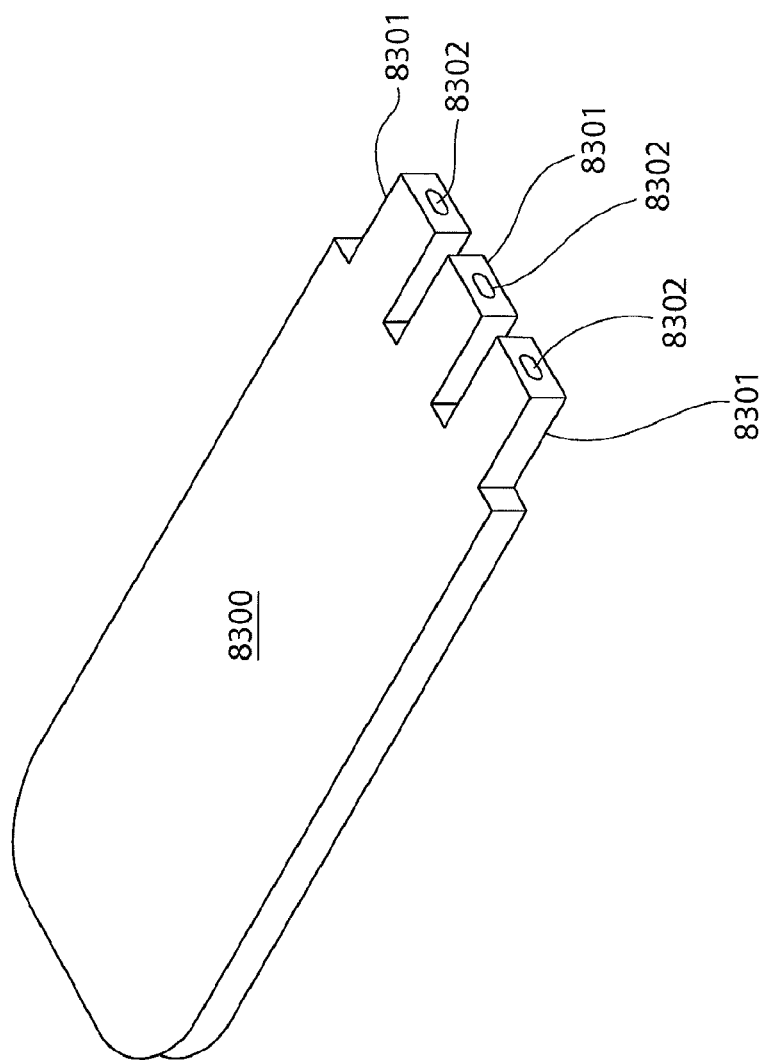
FIG. 23 illustrates a fluid collector of the exemplary biomarker detector cartridge of FIGS. 20A to 20D.

As shown in FIGS. 20A to 20D, the biomarker detector cartridge 8000 may include a cartridge body 8150 having a boss 8152 and windows 8010 that may cover the assay portion 8500 at apertures 8140 and 8141 (shown in FIG. 22). The boss 8152 may connect to the cover 8600 and may be used align the biomarker detector cartridge 8000 in a base disclosed herein.

As shown in FIGS. 20A to 20D and FIG. 21, the sample portion 8400 may include a fluid collector 8300 which may be connected to the cartridge body 8150 through a frame 8450. With regard to FIGS. 21 to 23, the frame 8450 may include a number of cannula 8451 (e.g., three cannulas), which may be in fluidic communication with the fluid collector 8300 disposed within the frame 8450 through the fluid collector applicators 8301. The sample portion 8500 may include a reagent source 8302 (e.g., a source of nano-switches, as described herein), which may be disposed at the applicators 8301 of the fluid collector 8300. The reagent source 8302 may be disposed at the end of the applicators 8301 such that as fluid is received at the fluid collector 8300, the fluid may flow through the applicators 8301 and dissolve the reagent source 8302 before passing through the cannulas 8451. The frame 8450 may include one or more fluid sensors 8452 that may be disposed in communication with the applicators 8301 of the fluid collector 8300 such that the fluid sensors 8452 may indicate, via a colorimetric or electronic indicator, that fluid received at the fluid collector 8300 has flowed to the applicators 8301.

The assay portion 8500 may include an assay platform 8515 upon, which may include an electrophoretic cell 8200. The electrophoretic cell 8200 may include a separation medium 8220, which may include one or more loading wells 8214 (e.g., three loading wells) that may correspond to cannulas 8451. As shown in FIG. 22, the electrophoretic cell 8200 may include a foam 8217 that may abut or connect to an end of the separation medium 8220 opposite the end that faces the cannulas 8451. The foam 8217 may be an electrolysis bubble management foam that may manage generation of bubbles during electrophoresis. For example, the foam 8217 may have holes in it for the cannulas 8451 to pass through, but otherwise the foam may remove bubbles that form at the electrodes during electrophoresis. The electrophoretic cell 8200 may further include an electrode 8216, which may be an anode, that may be provided in electrical communication with the separation medium 8220. The electrophoretic cell 8200 may include a bubble vent path 8218 to allow for gas to escape during electrophoresis in the electrophoretic cell 8200.

The assay portion 8500 may include a seal 8215 (e.g., foil) that may be placed over the loading wells 8214 of the separation medium 8220 to maintain the moisture of the separation medium 8220 and thereby prevent desiccation of the separation medium 8220 prior to use.

Figure 21:
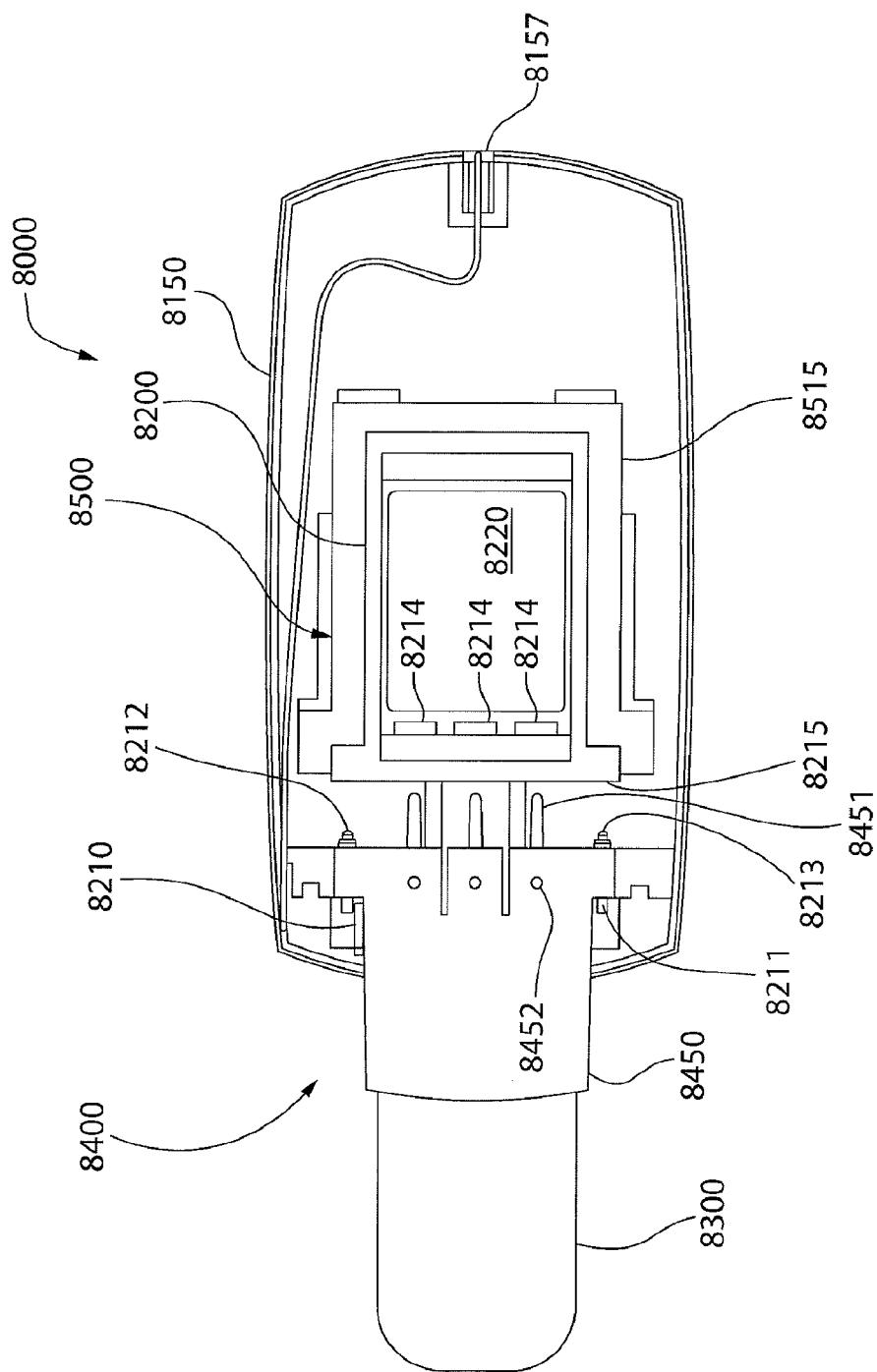
FIG. 21 illustrates internal components the exemplary biomarker detector cartridge of FIGS. 20A to 20D.

As shown in FIGS. 21 and 22, the frame 8450 may be movable between a first position (i.e., a non-analysis position as shown in FIG. 21) and a second position (i.e., an analysis position as shown in FIG. 22). In the first position (FIG. 21), fluid may be collected at the fluid collector 8300 prior to analysis. A user may then insert the biomarker detector cartridge 8000 into a base, which may then force the frame 8450 into second position (FIG. 22) whereby the cannulas 8451 pierce the seal 8215 and may deposit a mixture of fluid collected at the fluid collector 8300 and reagent from the reagent source 8302 at the loading wells 8214.

The frame 8450 may include first and second electrical contacts 8210 and 8211, respectively, which may connect to electrodes 8212 and 8213, respectively. The first and second electrical contacts 8210 and 8211 may be in electrical communication with electrical connector 8157. The electrical connector 8157 may be a flat flexible connector (FFC) and may be connected to a source of electrical current as may be provided when connected to a corresponding electrical connector in a base. In some embodiments, the electrical connector 8157 may be in electrical communication with electrodes 8212 and 8213 through electrical contacts 8210 and 8211, respectively.

In the second position of the frame 8450, the electrodes 8212 and 8213 may contact the electrophoretic cell 8200, at electrode 8216' (which may optionally be two electrodes), and may thereby provide a selected potential across the separation medium 8220 between the electrodes 8212/8213, electrode 8216', and electrode 8216". In some embodiments, the electrodes 8212 and 8213 may serve as cathodes, through their connection to electrode(s) 8216', while electrode 8216" may serve as an anode. Furthermore, electrodes 8216' and 8216" may be connected to electrical connector 8157.

A biomarker detector cartridge 8000 under analysis is depicted in FIG. 20D. For example, an assay portion 8500 is visible under the window 8010 with three lanes shown (i.e., trace A, trace B, and trace C): a control is provided in trace A (one line); a substrate has been detected in trace B (two lines, which indicate that one reagent is bound to a biomarker); and a substrate has been detected in trace C (two lines, which indicate that one reagent is bound to a biomarker).

In an embodiment, as shown in FIGS. 24A to 24F, the invention includes a base 9000 that is provided for processing the biomarker detector cartridge 8000.

In some embodiments, the base 9000 may include a cover 9150 having a biomarker detector cartridge receiver 9152 disposed therein that may receive at least a portion of the biomarker detector cartridge 8000. For example, the biomarker detector cartridge receiver 9152 may include a cavity that may enclose the assay portion 8500 of the biomarker detector cartridge 8000.

The base 9000 may include elements for processing the assay portion 8500 of the biomarker detector cartridge 8000. For example, the base 9000 may include an optical detector 9200, a lens 9201, a light filter 9202 that may block short wavelength light, and a light source 9210, which may be a short wave length light source. In some embodiments, the optical detector 9200 may be positioned to face the assay portion 8500, with the lens 9201 and short wave length filter 9202 disposed between the optical detector 9200 and the assay portion 8500. The light source 9210 may be positioned on the opposing side of the biomarker detector cartridge 8000 facing the assay portion 8500, such that activation of the light source 9210 results in the transmission of light through the assay portion 8500, light filter 9202, and lens 9201 and into the optical detector 9200.

The base 9000 my further include a controller 9250 (i.e., a main PCB) in electrical communication with the optical detector 9200 and light source 9210. The controller 9250 may be connected to an electrical connector 9251 provided to connect with, and transmit an electric current to, electrical connector 8157.

Figure 24A:
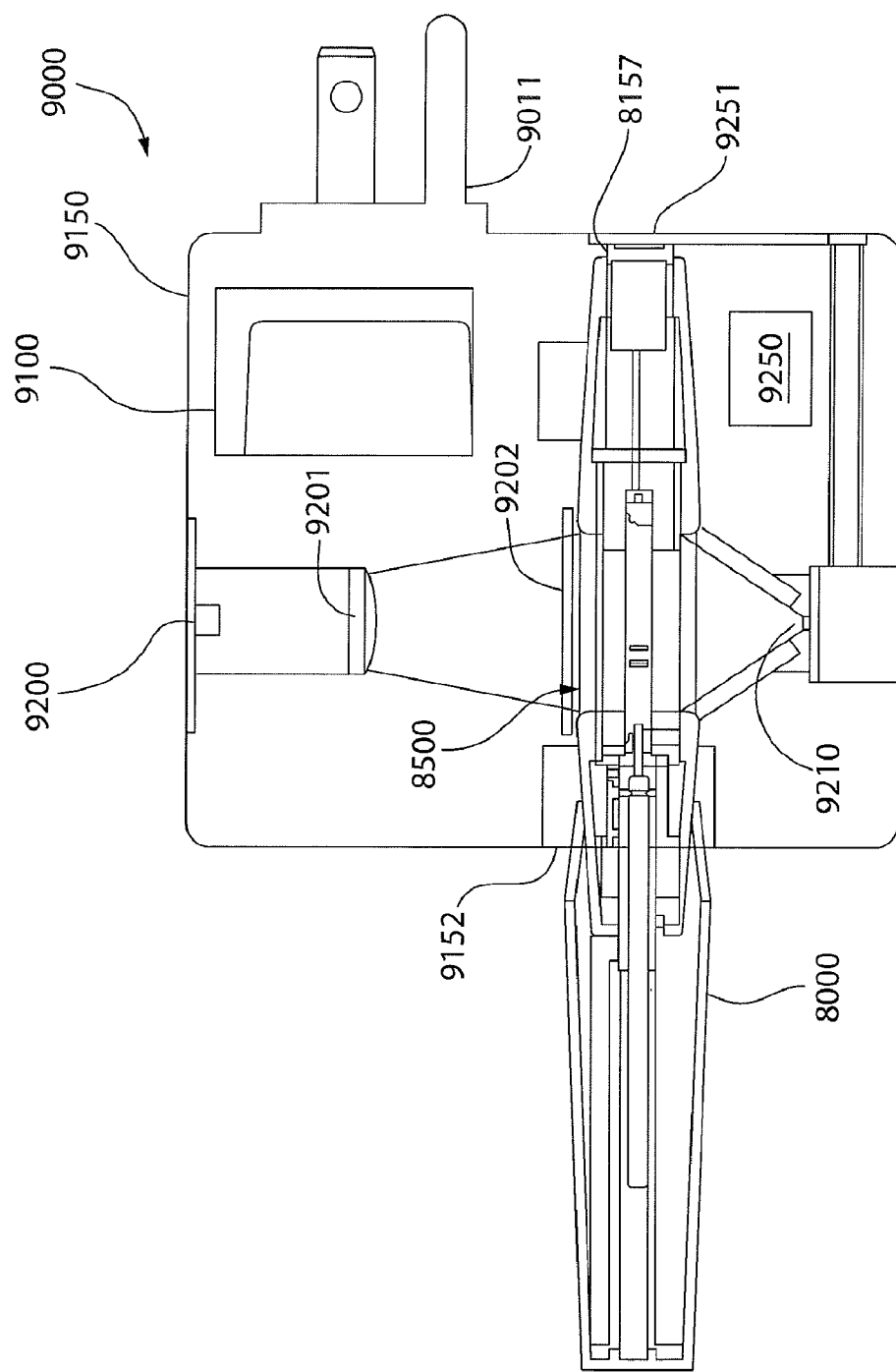
FIGS. 24A to 24F illustrate various embodiments of a base used for reading the biomarker detector cartridge of FIGS. 20A to 20D, including a base that may be affixed to an electric receptacle (FIG. 24A), a perspective cutaway of a table top base (FIG. 24B), a perspective cutaway of the table top base shown in FIG. 24B (FIG. 24C), a perspective cutaway of the table top base shown in FIG. 24B (FIG. 24D), a perspective view of the table top base shown in FIG. 24B (FIG. 24E), and a perspective cutaway view of an another embodiment of the table top base shown in FIG. 24B (FIG. 24F)
Figure 24B:
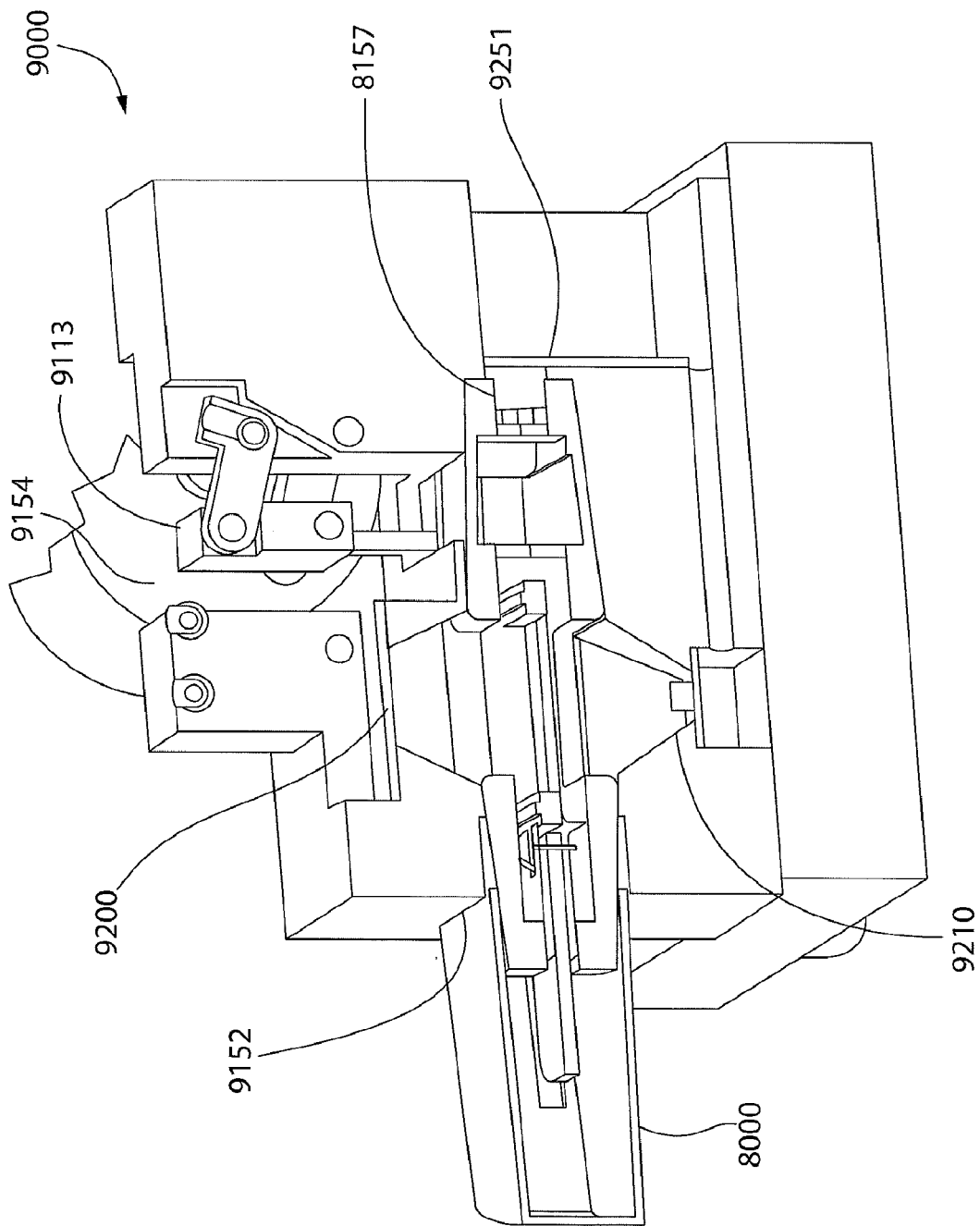
Figure 24C:
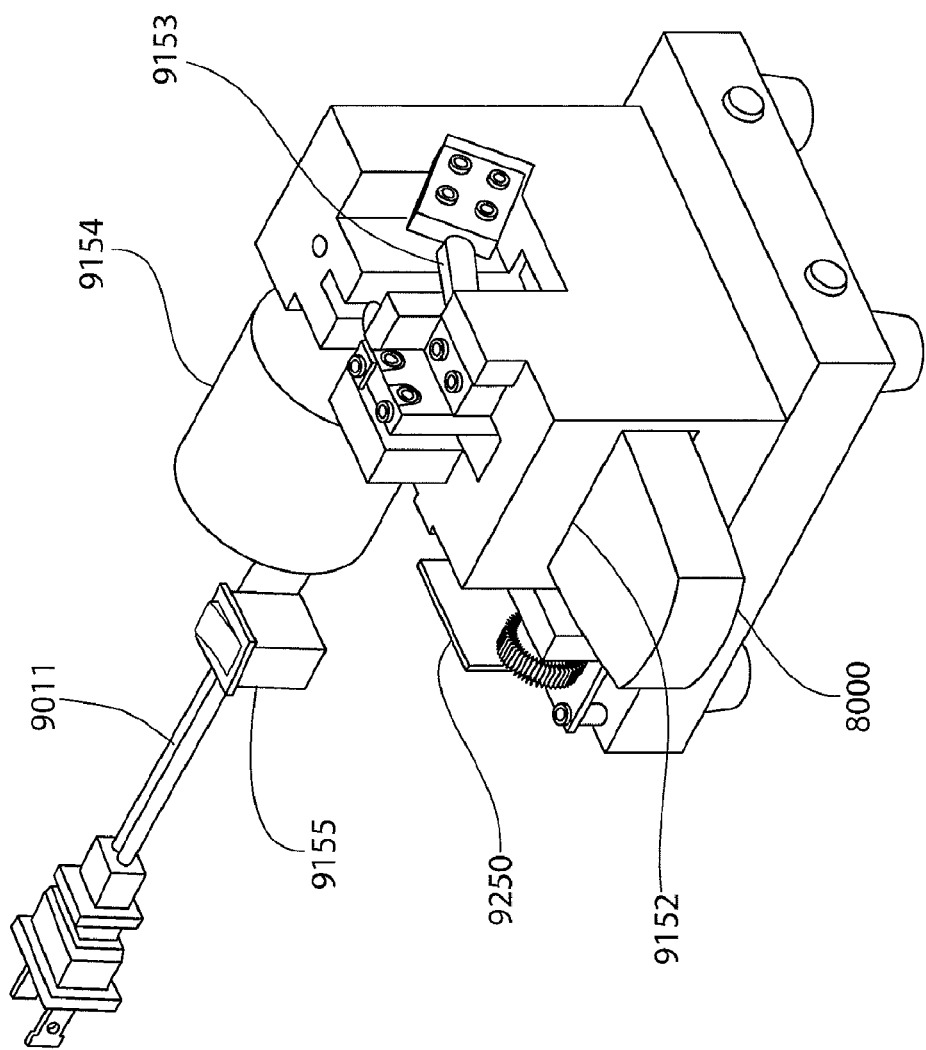
Figure 24D:
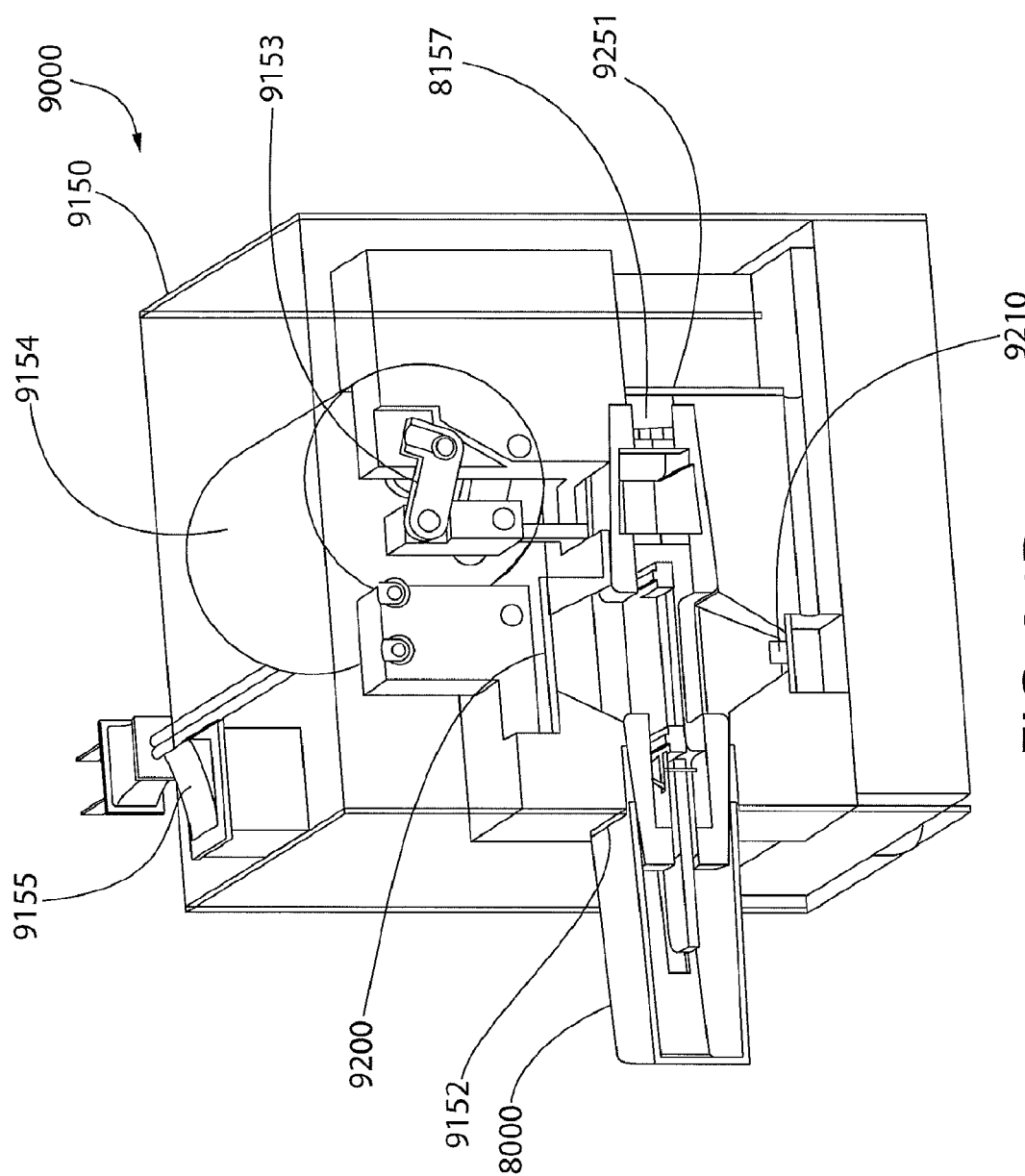
Figure 24E:
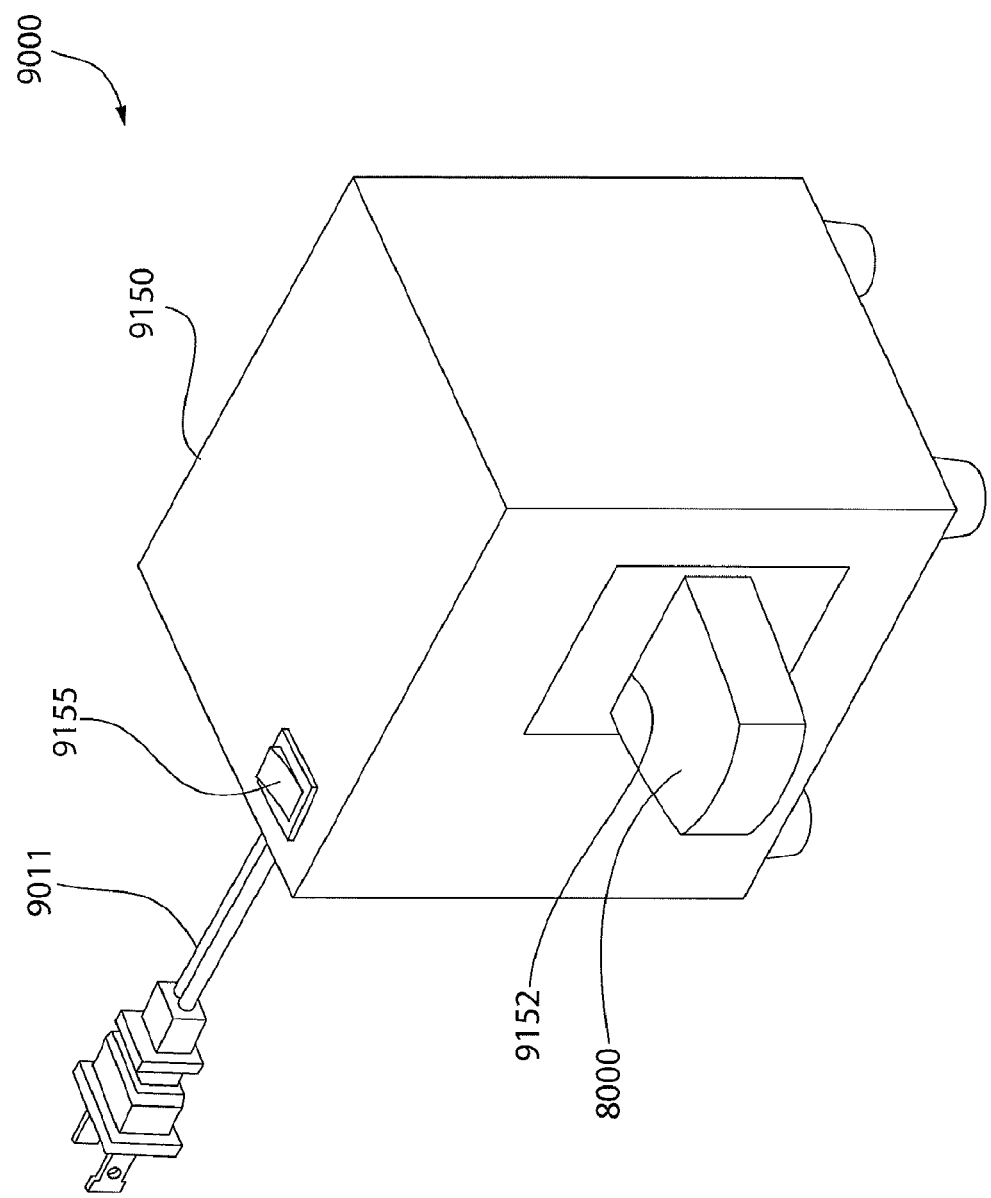
Figure 24F:
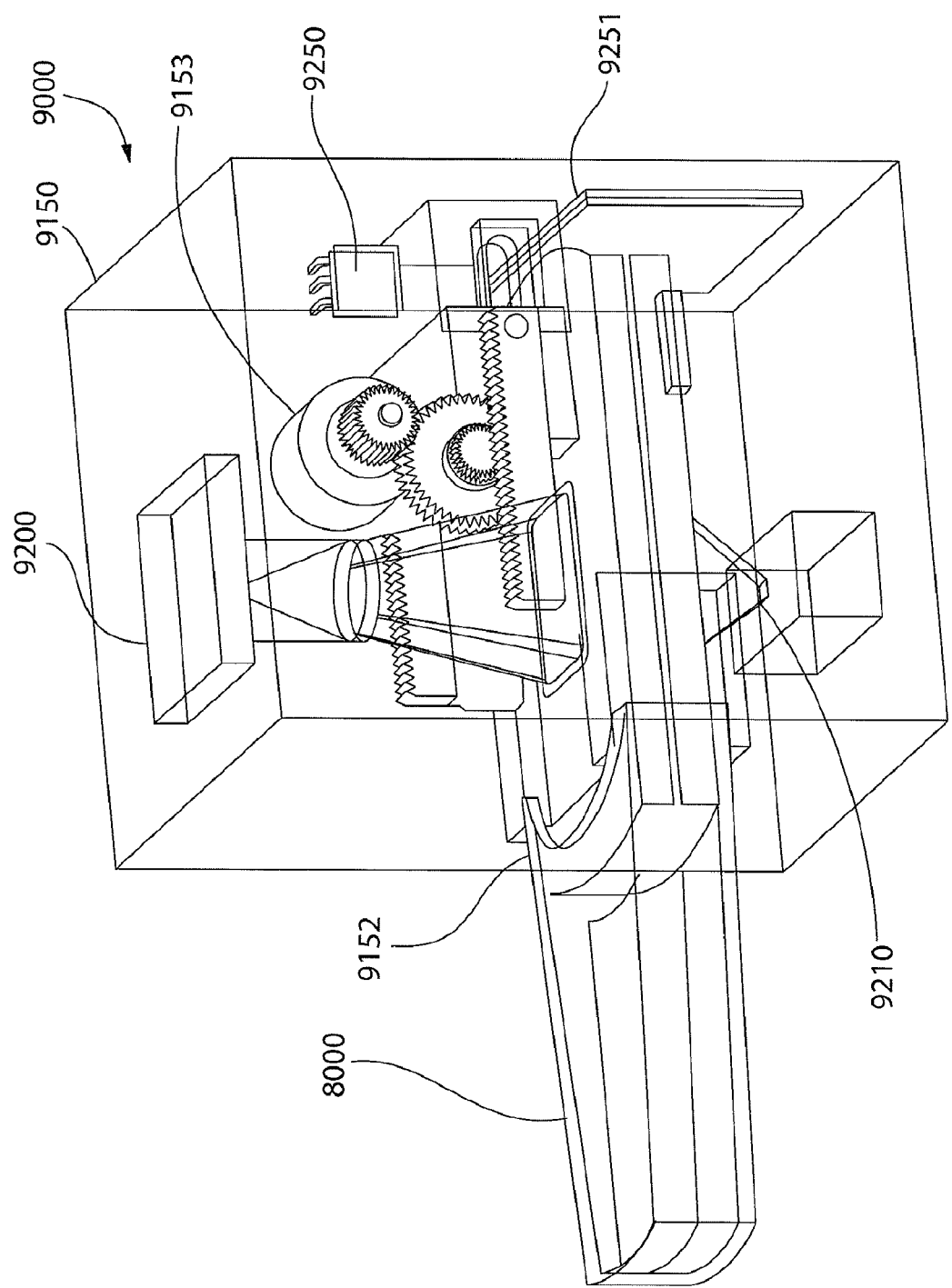

In some embodiments, insertion of a biomarker detector cartridge 8000 into the base 9000 at receiver 9152 may result in (1) movement of the frame 8450 from the first position to the second position (i.e., FIG. 22); (2) contact between the electrical connector 8157 with electrical connector 9251; and (3) activation of the base 9000 to begin processing of the assay portion 8500 (e.g., transmission of an electric current to the electrophoretic cell 8200 through electrical connector 9251). In some embodiments, as shown in FIGS. 24B to 24F, the base 9000 may retract the biomarker detector cartridge 8000 into the receiver 9152 through powered retraction element 9153. Powered retraction element 9153 may also be provided to eject the biomarker detector cartridge from the base 9000 and may be operated to hold the biomarker detector cartridge 8000 in place during analysis. The powered retraction element 9153 may be powered by motor 9154. In FIGS. 24B to 24D, the powered retraction element 9153 is depicted as a powered arm. In FIG. 24F, the powered retraction element 9153 is depicted as a set of powered gears that operate a rack system for retracting, ejecting, and/or holding the biomarker detector cartridge 8000, as described herein.

In some embodiments, the base 9000 may include an on/off switch 9155 that may be disposed on the case 9150.

In some embodiments, the base 9000 may include a power supply 9100, which may be in electrical communication with the controller 9250, a motor 9154, a powered retraction element 9153, and a plug 9011 that may be inserted into an electrical receptacle.

In an embodiment, as shown in FIGS. 25 to 30, a biomarker detector cartridge 8000-1 having seals, which may be foil seals, that separate, and maintain the moisture of, the separation medium 8220-1.

In some embodiments, the biomarker detector cartridge 8000-1, may include a cartridge body 8150-1. In some embodiments, shown in FIG. 25, the biomarker detector cartridge 8000-1 may be packaged for shipping without a cap or cover. In some embodiments, the biomarker detector cartridge 8000-1 includes a sample portion 8400-1 and an assay portion 8500-1. The sample portion 8400-1 may include a fluid collector 8300-1 connected to a frame 8450-1 and having applicators 8301-1, which are provided to contact, and transmit fluid to, the separation medium 8220-1. The sample portion 8400-1 may include a connecting portion 8304-1 that is provided to contact, and provide fluid communication with, both the fluid collector 8300-1 and the separation medium 8220-1.

Figure 25:
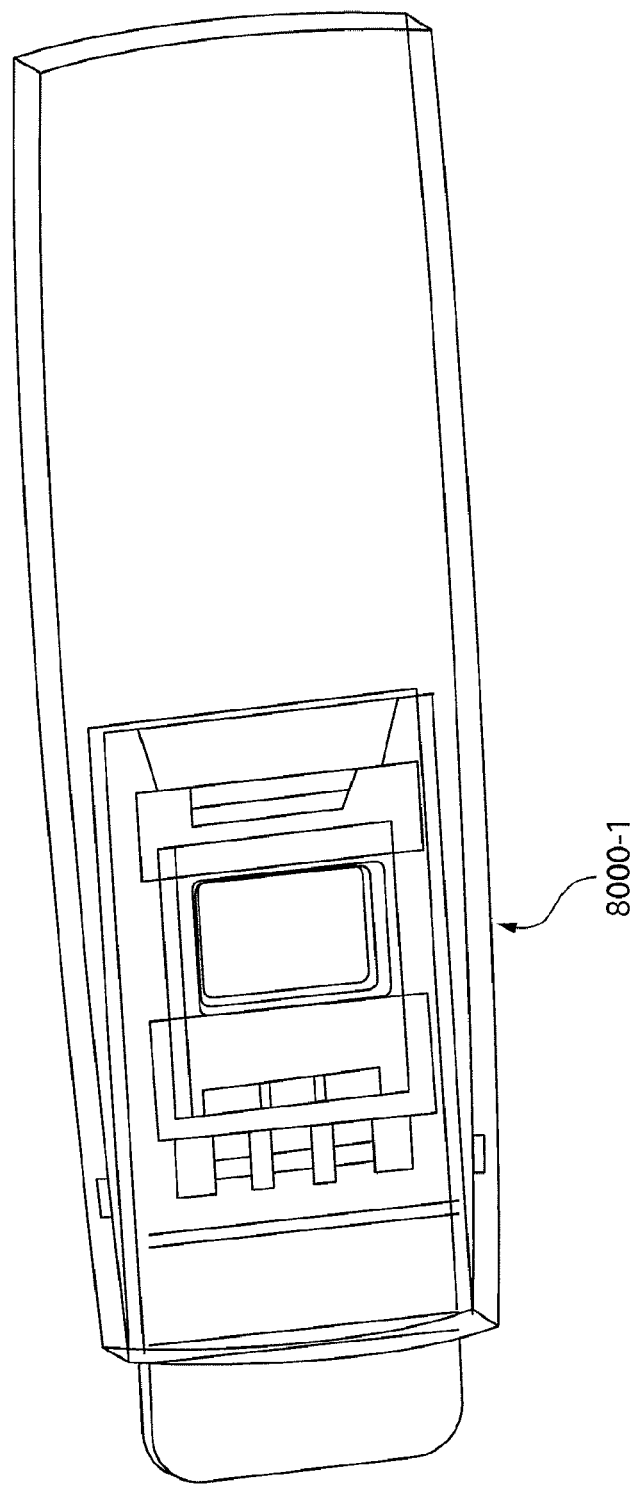
FIG. 25 illustrates a perspective view of an exemplary biomarker detector cartridge.
Figure 26:
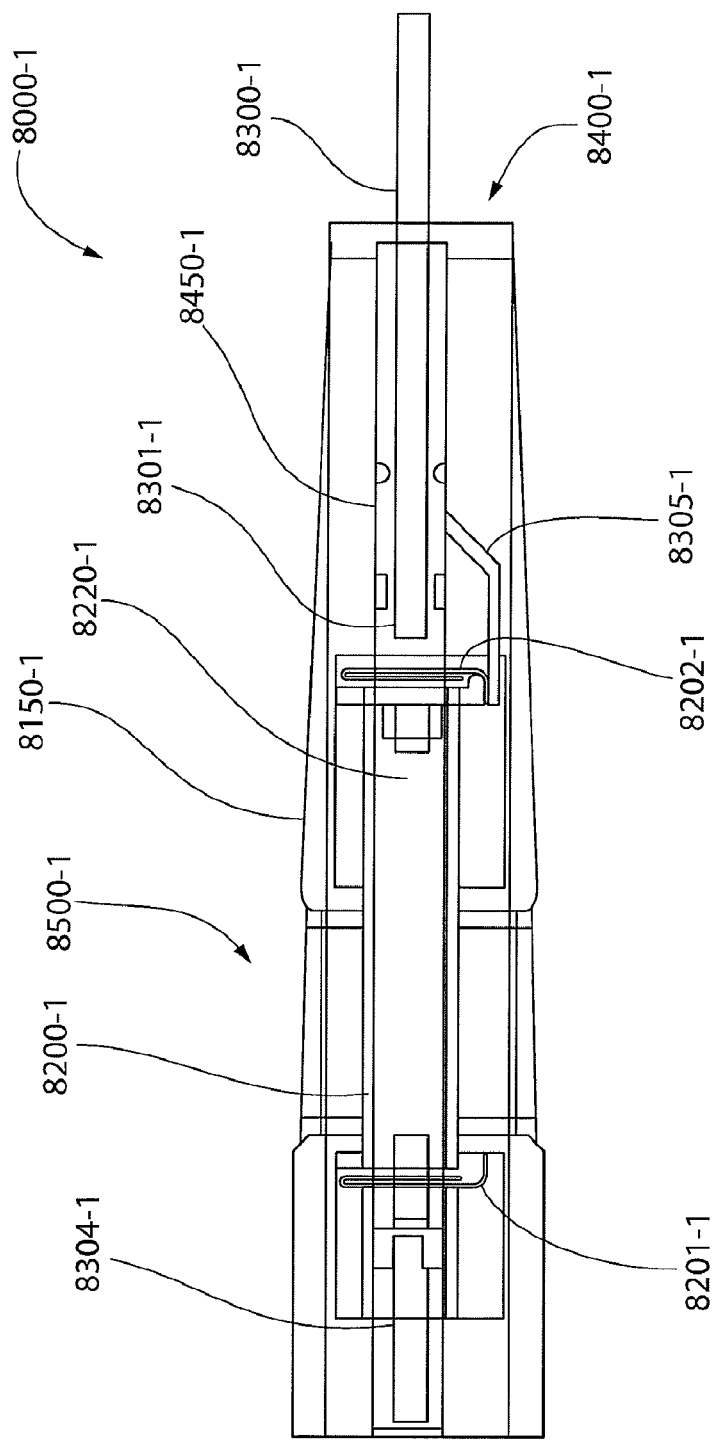
FIG. 26 illustrates internal components of the exemplary biomarker detector cartridge of FIG. 25.
Figure 27:
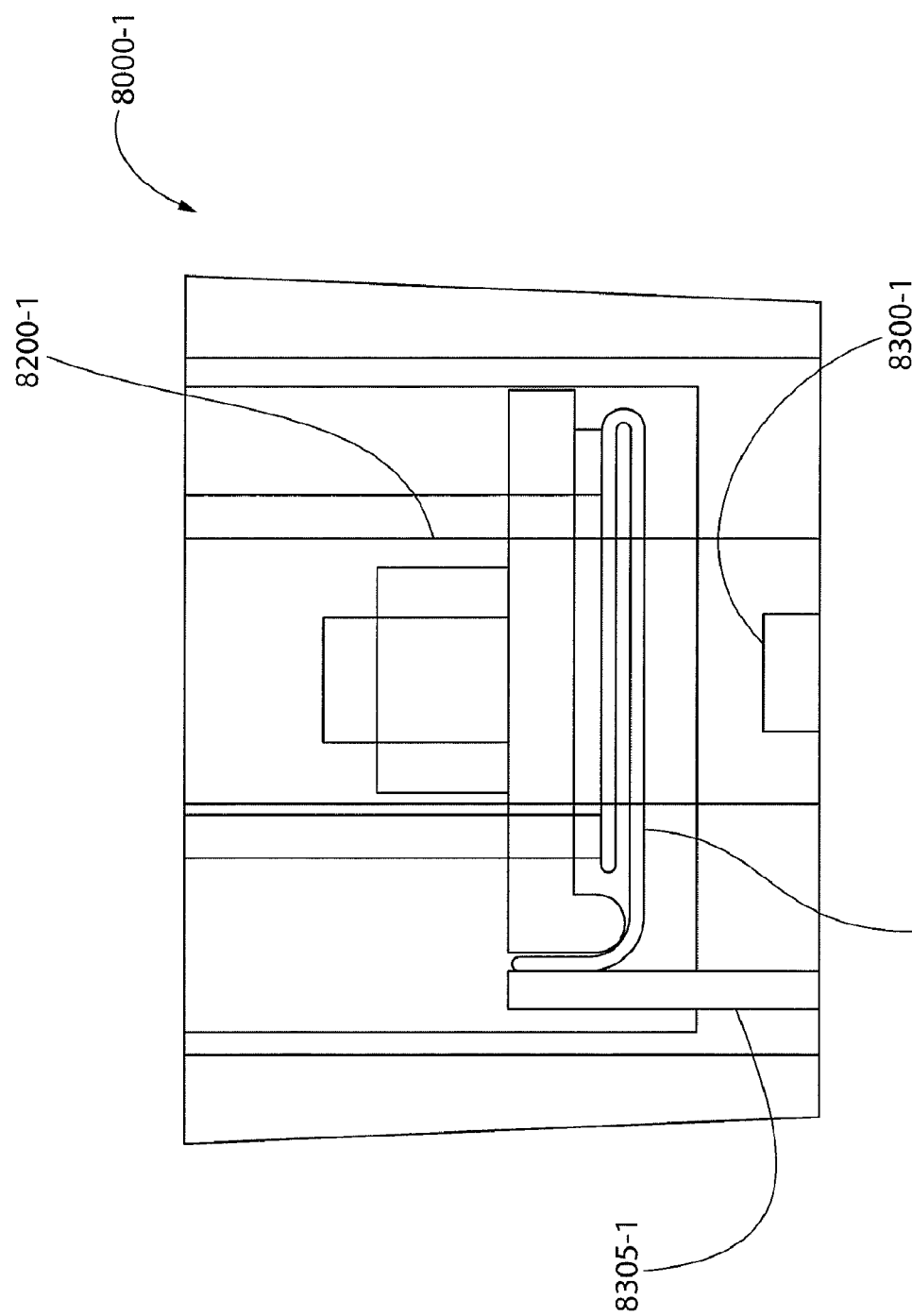
FIG. 27 illustrates internal components of the exemplary biomarker detector cartridge of FIG. 25.
Figure 28:
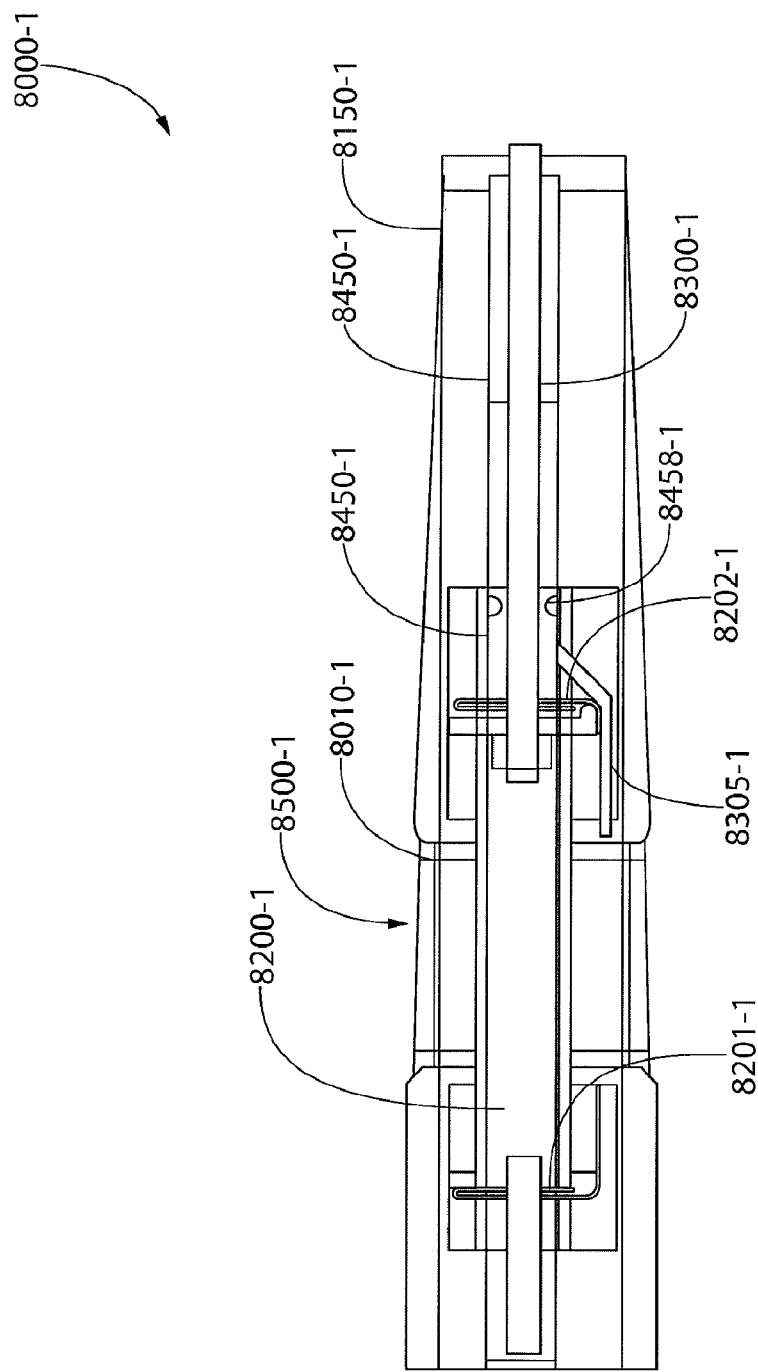
FIG. 28 illustrates internal components of the exemplary biomarker detector cartridge of FIG. 25.
Figure 29:
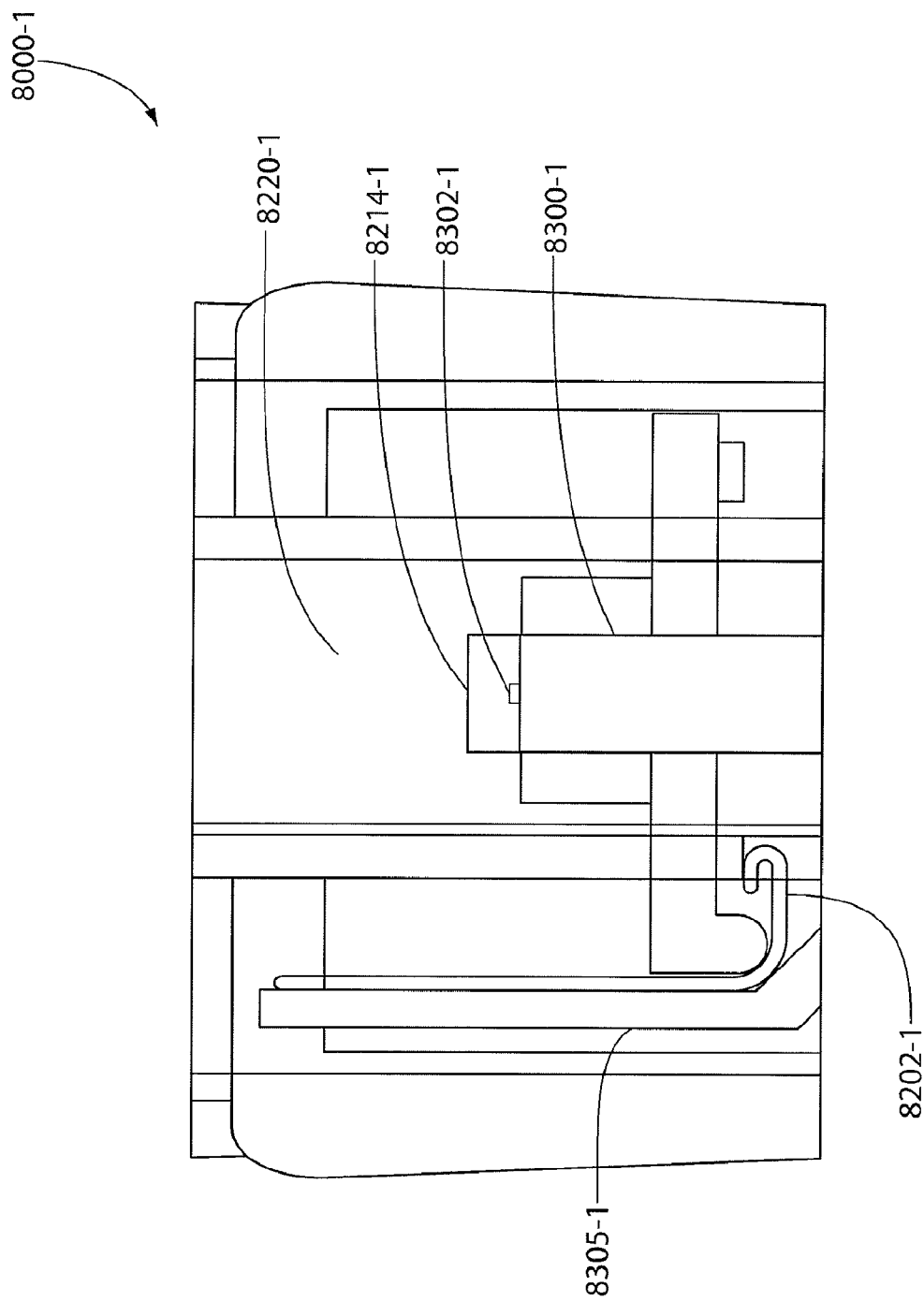
FIG. 29 illustrates internal components of the exemplary biomarker detector cartridge of FIG. 25.
Figure 30:
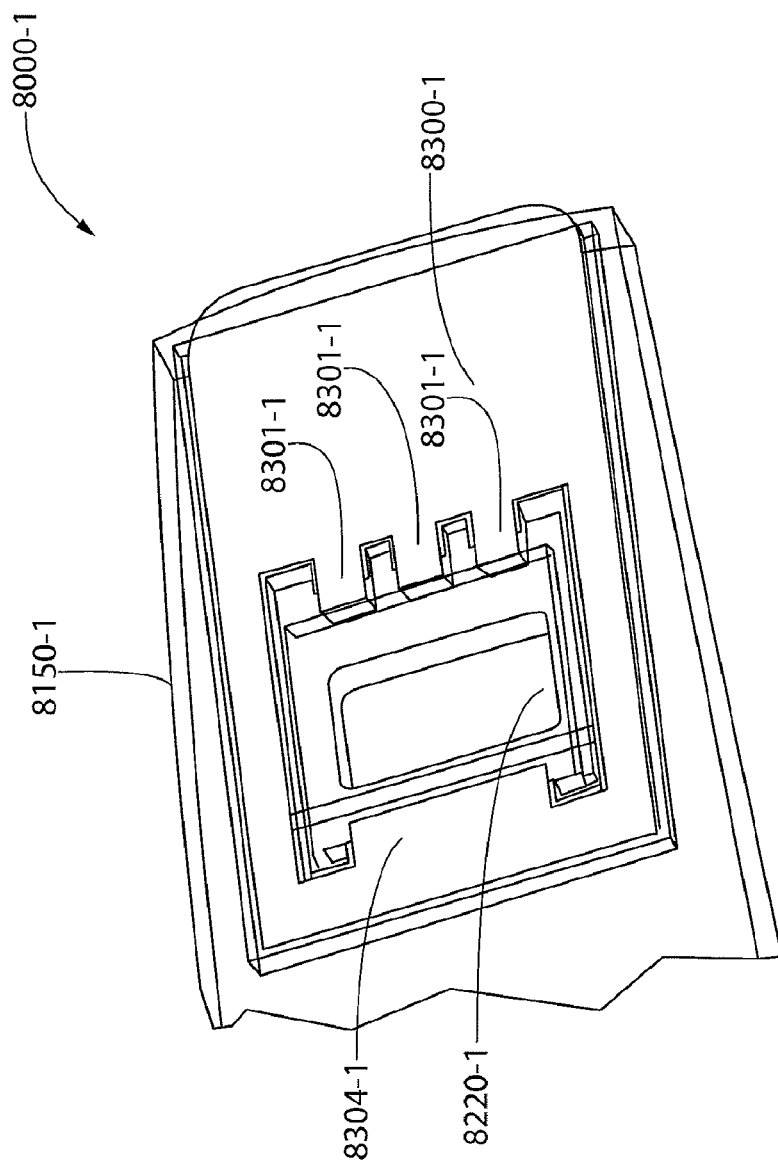
FIG. 30 illustrates internal components of the exemplary biomarker detector cartridge of FIG. 25.

In some embodiments, the biomarker detector cartridge 8000-1 may be provided where the sample portion 8400-1 is provided in a first position that may be moved to a second position. When the sample portion 8400-1 is in the first position, as shown in FIGS. 25-27, the fluid collector 8300-1 and connecting portion 8304-1 are disconnected from the separation medium 8220-1 and separated by seals 8201-1 and 8202-1. The seals 8201-1 and 8202-1 (e.g., foil seals) are provided to maintain the moisture of the separation medium 8220-1 and thereby prevent desiccation of the separation medium 8220-1 prior to use. Seal 8202-1 may be connected to a frame arm 8305-1 and seal 8201-1 may be connected to a portion of the cartridge body 8150-1 or the frame arm 8305-1. When the sample portion 8400-1 is moved to the second position, the seals 8201-1 and 8202-1 are withdrawn, as shown in FIGS. 28 and 29, and the separation medium 8220-1 may thereby be fluidly connected, or in contact with, the connecting portion 8304-1 and fluid collector 8300-1 through applicators 8301-1. In some embodiments, the sample portion 8400-1 may be moved from the first position to the second position upon insertion of the biomarker detector cartridge into a base as described herein.

In some embodiments, the applicators 8301-1 may include a reagent source 8302-1, which may be provided at the end of the applicator 8301-1. Additionally, the separation medium 8220-1 may include loading wells 8214-1. When the sample portion 8400-1 is moved from the first position (see FIG. 26) to the second position (see FIG. 29), the applicators 8301-1 may be provided at the loading wells 8214-1 and fluid received in the fluid collector 8300-1 may pass through the applicators 8301-1, dissolving the reagent from the reagent sources 8302-1 and delivering a mixture of the reagent and the collected fluid to a loading well 8214-1.

In another embodiment, frame 8450-1 may include a living hinge 8458, such that pressure applied to the body 8150-1, about the living hinge 8458, may result in a pumping of the fluid collected in the fluid collector 8300-1.

In an embodiment, the invention includes a biomarker detector cartridge 8000-2, as shown in FIGS. 31 to 35, wherein a sample portion 8400-2 may be connected by a snap fitting to the assay portion 8500-1.

Figures 31, 32A:
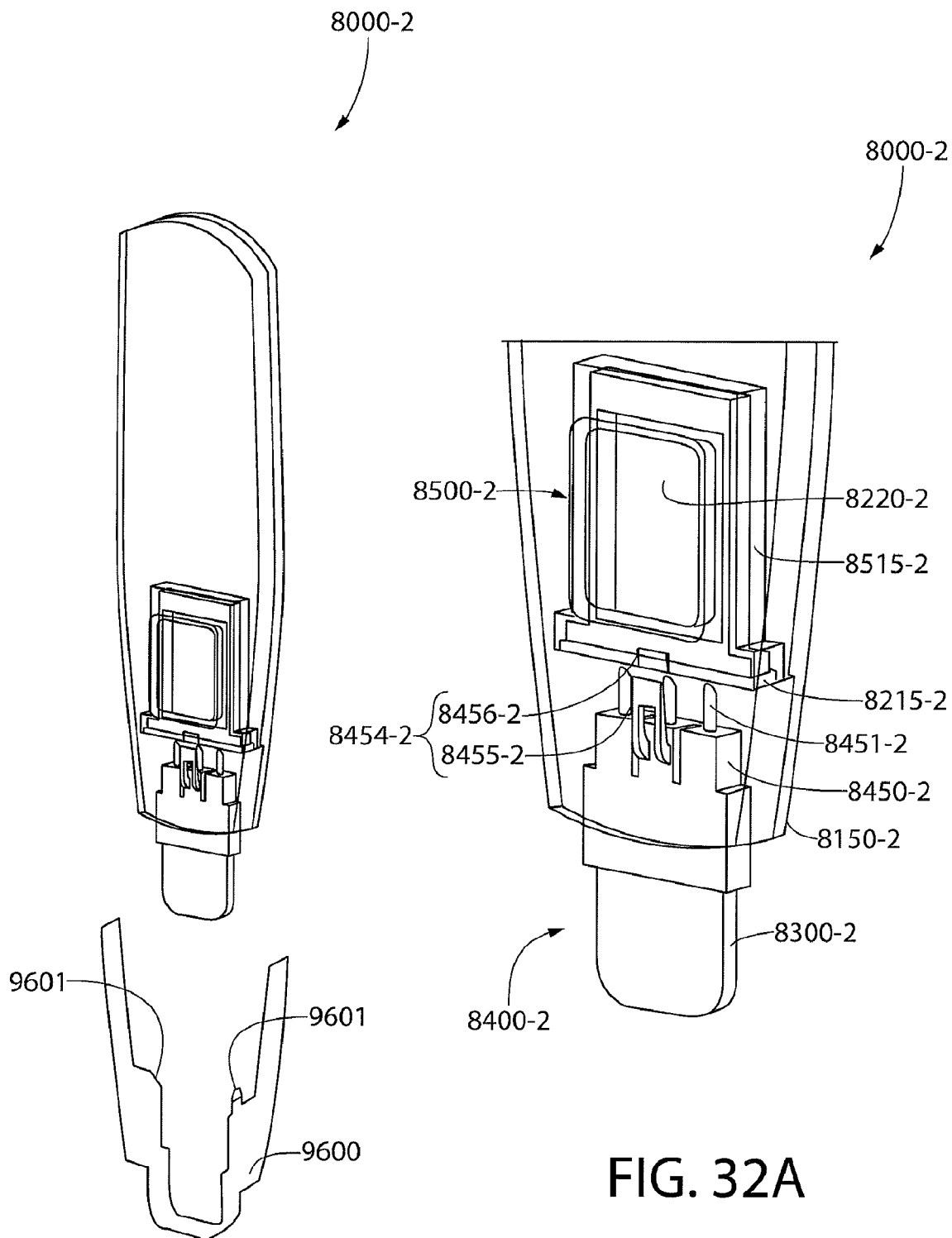
FIG. 31 illustrates an exemplary biomarker detector cartridge and a corresponding receiver portion of a base.
FIGS. 32A and 32B illustrate internal components of the exemplary biomarker detector cartridge of FIG. 31 (FIG. 32A) and a close up perspective view of a latching feature of the exemplary biomarker detector cartridge of FIG. 31 (FIG. 32B)
Figure 32B:
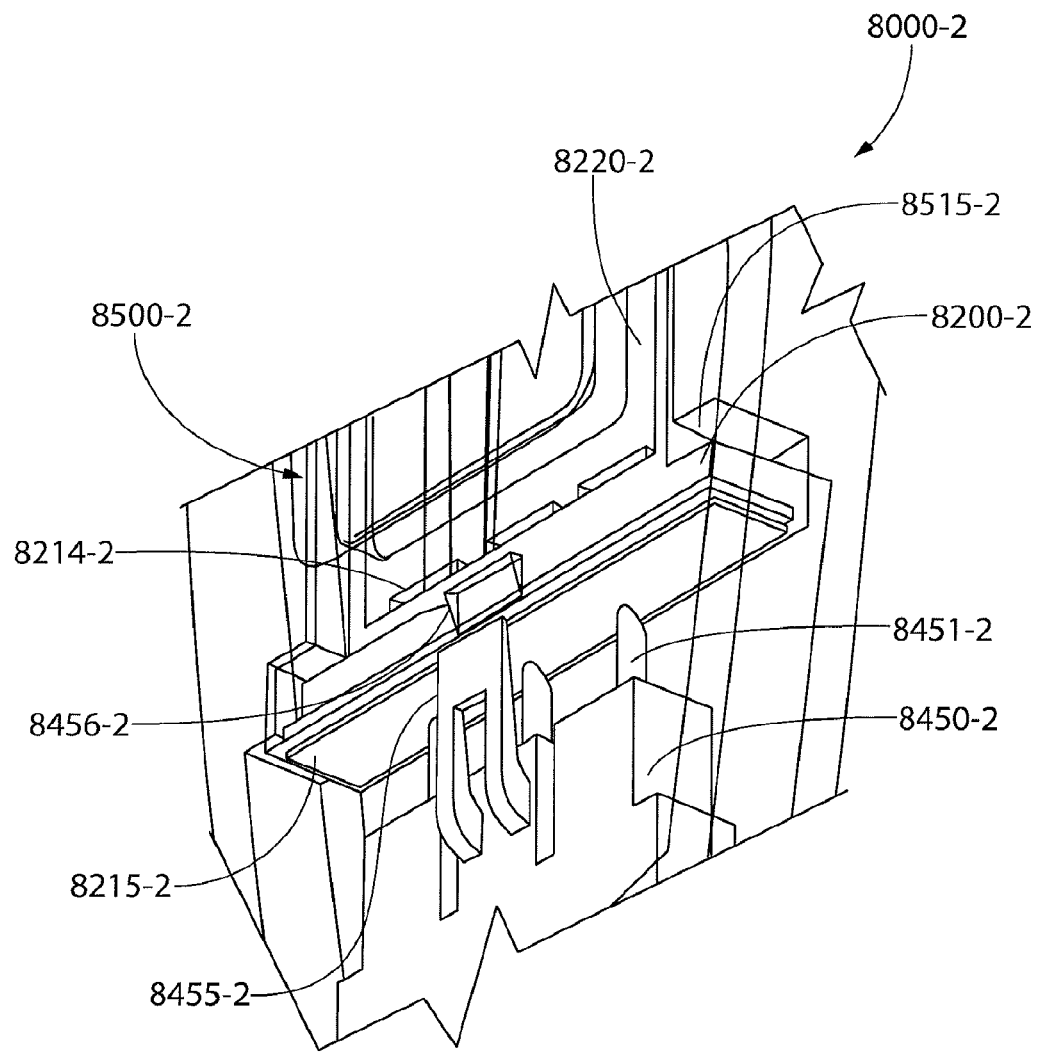

As shown in FIGS. 32A and 32B, the biomarker detector cartridge 8000-2 may have a cartridge body 8150-2 having a sample portion 8400-2 and an assay portion 8500-2.

As shown in FIGS. 32A and 32B, the biomarker detector cartridge 8000-2 may include a cartridge body 8150-2 having windows 8010 that may cover the assay portion 8500-2 at apertures 8140-2 and 8141-2 (shown in FIG. 34).

As shown in FIGS. 32 to 35, the sample portion 8400-2 may include a fluid collector 8300-2, which may be connected to the cartridge body 8150-2 through a frame 8450-2. With regard to FIGS. 32 to 35, the frame 8450-2 may include a number of cannula 8451-2 (e.g., three cannulas), which may be in fluidic communication with the fluid collector 8300-2 disposed within the frame 8450-2 through the fluid collector applicators 8301-2. The sample portion 8500-2 may include a reagent source 8302-2 (e.g., a dried reagent source such as dried nanoswitches), which may be disposed at the applicators 8301-2 of the fluid collector 8300-2. The reagent source 8302-2 may be disposed at the end of the applicators 8301-2 such that as fluid is received at the fluid collector 8300-2, the fluid may flow through the applicators 8301-2 and dissolve the reagent source 8302-2 before passing through the cannulas 8451-2.

The assay portion 8500-2 may include an assay platform 8515-2 upon, which may include an electrophoretic cell 8200-2. The electrophoretic cell 8200-2 may include a separation medium 8220-2, which may include one or more loading wells 8214-2 (e.g., three loading wells) that may correspond to cannulas 8451-2. As shown in FIG. 34, the electrophoretic cell 8200-2 may include a foam 8217-2 that may abut or connect to an end of the separation medium 8220-2 opposite the end that faces the cannulas 8451-2. The foam 8217-2 may be an electrolysis bubble management foam. The electrophoretic cell 8200 may also include an electrode 8521-2, which may be a cathode, that may be provided in electrical communication with the separation medium 8220. The electrophoretic cell 8200-2 may further include an electrode 8522-2, which may be an anode, that may be provided in electrical communication with the separation medium 8220-2.

The assay portion 8500-2 may include a seal 8215-2 (e.g., foil) that may be placed over the loading wells 8214-2 of the separation medium 8220-2 to maintain the moisture of the separation medium 8220-2 and thereby prevent desiccation of the separation medium 8220-2 prior to use.

Figure 33:
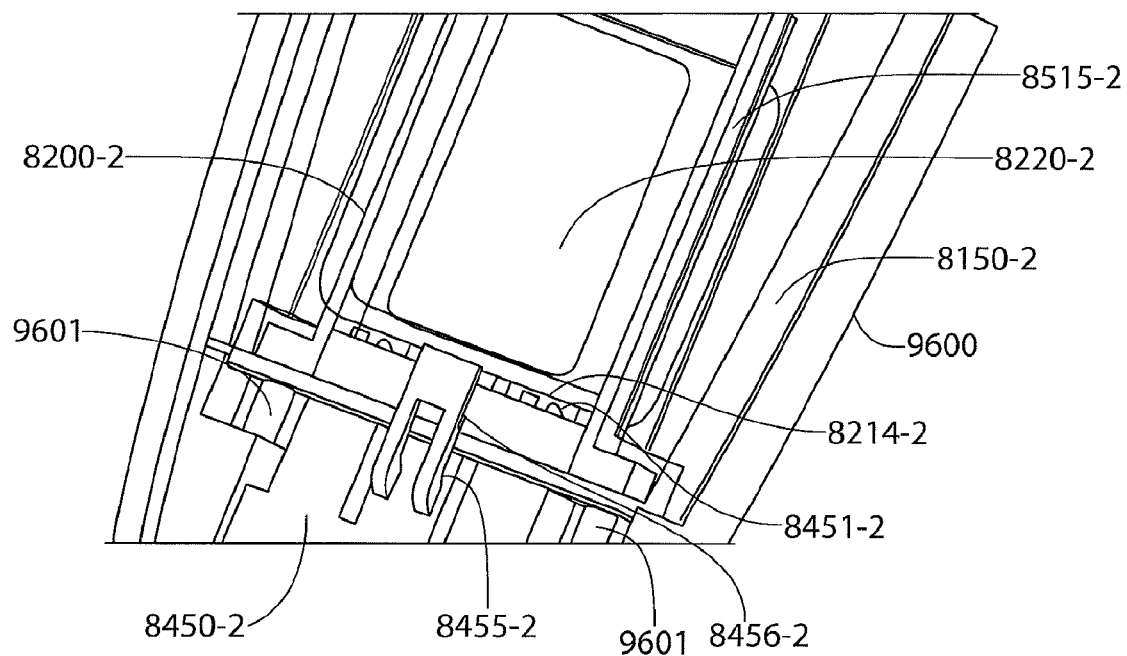
FIG. 33 illustrates internal components of the exemplary biomarker detector cartridge of FIG. 31.

As shown in FIGS. 32B and 33, the frame 8450-2 may be movable between a first position (i.e., a non-analysis position as shown in FIG. 32B) and a second position (i.e., an analysis position as shown in FIG. 33).

Furthermore, the biomarker detector cartridge 8000-2 may include a connector 8454-2 provided for connecting sample portion 8400-2 to the assay portion 8500-2. The connector 8454-2 may include a clasp 8455-2 and a latch 8456-2, where the clasp 8455-2 may engage the claps 8456-2. In some embodiments, the latch 8456-2 may be disposed at the frame 8450-2 and the clasp 8456-2 may be provided at the assay platform 8515-2.

In an embodiment, a base described herein may include a cartridge contact section 9600, which may be shaped to abut a portion of the frame 8450-2 and/or the cartridge body 8150-2. The cartridge contact section 9600 may include electrical contacts 9601. In some embodiments, the biomarker detector cartridge 8000-2 may be provided to a base described herein having a cartridge contact section 9600, which may force the frame 8450-2 from the first position to the second position and engage the electrodes of the biomarker detector cartridge 8000-2.

In the first position (FIG. 32A), fluid may be collected at the fluid collector 8300-2 prior to analysis. A user may then insert the biomarker detector cartridge 8000-2 into a base having cartridge contact section 9600, which may then force the frame 8450-2 into the second position (FIGS. 33-35) whereby the cannulas 8451-2 pierce the seal 8215-2 and may deposit a mixture of fluid collected at the fluid collector 8300-2 and reagent from the reagent source 8302-2 at the loading wells 8214-2. In some embodiments, the electrical contacts 9601 may then contact electrodes 8521-2 and 8522-2, in order to provide an electrical current to the separation medium 8220-2. Indeed, in the second position of the frame 8450-2, the electrodes 8521-2 and 8522-2 may be in electrical communication with the electrophoretic cell 8200-2, and may thereby provide a selected potential across the separation medium 8220-2. In some embodiments, the electrode 8521-2 may serve as an anode while electrode 8522-2 may serve as a cathode.

In an embodiment, as shown in FIGS. 36 to 42, the invention includes biomarker detector cartridge 8000-3 and base 9000-1. The biomarker detector cartridge 8000-3 includes a pull tab that allows for the removal of a seal that separates the assay portion and the sample portion.

Figure 38:
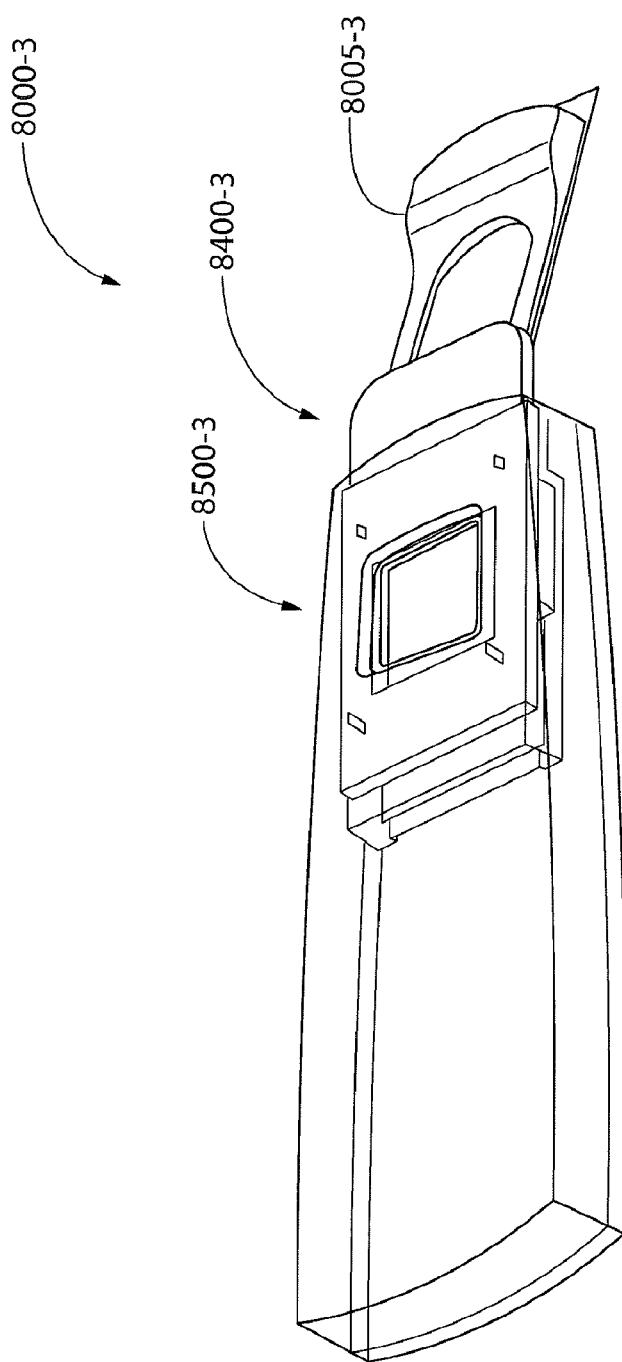
FIG. 38 illustrates internal components of the exemplary biomarker detector cartridge of FIG. 36.

As shown in FIG. 38, the biomarker detector cartridge 8000-3 may include a sample portion 8400-3 and an assay portion 8500-3. In some embodiments, the sample portion 8400-3 and assay portion 8500-3 may be separated by a seal 8005-3 that may include a pull tab portion. In some embodiments, the seal may be removed by a user grasping the pull tab portion of the seal 8005-3 and removing the seal 8005-3 from the biomarker detector cartridge 8000-3 to allow the sample portion 8400-3 to contact the assay portion 8500-3.

Figure 39:
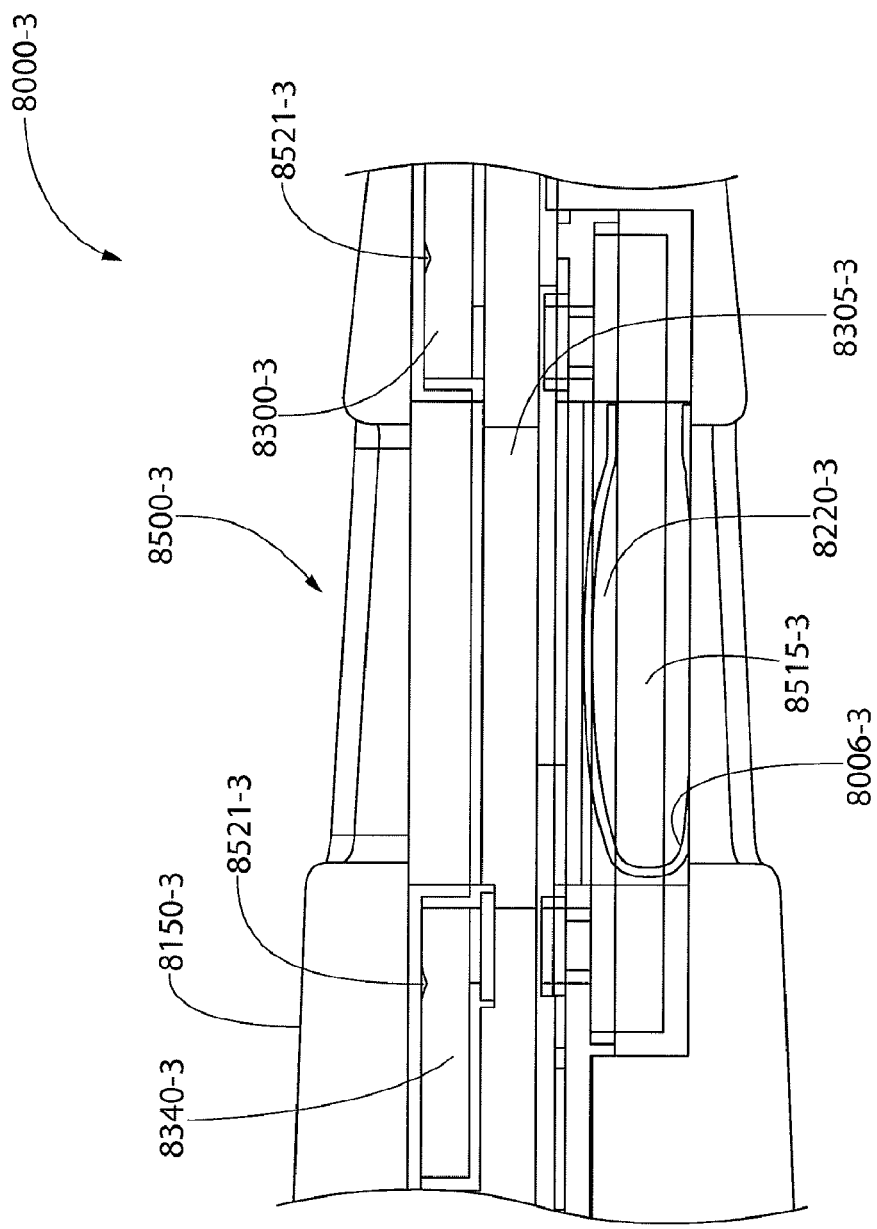
FIG. 39 illustrates internal components of the exemplary biomarker detector cartridge of FIG. 36.

As shown in FIG. 39, the biomarker detector cartridge 8000-3 is shown with the seal 8005-3 in place and the fluid collector 8300-3, and contact portion 8340-3 of the fluid collector 8300-3, separated from the separation medium 8220-3 of the assay portion 8500-3. In some embodiments, a spring 8006-3 (e.g., a gel case motion spring) is included in the cartridge body 8150-3, which is provided to apply pressure to bias the separation medium 8220-3 toward the fluid collector 8300-3 and contact portion 8340-3, such that the separation medium 8220-3 is placed in fluid communication with the fluid collector 8300-3 and the contact portion 8340-4. In some embodiments, the assay portion 8500-3 includes an assay platform 8515-3, which may support the separation medium 8220-3.

In some embodiments, the biomarker detector cartridge 8000-3 may include electrodes 8532-3, which may be disposed at the fluid collector 8300-3 and contact portion 8340-3.

Figure 40:
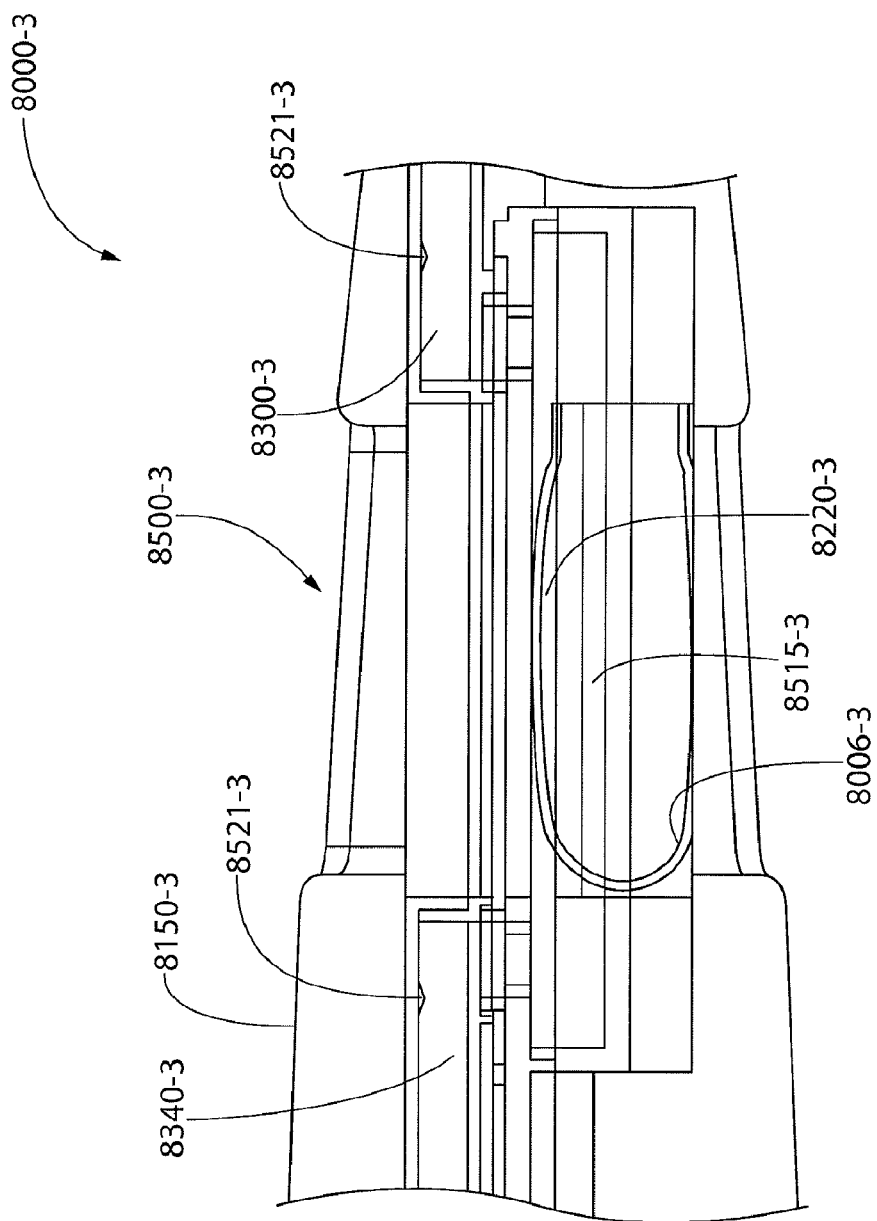
FIG. 40 illustrates internal components of the exemplary biomarker detector cartridge of FIG. 36.

In FIG. 40, the seal 8005-3 has been removed and the separation medium 8220-3 is biased to connect to the fluid collector 8300-3 and the contact portion 8340-3, such that the separation medium 8220-3 is placed in fluid communication with the fluid collector 8300-3 and the contact portion 8340-4.

In some embodiments of the biomarker detector cartridge 8000-3, electrolyte foam may be avoided in the cartridge. In some embodiments, the fluid collector 8300-3 remains in fixed position and does not move relative to the cartridge body 8150-3.

Figure 41:
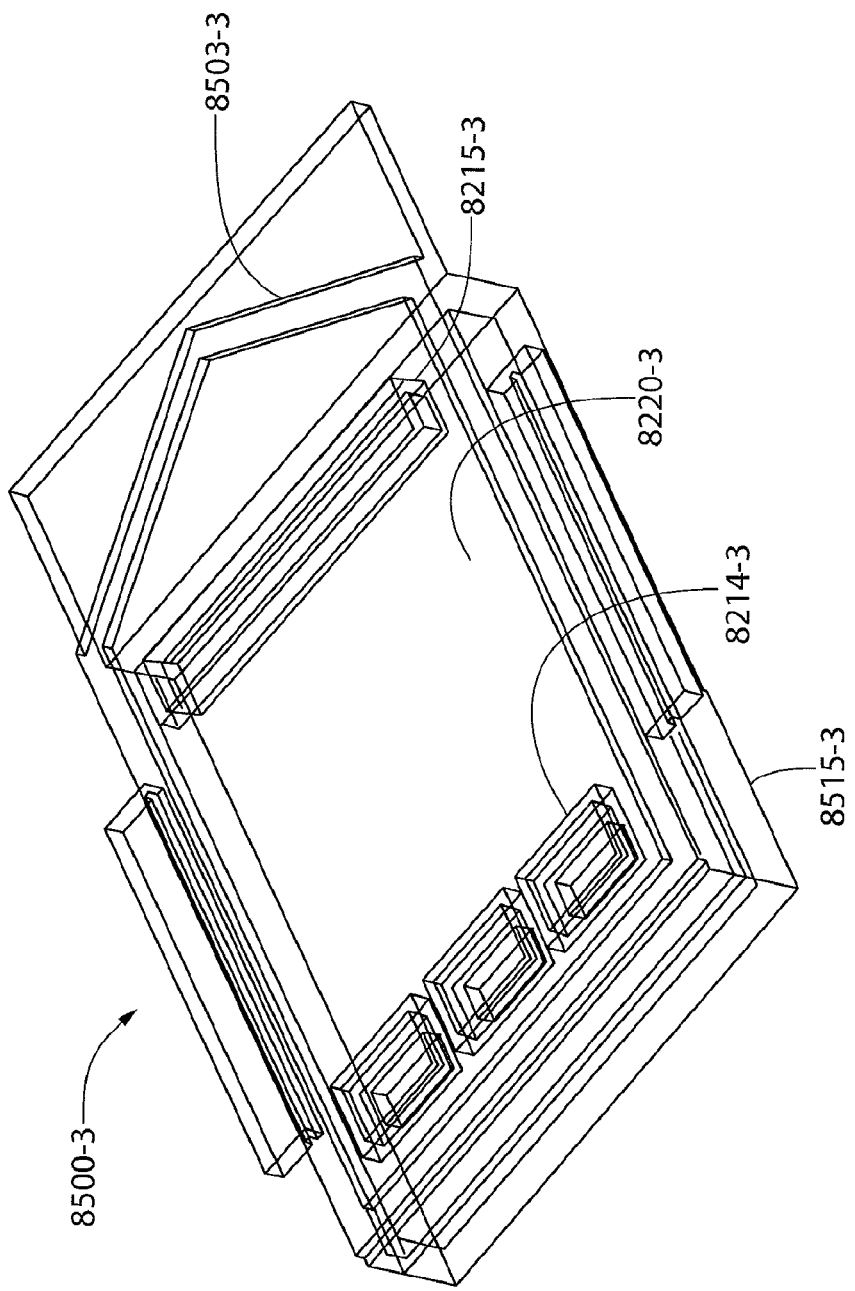
FIG. 41 illustrates an assay portion of the exemplary biomarker detector cartridge of FIG. 36.
Figure 42:
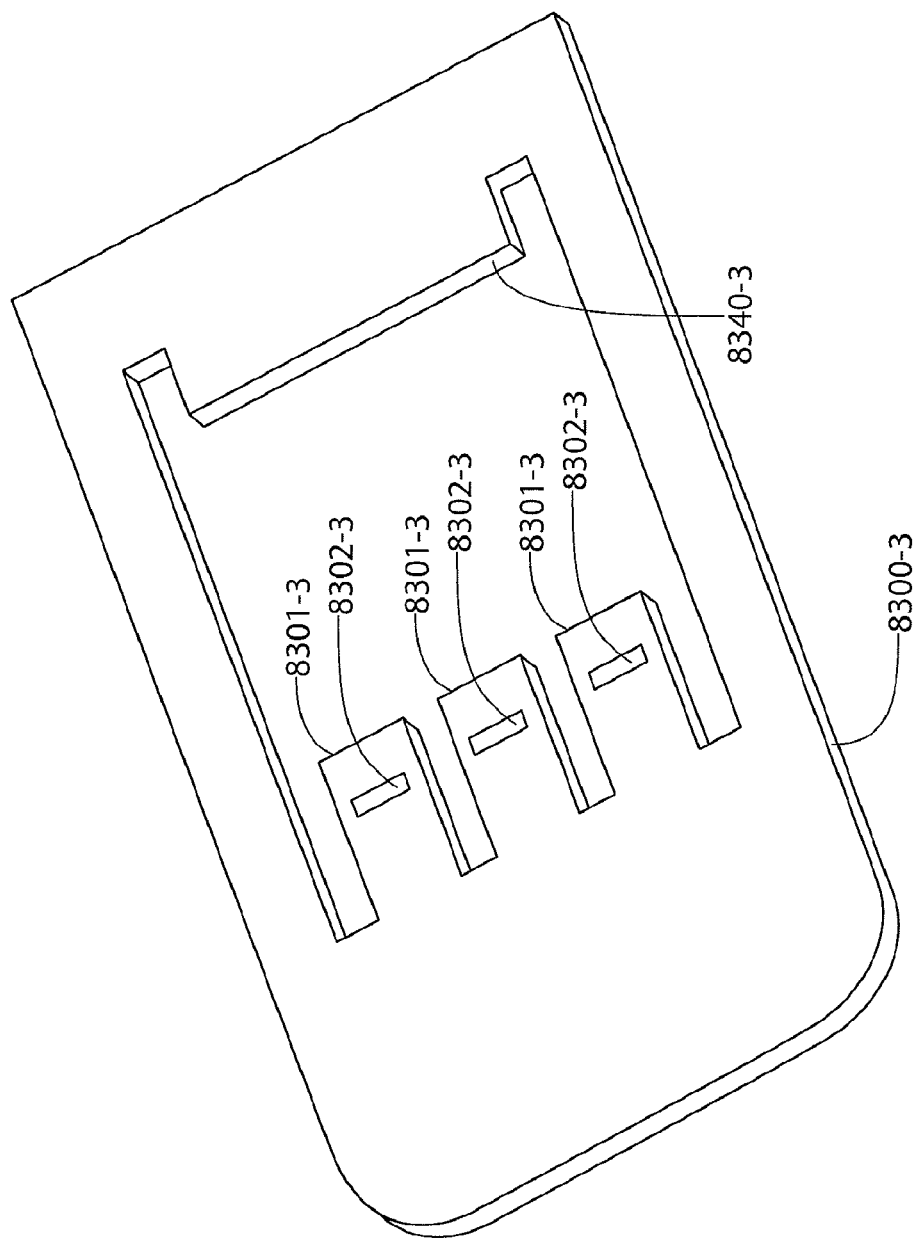
FIG. 42 illustrates a fluid collector of the exemplary biomarker detector cartridge of FIG. 36.

As shown in FIGS. 41 and 42, the assay portion 8500-3 includes an assay platform 8515-3 upon which may be connected a separation medium 8220-3. The separation medium 8220-3 may include loading cells 8214-3 that may be provided to connect to applicators 8301-3. The separation medium 8220-3 may include a transfer portion 8215-3 that may be provided to connect to contact portion 8340-3. In some embodiments, the applicators 8301-3 may include reagent sources 8302-3 (e.g., sources of nanoswitches, as described herein).

In some embodiments, as shown in FIG. 41, the assay portion 8500-3 may include chevron portions 8503-3, which may allow for the reduction or removal of seal forces at the time of removal of the seal 8005-3.

In some embodiments, as shown in FIGS. 36 and 37, the biomarker detector cartridge 8000-3 may be analyzed in conjunction with base 9000-1. Base 9000-1 may include a receiver 9152-1 provided to receive a portion of the biomarker detector cartridge 8000-3. The base 9000-1 may include a light source (e.g., LED light source) 9210-1 and an optical detector 9200 provided to receive light transmitted through the assay portion 8500-3 from the light source 9210-1. The base 9000-1 may include a plug 9011-1 that may be in electrical communication with a power supply, controller, optical detector 9200-1, and light source 9210-1, in a manner as described herein. The base 9000-1 may further include electrodes 9061-1, which may be provided to communicate with electrodes 8521-3 of the biomarker detector cartridge 8000-3 and thereby provide an electric current to the assay portion 8500-3. In FIGS. 36 and 37, the biomarker detector cartridge 8000-3 is shown with the seal 8005-3 removed.

In an embodiment, the invention includes a biomarker detector cartridge 10000 as shown in FIGS. 43 to 48 that provides self-forming wells within a separation medium.

Figure 43:
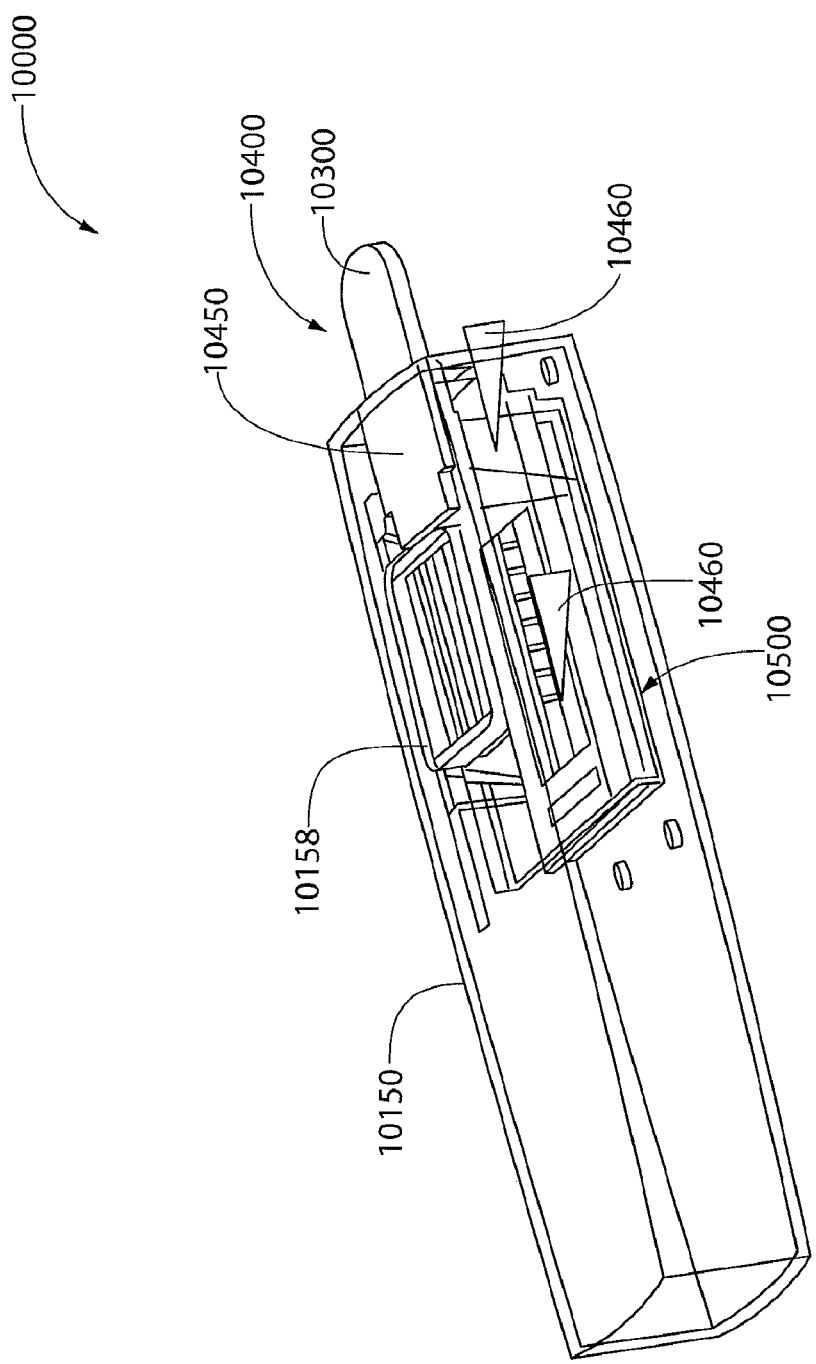
FIG. 43 illustrates internal components of an exemplary biomarker detector cartridge.
Figure 44:
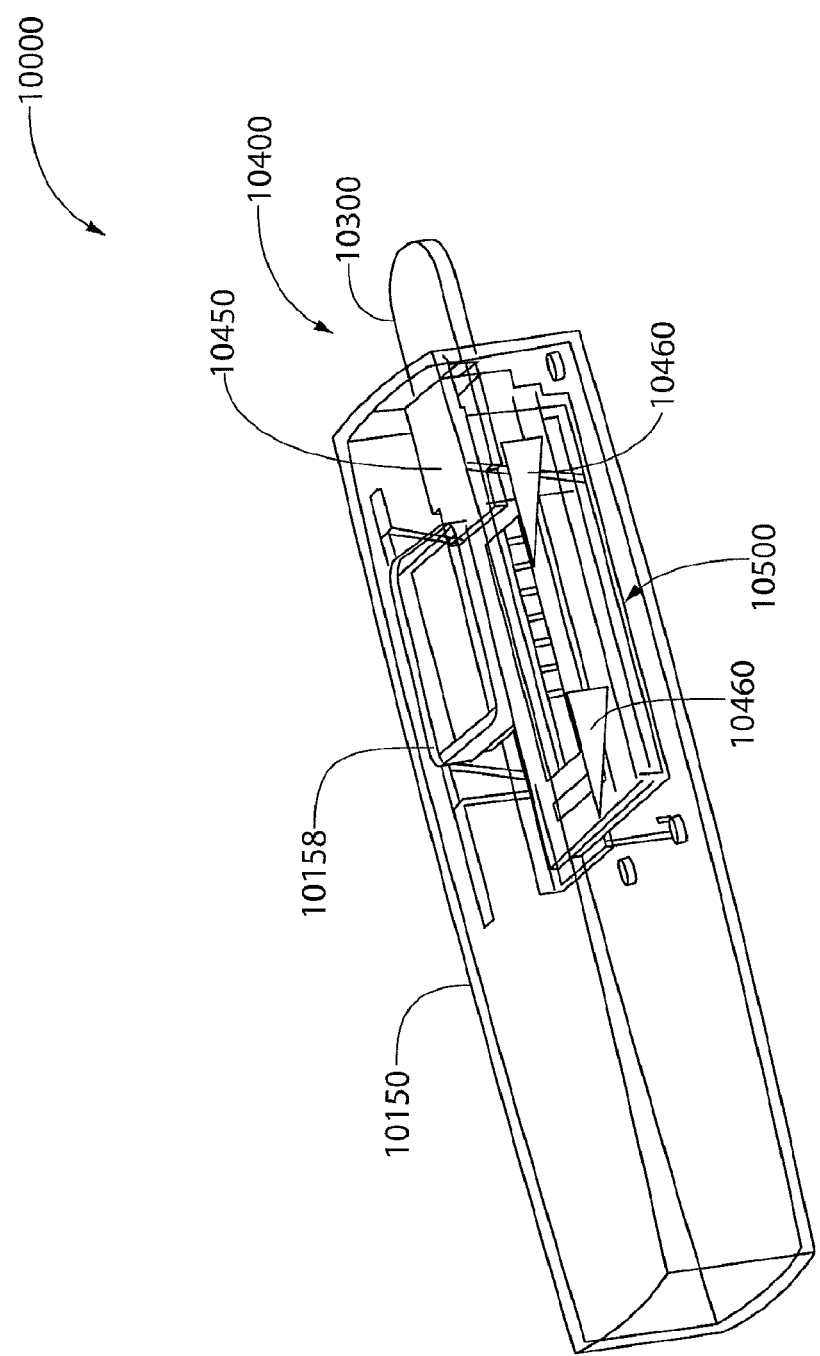
FIG. 44 illustrates internal components of the exemplary biomarker detector cartridge of FIG. 43.

FIGS. 43 and 44 depict biomarker detector cartridge 10000 having a cartridge body 10150 with a sample portion 10400 and an assay portion 10500. In some embodiments, the cartridge body may include apertures 10157 and 10158 proximate to the assay portion 10500. In some embodiments, the sample portion 10400 may include a fluid collector 10300 and a frame 10450 that may connect to the fluid collector 10300. In addition, the cartridge body 10150 may include a cam assembly 10460, which may be provided to bias the sample portion 10400 toward the assay portion 10500. In some embodiments, the cam assembly 10460 is a linear cam assembly. In FIG. 43, the assay portion 10500 is separated from the sample portion 10400. In FIG. 44, the cam assembly 10460 is actuated and the sample portion 10400 is biased toward the assay portion 10500 such that the assay portion 10500 may be in fluid communication with the sample portion 10400.

Figure 45:
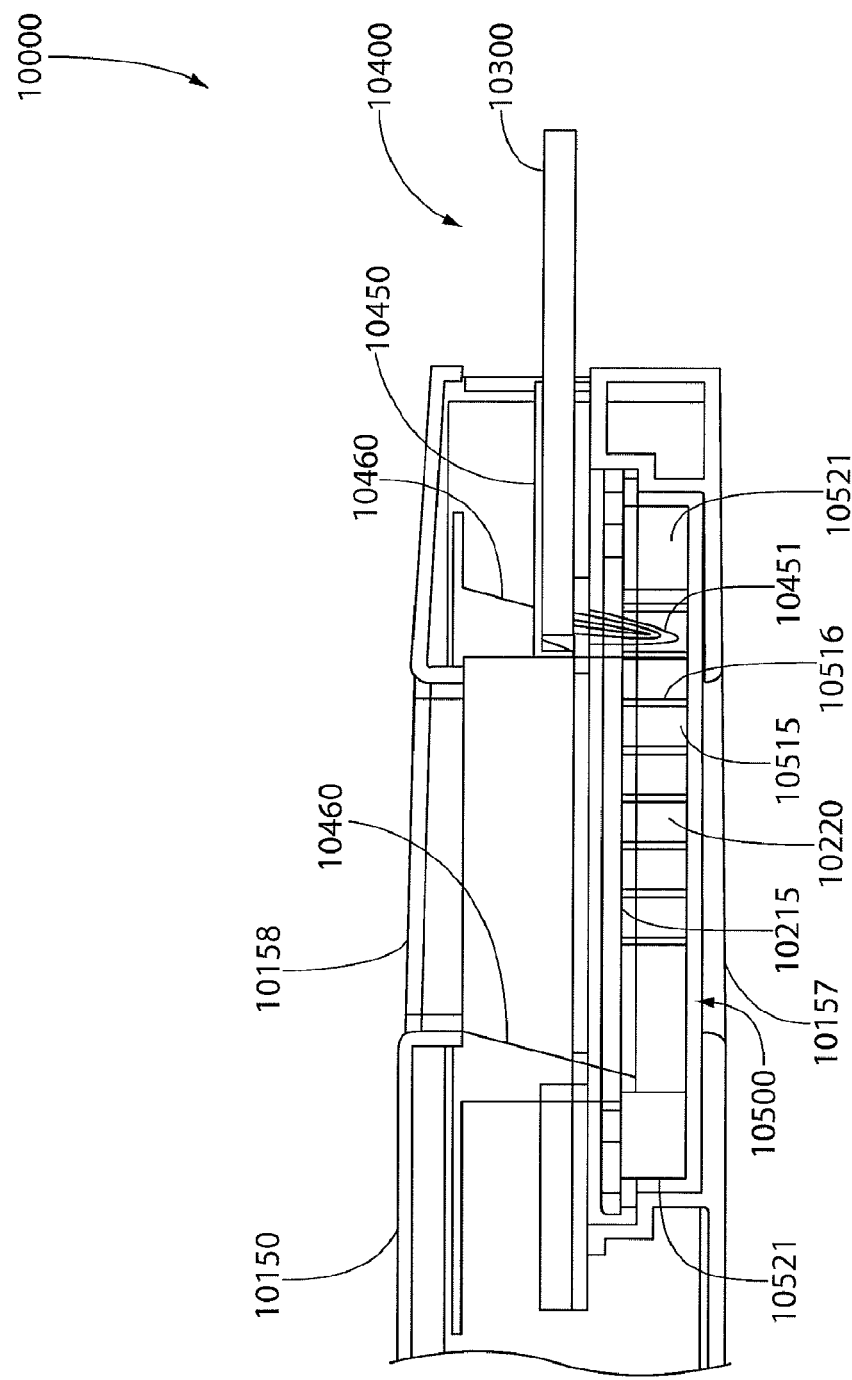
FIG. 45 illustrates internal components of the exemplary biomarker detector cartridge of FIG. 43.

FIG. 45 depicts biomarker detector cartridge 10000 with the cam assembly 10460 actuated to bias the sample portion 10400 into contact with the assay portion 10500. In certain embodiments, the sample portion 10400 includes a frame 10450 having cannulas 10451. The assay portion 10500 may include a seal 10215 (e.g., a foil seal) that may cover a separation medium 10220 and prevent desiccation of the separation medium 10220. Upon actuation of the cam assembly 10460, the cannulas 10451 may puncture the seal 10215 and prepare loading wells in the separation medium 10220.

Figure 46:
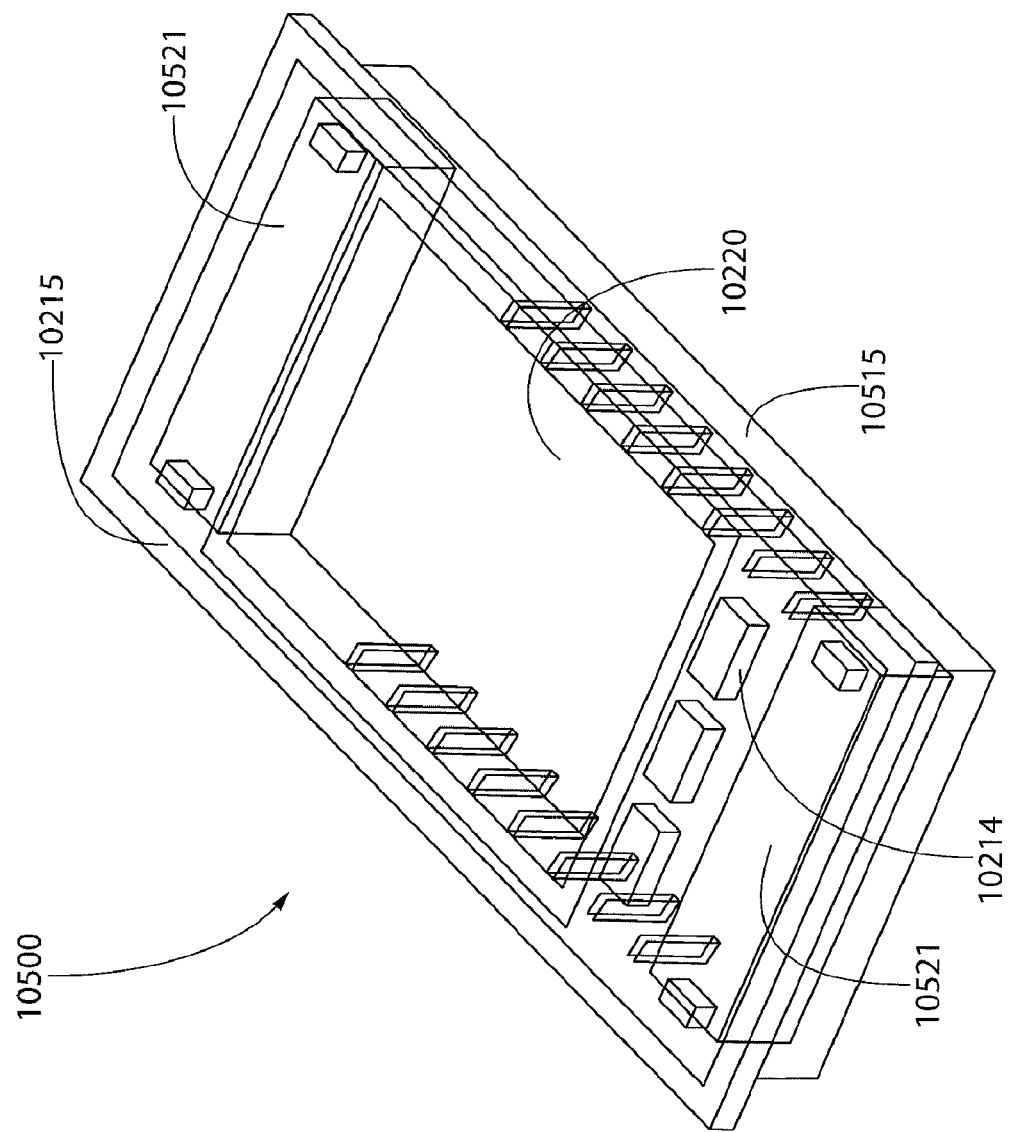
FIG. 46 illustrates an assay portion of the exemplary biomarker detector cartridge of FIG. 43.

FIGS. 45 and 46 depict the assay portion 10500, which may have a separation medium 10220 connected to an assay platform 10515. In some embodiments, the separation medium 10220 may include ribs 10516 which may be provided prevent motion of the separation medium 10220 during use and transport. In some embodiments, the assay portion 10500 may include a seal 10215 that may cover and may be sealed about the assay portion 10500 to cover the separation medium 10220. The assay portion 10500 may include loading well slots 10214, which may be punctured by cannulas 10451 upon actuation of the cam assembly 10460. In some embodiments, assay portion may include electrodes 10521, which may be disposed in fluid communication with the separation medium 10220. In some embodiments, the electrodes 10521 may be provided as cathode or anode foams that may include an electrolyte and an electrode assembly for providing an electrical potential across the separation medium 10220.

Figure 47:
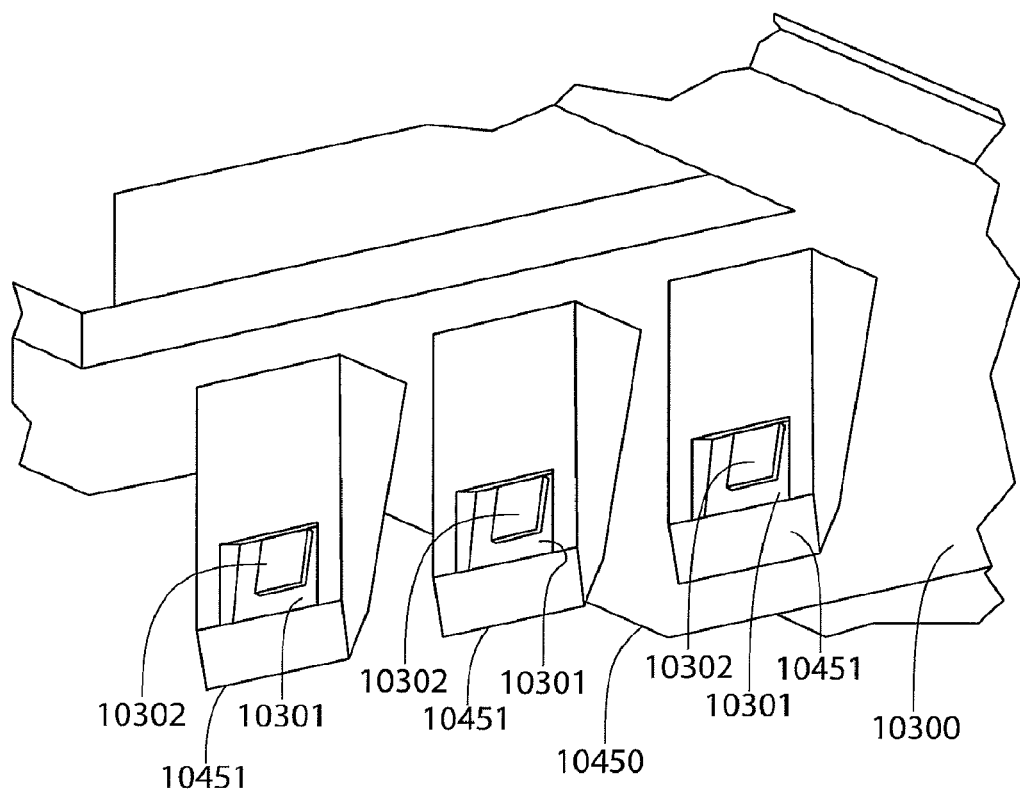
FIG. 47 illustrates a frame of the exemplary biomarker detector cartridge of FIG. 43.
Figure 48:
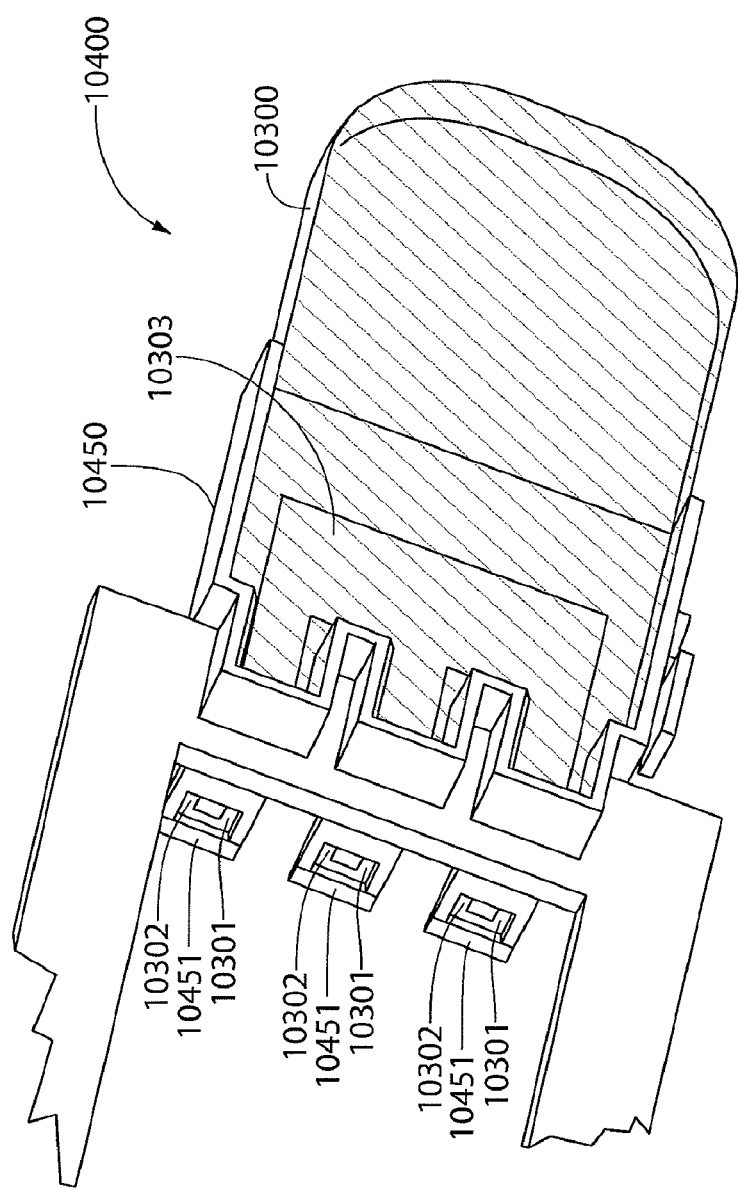
FIG. 48 illustrates a sample portion of the exemplary biomarker detector cartridge of FIG. 43.

FIGS. 45 to 48 depict the sample portion 10400, which may include a frame 10450 and cannulas 10451. As described herein, the cannulas 10451 may puncture the seal 10215 at loading well slots 10214 to provide loading wells at the separation medium 10220. As shown in FIGS. 47 and 48, the frame 10450 may include a fluid transfer material 10303 in fluid communication with the fluid collector 10300 to transfer fluid collected at the fluid collector 10300 through the cannulas 10301. In some embodiments, the fluid transfer material 10303 may be filter paper and/or may have the same composition as the fluid collector 10300. Furthermore, the fluid transfer material 10303 may include applicators 10301 that may project through the cannulas 10451. In some embodiments, the reagent source 10302 may be provided on applicators 10301. In some embodiments, the reagent source may include a source of nanoswitches. In some embodiments, the cannulas 10451 provide loading wells in the separation medium 10220 having a uniform wall.

Figure 49:
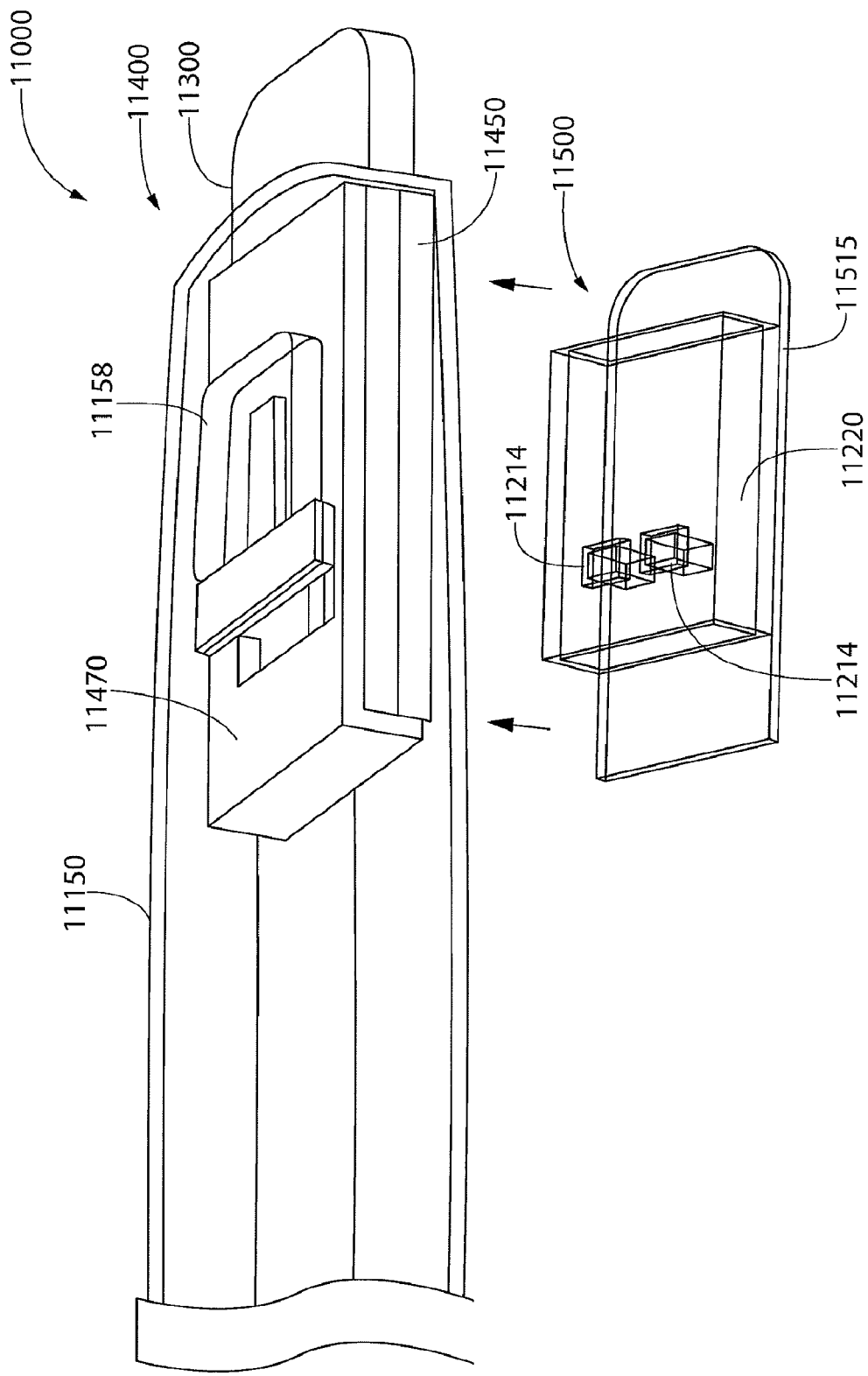
FIG. 49 illustrates an exemplary biomarker detector cartridge.
Figure 50:
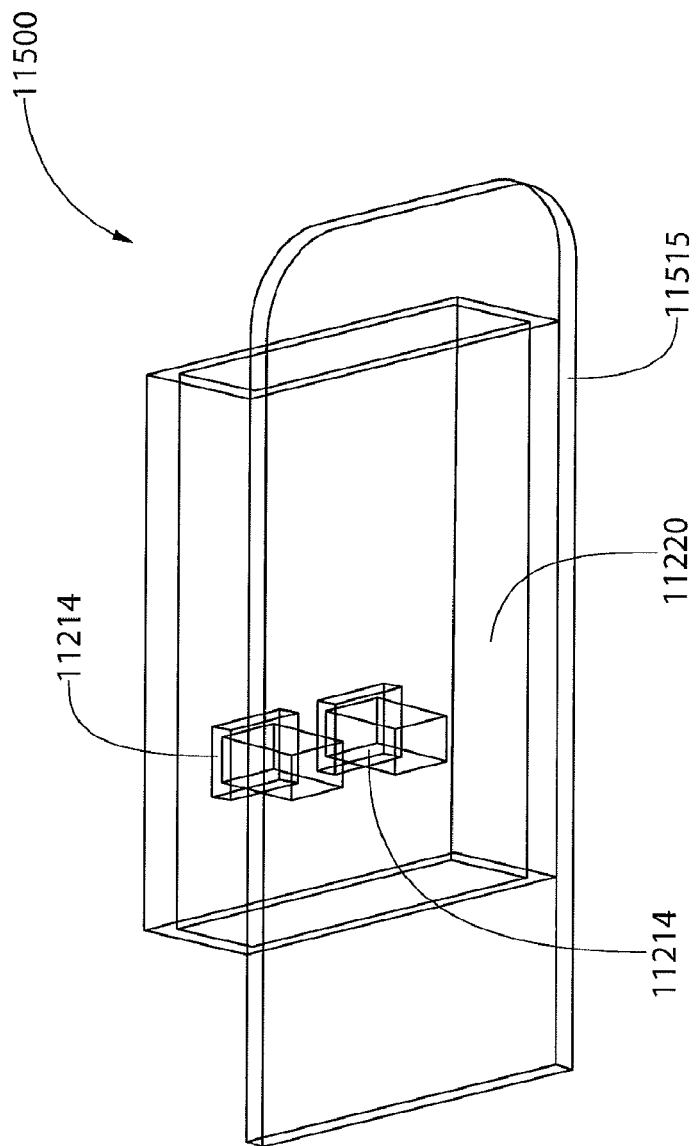
FIG. 50 illustrates an assay portion of the exemplary biomarker detector cartridge of FIG. 49.

In an embodiment, the invention includes a biomarker detector cartridge 11000 as shown in FIGS. 49 to 51 that provides a bridge manifold assembly where the assay portion is stored separately from the cartridge body.

FIG. 49 depicts a biomarker detector cartridge 11000 having cartridge body 11150, an aperture 11158, and a sample portion 11400. In some embodiments, the biomarker detector cartridge 11000 may include an assay portion 11500, which may be inserted into the cartridge body 11150.

Figure 51A:
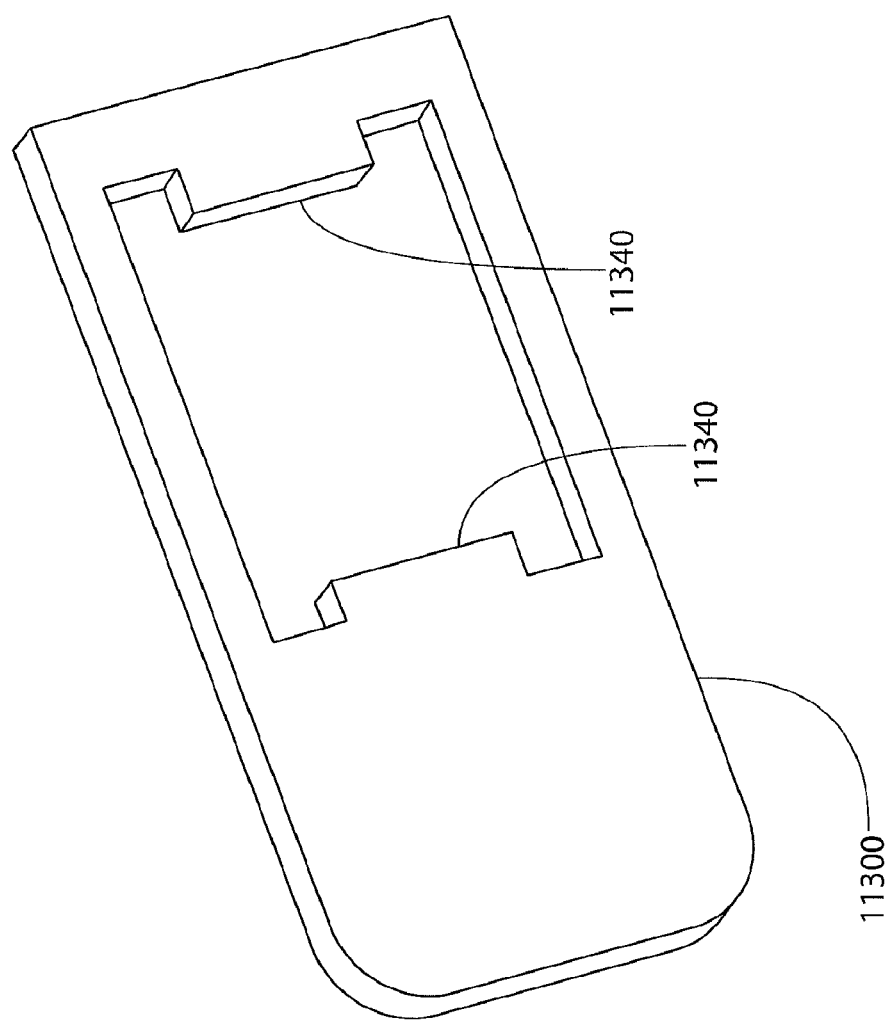
FIGS. 51A to 51D illustrate a sample portion of the exemplary biomarker detector cartridge of FIG. 49, and its components, including the fluid collector of the exemplary biomarker detector cartridge of FIG. 49 (FIG. 51A), the frame of the exemplary biomarker detector cartridge of FIG. 49 (FIG. 51B), the bridge cover of the exemplary biomarker detector cartridge of FIG. 49 (FIG. 51C), and a perspective view of the sample portion of the exemplary biomarker detector cartridge of FIG. 49 (FIG. 51D)
Figure 51B:
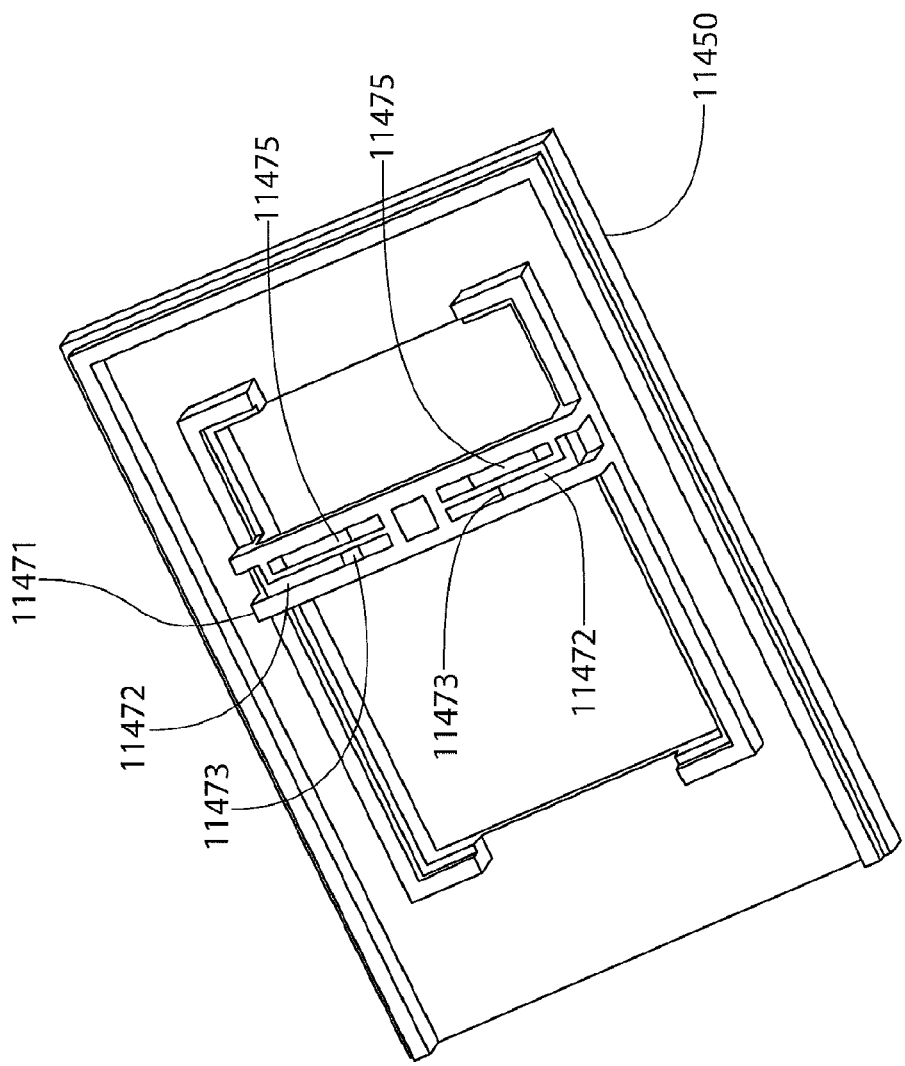

As shown in FIGS. 49, 51B, 51C, and 51D, the invention includes a sample portion 11400 that may include a fluid collector 11300, a frame 11450, a bridge cover 11470, and a bridge manifold 11471. In FIG. 51B the frame 11450 is depicted and is provided to have the fluid collector 11300 fit within the frame 11450. As shown in FIG. 51A, the fluid collector 11300 is provided and may include contact portions 11340 for contacting, and providing fluid communication with, the separation medium 11220 of the assay portion 11500.

In some embodiments, the frame 11450 includes bridge manifold that is disposed to fit proximate to, or over, the assay portion 11500 when such portion is placed in the cartridge body 11150. In some embodiments, the bridge manifold 11471 includes one or more fluid channels 11472 (e.g., 1, 2, 3, or 4 channels) for directing fluid received at the fluid collector 11300 through openings in the channels 11472. In some embodiments, the fluid channels 11472 include a reagent source 11473 that may provide a reagent (e.g., a source of nanoswitches). In some embodiments, fluid may flow through the fluid channels 11472 and dissolve a reagent provided at the reagent source 11473 before depositing the mixture (fluid and reagent) at a loading well of the separation medium 11220. In some embodiments, the bridge manifold 11471 may include vent passages 11475 that may be used to vent a gas during an electrophoretic process. In some embodiments, the channels 11472 are provided to prevent cross contamination between different types of reagent/fluid combinations.

Figure 51C:
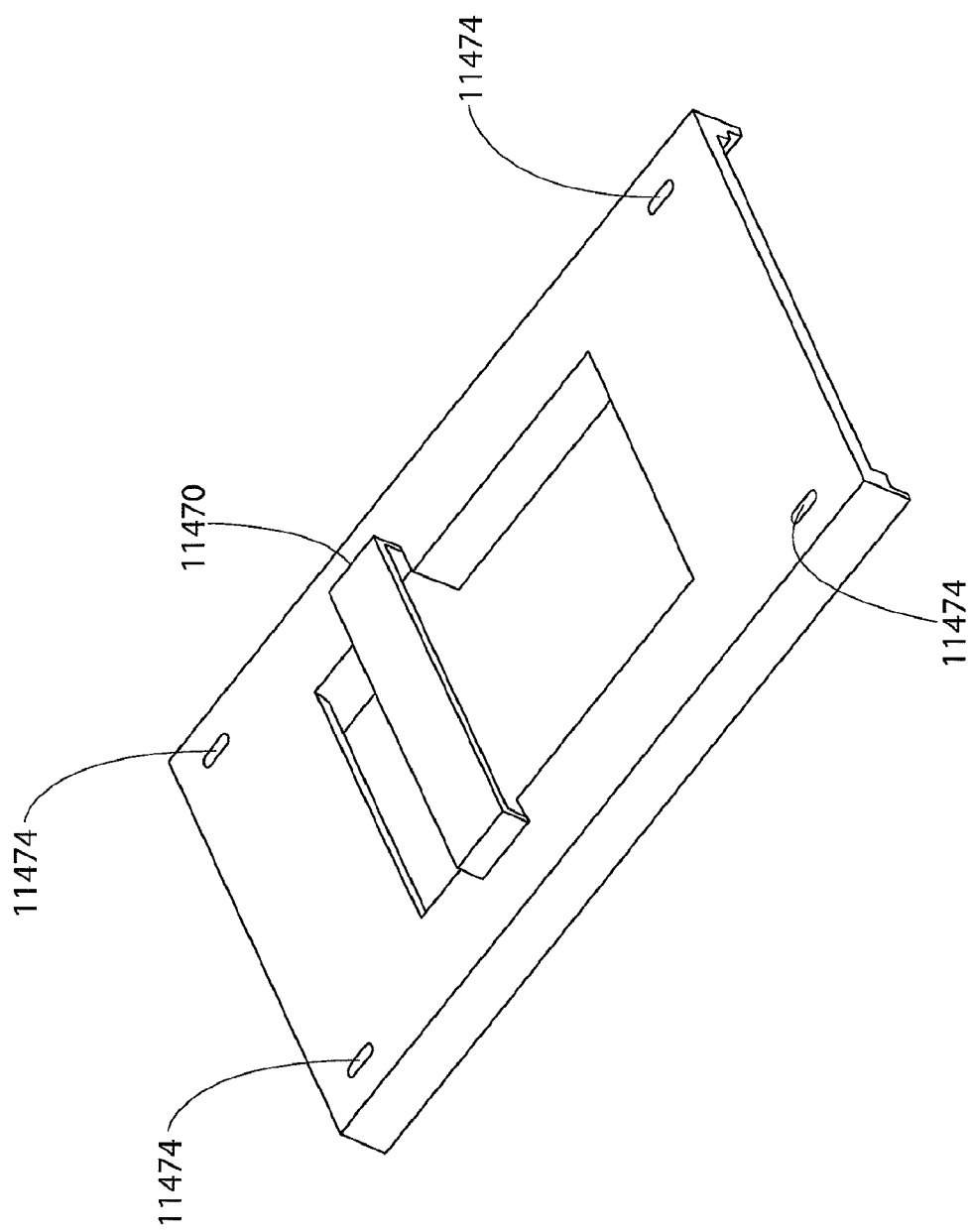
Figure 51D:
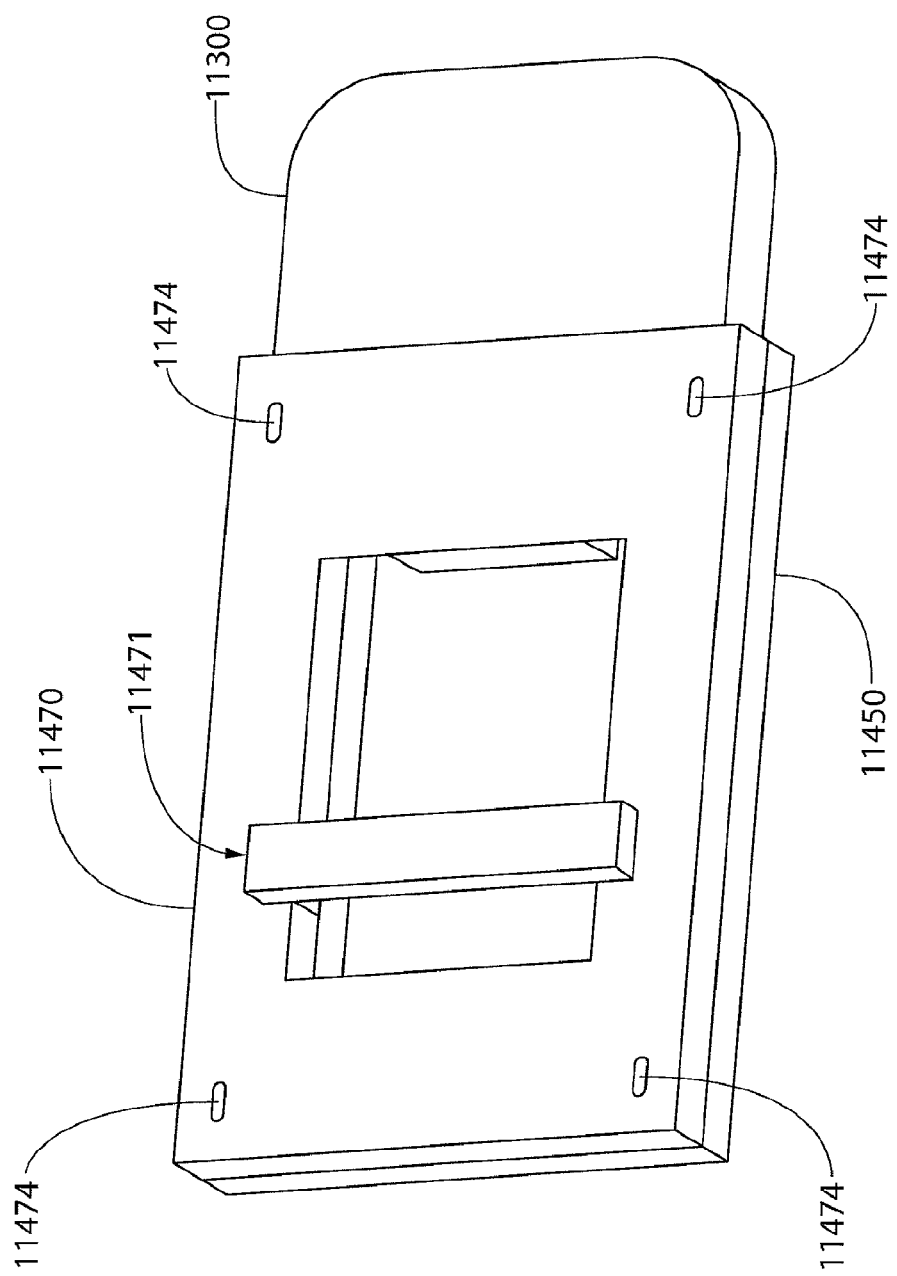

FIGS. 51C and 51D depict a bridge cover 11470 that may be provided to cover the bridge manifold 11471, the frame 11450, and the fluid collector 11300. In some embodiments, the bridge cover 11470 may be connected to the frame 11450 by way of snap or form fitting arrangement. In some embodiments, the bridge cover 11470 may include electrode slots 11474 for accessing the fluid collector 11300 with two or more electrodes (e.g., 2, 3, or 4 electrodes).

FIG. 50 depicts an assay portion 11500 that includes an assay platform 11515 with a separation medium 11220, which may be connected thereto. In some embodiments, the separation medium 11220 may include loading wells 11214 which may be aligned with openings at the fluid channels 11472 when the assay portion 11500 is placed in the cartridge body 11150.

Accordingly, in some embodiments, the biomarker detector cartridge 11000 may be first used to collect a bodily fluid at the fluid collector 11300. After collection is complete, an assay portion 11500 may be removed from a sealed package and inserted into the cartridge body 11150 at the sample portion 11400.

In an embodiment, a method is provided for detecting a biomarker in a fluid. The method may include the step of collecting a fluid that may include a biomarker with a fluid collector of a biomarker detector cartridge. The method may include the step of contacting the fluid with a nanoswitch source. In some embodiments, the method may include delivering or depositing the nanoswitches from a nanoswitch source into the fluid. In some embodiments, the nanoswitch source may be included in the fluid collector to allow for step of collecting the fluid to include mixing nanoswitches from the nanoswitch source with the fluid.

In some embodiments, the method may include the step of transferring the fluid to an electrophoretic cell of the biomarker detector cartridge. The method may include the step of connecting the biomarker detector cartridge to a base for processing such cartridges. The method may include the step of processing a separation medium at the electrophoretic cell and performing electrophoretic analysis at the separation medium. In some embodiments, the step of processing the separation medium may include applying a voltage across the separation medium through the electrical contacts for a selected time period.

In some embodiments the selected time period is at least about 1 minute, or at least about 2 minutes, or at least about 3 minutes, or at least about 4 minutes, or at least about 5 minutes, or at least about 6 minutes, or at least about 7 minutes, or at least about 8 minutes, or at least about 9 minutes, or at least about 10 minutes, or at least about 20 minutes, or at least about 30 minutes, or at least about 40 minutes, or at least about 50 minutes, or at least about 60 minutes. In some embodiments the selected time period is less than about 1 minute, or less than about 2 minutes, or less than about 3 minutes, or less than about 4 minutes, or less than about 5 minutes, or less than about 6 minutes, or less than about 7 minutes, or less than about 8 minutes, or less than about 9 minutes, or less than about 10 minutes, or less than about 20 minutes, or less than about 30 minutes, or less than about 40 minutes, or less than about 50 minutes, or less than about 60 minutes.

In some embodiments, the voltage applied across the separation medium may be at least about 1 µV, or at least about 2 µV, or at least about 3 µV, or at least about 4 µV, or at least about 5 µV, or at least about 6 µV, or at least about 7 µV, or at least about 8 µV, or at least about 9 µV, or at least about 10 µV, or at least about 20 µV, or at least about 30 µV, or at least about 40 µV, or at least about 50 µV, or at least about 60 µV, or at least about 70 µV, or at least about 80 µV, or at least about 90 µV, or at least about 100 µV, or at least about 200 µV, or at least about 300 µV, or at least about 400 µV, or at least about 500 µV, or at least about 600 µV, or at least about 700 µV, or at least about 800 µV, or at least about 900 µV, or at least about 1 mV, or at least about 2 mV, or at least about 3 mV, or at least about 4 mV, or at least about 5 mV, or at least about 6 mV, or at least about 7 mV, or at least about 8 mV, or at least about 9 mV, or at least about 10 mV, or at least about 20 mV, or at least about 30 mV, or at least about 40 mV, or at least about 50 mV, or at least about 60 mV, or at least about 70 mV, or at least about 80 mV, or at least about 90 mV, or at least about 100 mV, or at least about 200 mV, or at least about 300 mV, or at least about 400 mV, or at least about 500 mV, or at least about 600 mV, or at least about 700 mV, or at least about 800 mV, or at least about 900 mV, or at least about 1 V, or at least about 2 V, or at least about 3 V, or at least about 4 V, or at least about 5 V, or at least about 6 V, or at least about 7 V, or at least about 8 V, or at least about 9 V, or at least about 10 V, or at least about 20 V, or at least about 30 V, or at least about 40 V, or at least about 50 V, or at least about 60 V, or at least about 70 V, or at least about 80 V, or at least about 90 V, or at least about 100 V, or at least about 125 V, or at least about 150 V, or at least about 175 V, or at least about 200 V, or at least about 225 V, or at least about 250 V, or at least about 225 V, or at least about 250 V, or at least about 275 V, or at least about 300 V. In some embodiments, the voltage applied across the separation medium may be less than about 1 µV, or less than about 2 µV, or less than about 3 µV, or less than about 4 µV, or less than about 5 µV, or less than about 6 µV, or less than about 7 µV, or less than about 8 µV, or less than about 9 µV, or less than about 10 µV, or less than about 20 µV, or less than about 30 µV, or less than about 40 µV, or less than about 50 µV, or less than about 60 µV, or less than about 70 µV, or less than about 80 µV, or less than about 90 µV, or less than about 100 µV, or less than about 200 µV, or less than about 300 µV, or less than about 400 µV, or less than about 500 µV, or less than about 600 µV, or less than about 700 µV, or less than about 800 µV, or less than about 900 µV, or less than about 1 mV, or less than about 2 mV, or less than about 3 mV, or less than about 4 mV, or less than about 5 mV, or less than about 6 mV, or less than about 7 mV, or less than about 8 mV, or less than about 9 mV, or less than about 10 mV, or less than about 20 mV, or less than about 30 mV, or less than about 40 mV, or less than about 50 mV, or less than about 60 mV, or less than about 70 mV, or less than about 80 mV, or less than about 90 mV, or less than about 100 mV, or less than about 200 mV, or less than about 300 mV, or less than about 400 mV, or less than about 500 mV, or less than about 600 mV, or less than about 700 mV, or less than about 800 mV, or less than about 900 mV, or less than about 1 V, or less than about 2 V, or less than about 3 V, or less than about 4 V, or less than about 5 V, or less than about 6 V, or less than about 7 V, or less than about 8 V, or less than about 9 V, or less than about 10 V, or less than about 20 V, or less than about 30 V, or less than about 40 V, or less than about 50 V, or less than about 60 V, or less than about 70 V, or less than about 80 V, or less than about 90 V, or less than about 100 V, or less than about 125 V, or less than about 150 V, or less than about 175 V, or less than about 200 V, or less than about 225 V, or less than about 250 V, or less than about 225 V, or less than about 250 V, or less than about 275 V, or less than about 300 V. In some embodiments, the voltage applied across the separation medium may be less than about 300 V. In some embodiments, the voltage applied across the separation medium may be about 10 V to about 50 V, or about 20 V to about 40 V, or about 25 V to about 35 V. In some embodiments, the voltage applied across the separation medium may be about 30 V.

The method may include reading the processed separation medium with an electrophoresis cell reader at the base. In some embodiments, reading the processed separation medium may include directing light from a light source through the electrophoretic cell and separation medium. In some embodiments, reading the processed separation medium may include filtering the light from the light source that enters and/or exits the electrophoretic cell and separation medium. In some embodiments, reading the processed separation medium includes receiving the light form the light source that exits the electrophoretic cell and separation medium at a photodetector to capture the results of the electrophoretic analysis (i.e., the results from the processed separation medium).

In some embodiments, the methods may include the step of transferring the results of the electrophoretic analysis wirelessly through a Bluetooth and/or Wi-Fi transmitter another device having a receiver configured to receive such transmitted results including, but not limited to, a handheld device, such as a cell phone, or a computer.

In an embodiment, a kit is provided that includes one or more biomarker detector cartridges and a base as disclosed herein. In some embodiments, the kit includes instructions for using the same. In some embodiments, the kit includes a plurality of biomarker detector cartridges. In some embodiments, the kit includes a first biomarker detector cartridge for testing for a first biomarker and a second biomarker detector cartridge for testing for a second biomarker. In some embodiments, the kit includes kit includes a first biomarker detector cartridge for testing for a first biomarker, a second biomarker detector cartridge for testing for a second biomarker, and a third biomarker detector cartridge for testing for a third biomarker.

In one embodiment, the kit includes 6 biomarker detector cartridges for testing ovulation, 4 biomarker detector cartridges for testing fertilization, and 2 biomarker detector cartridges for testing implantation (i.e., pregnancy).

In another embodiment, the kit includes a biomarker detector cartridge for testing for Zika virus.

In another embodiment, the kit includes 7 biomarker detector cartridges for testing ovulation, 5 biomarker detector cartridges for testing fertilization, 3 biomarker detector cartridges for testing implantation, and 6 biomarker detector cartridges for monitoring embryo development through the first trimester of development.

EXAMPLES

The following example describes the invention in further detail. This example is provided for illustrative purposes only, and should in no way be considered as limiting the invention.

Example 1

Multi-Test Biomarker Detector Cartridge for Testing Ovulation and Pregnancy

Figure 52:
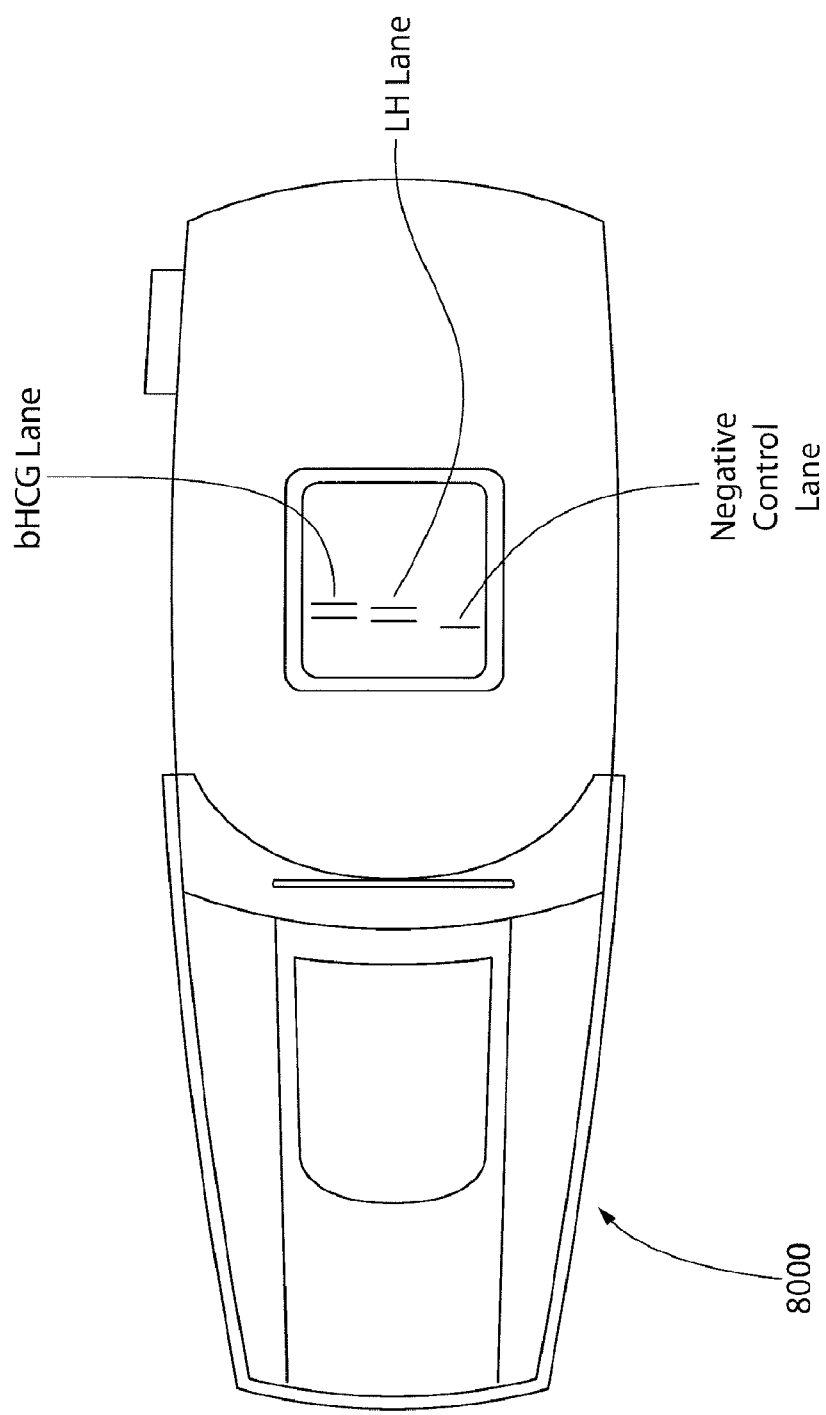
FIG. 52 illustrates an exemplary biomarker detector cartridge that includes dual tests for ovulation and pregnancy.

A biomarker detector cartridge 8000, as described herein, is provided and includes an ovulation test and a pregnancy test. The biomarker detector cartridge of this example during operation is depicted in FIG. 52.

The biomarker detector cartridge can be prepared as shown in FIGS. 20 to 23, which includes three applicators 8301 corresponding to three loading wells 8214. One of the applicators 8301 is provided and includes a reagent source 8302 that acts as a negative control when mixed with urine. The negative control can be negative nanoswitches, which are nanoswitches that cannot form a loop (only has one antibody, or has no antibodies, or has antibodies that do not bind to the analytes or biomarkers present in a urine sample). Alternatively, the negative control can be negative urine. In this alternative, the negative control would be provided to allow for the use of a person's urine, but without the analyte of interest. For example, a negative control as a negative urine lane for an hCG test would require urine to pass through a vast excess of anti-hCG antibodies that would bind all the hCG in the urine. This could also be achieved by flooding the urine sample at the respective applicator with free-floating anti-hCG antibodies. With a negative urine control, all hCG in the sample is extracted (or in the flooding case, all the epitopes are blocked), at the respective applicator, so that there is no free hCG to bind nanoswitches and close the loop. This will allow a user to look at the background or false signal of the nanoswitch in with the same urine sample tested in the various test lanes.

Another of the applicators 8301 includes a reagent source having nanoswitches that are functionalized to bind luteinizing hormone (LH). Leutenizing hormone increases or spikes, as compared to a base line level of LH, following ovulation. The last of the applicators 8301 includes a reagent source having nanoswitches that are functionalized to bind β-human Chorionic Gonadotropin (β-hCG). β-hCG levels as much as quadruple daily following implantation of an embryo. Therefore, as urine is received on the sample portion, and passes through the applicators to the cannula, the urine may be deposited at the loading wells 8214 mixed with one of control nanoswitches (lane 1), nanoswitches that are functionalized to bind LH (lane 2), and nanoswitches functionalized to bind β-hCG (lane 3) (see FIG. 52).

The biomarker detector cartridge can then be loaded into a base (such as base 9000) and the electrophoretic analysis may be read to detect levels of LH and/or β-hCG.

Due to the sensitivities to LH and β-hCG, cross reactivity between LH and β-hCG may become an issue such that high LH levels can give a signal comparable to very low β-hCG levels. To overcome this issue, the exemplary biomarker detector cartridge of this example can test for both LH and β-hCG simultaneously from the same urine sample. With both results in hand, one can ignore a β-hCG signal when there are high levels of LH, thus eliminating false positives resulting from LH cross reactivity.

This also has the added benefit of reducing end-user complexity. Users currently find the process of testing ovulation then pregnancy to be cumbersome and stressful. Part of this stress comes from remembering what test to take and when. By combining LH and β-hCG tests in one cartridge the confusion and hassle are eliminated. The test results and/or information about their menstrual cycle may be used to determine which test (ovulation or pregnancy) to focus on. Additionally, the test results can be used to help determine a woman's menstrual cycle without the need for user input.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the invention as defined by the claims. For example, specific features of the exemplary embodiments may or may not be part of the claimed invention and various features of the disclosed embodiments may be combined. The words "right", "left", "lower" and "upper" designate directions in the drawings to which reference is made. The words "inwardly" and "outwardly" refer to directions toward and away from, respectively, the geometric center of the devices described herein. Unless specifically set forth herein, the terms "a", "an" and "the" are not limited to one element but instead should be read as meaning "at least one".

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All devices, methods, and kits described herein that embody the present invention can, in alternate embodiments, be more specifically defined by any of the transitional terms "comprising," "consisting essentially of" and "consisting of"

It is claimed:
1. A biomarker detector cartridge comprising:
a cartridge body;
a bodily fluid collector coupled to the cartridge body and configured to collect a fluid comprising a biomarker for a biological event;
an electrophoretic cell coupled to the cartridge body and comprising a separation medium; and
a nanoswitch source disposed in the cartridge body and configured to contact the fluid,
wherein the fluid collector comprises the nanoswitch source.
2. The biomarker detector cartridge of claim 1, wherein the cartridge body comprises a channel that fluidly couples the fluid collector to the electrophoretic cell.
3. The biomarker detector cartridge of claim 1, wherein the nanoswitch source comprises a DNA nanoswitch configured to bind the biomarker.

4. The biomarker detector cartridge of claim 1, wherein the nanoswitch source comprises a plurality of nanoswitch sources that comprise:
a first DNA nanoswitch configured to bind a first biomarker; and
a second DNA nanoswitch configured to bind a second biomarker.
5. The biomarker detector cartridge of claim 1, wherein the fluid collector comprises a sponge.
6. The biomarker detector cartridge of claim 1, wherein the separation medium comprises a viscous solution or a gel.
7. The biomarker detector cartridge of claim 6, wherein the gel comprises an agarose gel, a polyacrylamide gel, or a starch gel.
8. The biomarker detector cartridge of claim 1, wherein the electrophoretic cell comprises electrical contacts.
9. The biomarker detector cartridge of claim 1, wherein the fluid comprises a bodily fluid that comprises whole blood, serum, urine, saliva, swabbed samples, mucus, or semen.
10. The biomarker detector cartridge of claim 1, wherein the biomarker for the biological event comprises one or more of a disease biomarker, an inflammation biomarker, a reproduction biomarker, and an aging biomarker.
11. The biomarker detector cartridge of claim 10, wherein the reproduction biomarker comprises one or more of an ovulation biomarker, a fertilization biomarker, an implantation biomarker, and an embryo development biomarker.
12. The biomarker detector cartridge of claim 1, comprising a cap configured to cover the fluid collector before fluid collection or after fluid collection.
13. The biomarker detector cartridge of claim 1, comprising a test result indicator coupled to the electrophoretic cell.
14. A biomarker detector cartridge, comprising:
a cartridge body;
a bodily fluid collector coupled to the cartridge body and configured to collect a fluid comprising a biomarker for a biological event;
an electrophoretic cell coupled to the cartridge body and comprising a separation medium; and
a nanoswitch source disposed in the cartridge body and configured to contact the fluid,
wherein the cartridge body comprises an assay portion and a sample portion that are separable, wherein the assay portion comprises the electrophoretic cell and the sample portion comprises the fluid collector, and wherein the assay portion and the sample portion are separated by a removable barrier.
15. The biomarker detector cartridge of claim 14, wherein the assay portion and the sample portion are connectable.
16. The biomarker detector cartridge of claim 14, wherein the cartridge body comprises a channel that fluidly couples the fluid collector to the electrophoretic cell.
17. The biomarker detector cartridge of claim 14, wherein the nanoswitch source comprises a DNA nanoswitch configured to bind the biomarker.
18. The biomarker detector cartridge of claim 14, wherein the nanoswitch source comprises a plurality of nanoswitch sources that comprise:
a first DNA nanoswitch configured to bind a first biomarker; and
a second DNA nanoswitch configured to bind a second biomarker.
19. The biomarker detector cartridge of claim 14, wherein the separation medium comprises a viscous solution or a gel.

20. The biomarker detector cartridge of claim 19, wherein the gel comprises an agarose gel, a polyacrylamide gel, or a starch gel.

21. The biomarker detector cartridge of claim 14, wherein the fluid comprises a bodily fluid that comprises whole blood, serum, urine, saliva, swabbed samples, mucus, or semen.

22. The biomarker detector cartridge of claim 14, wherein the biomarker for the biological event comprises one or more of a disease biomarker, an inflammation biomarker, a reproduction biomarker, and an aging biomarker.

23. The biomarker detector cartridge of claim 22, wherein the reproduction biomarker comprises one or more of an ovulation biomarker, a fertilization biomarker, an implantation biomarker, and an embryo development biomarker.

24. The biomarker detector cartridge of claim 14, comprising a cap configured to cover the fluid collector before fluid collection or after fluid collection.

25. The biomarker detector cartridge of claim 14, comprising a test result indicator coupled to the electrophoretic cell.

26. A biomarker detector cartridge, comprising:
a cartridge body;
a bodily fluid collector coupled to the cartridge body and configured to collect a fluid comprising a biomarker for a biological event;
an electrophoretic cell coupled to the cartridge body and comprising a separation medium; and
a nanoswitch source disposed in the cartridge body and configured to contact the fluid, wherein the electrophoretic cell comprises a stain.

27. The biomarker detector cartridge of claim 26, wherein the cartridge body comprises a channel that fluidly couples the fluid collector to the electrophoretic cell.

28. The biomarker detector cartridge of claim 26, wherein the fluid collector comprises the nanoswitch source.

29. The biomarker detector cartridge of claim 26, wherein the nanoswitch source comprises a DNA nanoswitch configured to bind the biomarker.

30. The biomarker detector cartridge of claim 26, wherein the nanoswitch source comprises a plurality of nanoswitch sources that comprise:
a first DNA nanoswitch configured to bind a first biomarker; and
a second DNA nanoswitch configured to bind a second biomarker.

31. The biomarker detector cartridge of claim 26, wherein the separation medium comprises a viscous solution or a gel.

32. The biomarker detector cartridge of claim 31, wherein the gel comprises an agarose gel, a polyacrylamide gel, or a starch gel.

33. The biomarker detector cartridge of claim 26, wherein the fluid comprises a bodily fluid that comprises whole blood, serum, urine, saliva, swabbed samples, mucus, or semen.

34. The biomarker detector cartridge of claim 33, wherein the biomarker for the biological event comprises one or more of a disease biomarker, an inflammation biomarker, a reproduction biomarker, and an aging biomarker.

35. The biomarker detector cartridge of claim 34, wherein the reproduction biomarker comprises one or more of an ovulation biomarker, a fertilization biomarker, an implantation biomarker, and an embryo development biomarker.

36. A biomarker detector cartridge, comprising:
a cartridge body;
a bodily fluid collector coupled to the cartridge body and configured to collect a fluid comprising a biomarker for a biological event;
an electrophoretic cell coupled to the cartridge body and comprising a separation medium;
a nanoswitch source disposed in the cartridge body and configured to contact the fluid; and
a cap configured to compress the fluid collector after fluid collection to direct collected fluid to the electrophoretic cell.

37. The biomarker detector cartridge of claim 36, comprising a test result indicator coupled to the electrophoretic cell.

38. The biomarker detector cartridge of claim 36, wherein the cartridge body comprises a channel that fluidly couples the fluid collector to the electrophoretic cell.

39. The biomarker detector cartridge of claim 36, wherein the fluid collector comprises the nanoswitch source.

40. The biomarker detector cartridge of claim 36, wherein the nanoswitch source comprises a DNA nanoswitch configured to bind the biomarker.

41. The biomarker detector cartridge of claim 36, wherein the nanoswitch source comprises a plurality of nanoswitch sources that comprise:
a first DNA nanoswitch configured to bind a first biomarker; and
a second DNA nanoswitch configured to bind a second biomarker.

42. The biomarker detector cartridge of claim 36, wherein the separation medium comprises a viscous solution or a gel.

43. The biomarker detector cartridge of claim 42, wherein the gel comprises an agarose gel, a polyacrylamide gel, or a starch gel.

44. The biomarker detector cartridge of claim 36, wherein the electrophoretic cell comprises a stain.

45. The biomarker detector cartridge of claim 36, wherein the fluid comprises a bodily fluid that comprises whole blood, serum, urine, saliva, swabbed samples, mucus, or semen.

46. The biomarker detector cartridge of claim 36, wherein the biomarker for the biological event comprises one or more of a disease biomarker, an inflammation biomarker, a reproduction biomarker, and an aging biomarker.

47. The biomarker detector cartridge of claim 46, wherein the reproduction biomarker comprises one or more of an ovulation biomarker, a fertilization biomarker, an implantation biomarker, and an embryo development biomarker.

48. The biomarker detector cartridge of claim 36, comprising a test result indicator coupled to the electrophoretic cell.

49. A biomarker detector cartridge, comprising:
a cartridge body;
a bodily fluid collector coupled to the cartridge body and configured to collect a fluid comprising a biomarker for a biological event;
an electrophoretic cell coupled to the cartridge body and comprising a separation medium; and
a nanoswitch source disposed in the cartridge body and configured to contact the fluid, wherein wherein the nanoswitch source comprises a sticker, a capsule, a pellet, or a residue.

50. The biomarker detector cartridge of claim 49, wherein the cartridge body comprises a channel that fluidly couples the fluid collector to the electrophoretic cell.

51. The biomarker detector cartridge of claim 49, wherein the fluid collector comprises the nanoswitch source.

52. The biomarker detector cartridge of claim 49, wherein the nanoswitch source comprises a DNA nanoswitch configured to bind the biomarker.

53. The biomarker detector cartridge of claim 49, wherein the nanoswitch source comprises a plurality of nanoswitch sources that comprise:
   a first DNA nanoswitch configured to bind a first biomarker; and
   a second DNA nanoswitch configured to bind a second biomarker.

54. The biomarker detector cartridge of claim 49, wherein the separation medium comprises a viscous solution or a gel.

55. The biomarker detector cartridge of claim 54, wherein the gel comprises an agarose gel, a polyacrylamide gel, or a starch gel.

56. The biomarker detector cartridge of claim 49, wherein the electrophoretic cell comprises a stain.

57. The biomarker detector cartridge of claim 49, wherein the bodily fluid comprises whole blood, serum, urine, saliva, swabbed samples, mucus, or semen.

58. The biomarker detector cartridge of claim 49, wherein the biomarker for the biological event comprises one or more of a disease biomarker, an inflammation biomarker, a reproduction biomarker, and an aging biomarker.

59. The biomarker detector cartridge of claim 58, wherein the reproduction biomarker comprises one or more of an ovulation biomarker, a fertilization biomarker, an implantation biomarker, and an embryo development biomarker.

60. The biomarker detector cartridge of claim 49, comprising a cap configured to cover the fluid collector before fluid collection or after fluid collection.

* * * * *